US011602368B2

(12) United States Patent
Smith

(10) Patent No.: US 11,602,368 B2
(45) Date of Patent: Mar. 14, 2023

(54) POSTERIOR TO LATERAL INTERBODY FUSION APPROACH WITH ASSOCIATED INSTRUMENTATION AND IMPLANTS

(71) Applicant: Jeffrey Scott Smith, Granbury, TX (US)

(72) Inventor: Jeffrey Scott Smith, Granbury, TX (US)

( * ) Notice: Subject to any disclaimer, the term of this patent is extended or adjusted under 35 U.S.C. 154(b) by 603 days.

(21) Appl. No.: 16/735,374

(22) Filed: Jan. 6, 2020

(65) Prior Publication Data

US 2020/0138466 A1 May 7, 2020

Related U.S. Application Data

(63) Continuation-in-part of application No. 15/255,679, filed on Sep. 2, 2016, now Pat. No. 10,524,819.
(Continued)

(51) Int. Cl.
*A61B 17/32* (2006.01)
*A61B 17/34* (2006.01)
(Continued)

(52) U.S. Cl.
CPC ........ *A61B 17/32002* (2013.01); *A61F 2/442* (2013.01); *A61F 2002/30579* (2013.01)

(58) Field of Classification Search
CPC ...... A61B 17/320016; A61B 17/32002; A61B 17/1757; A61B 17/1671; A61B 17/16; A61B 2017/320024; A61B 2017/320028; A61B 2017/320032; A61B 2017/32004; A61B 2017/320044; A61B 2017/320048; A61B 2017/320052; A61B 2017/320056; A61B 2017/32006; A61B 2017/320064; A61B 2017/00261; A61B 2017/0256; A61F 2/4611; A61F 2/44; A61F 2/4455; A61F 2002/4625; A61F 2002/4627; A61F 2002/4628
See application file for complete search history.

(56) References Cited

U.S. PATENT DOCUMENTS

| 5,195,541 A | 3/1993 | Obenchain |
| 6,122,549 A | 9/2000 | Sharkey |

(Continued)

OTHER PUBLICATIONS

U.S. Appl. No. 15/255,679, filed Dec. 5, 2018, Office Action.
(Continued)

*Primary Examiner* — Dianne Dornbusch
(74) *Attorney, Agent, or Firm* — Workman Nydegger

(57) ABSTRACT

Methods for accessing a disc space of a patient as a part of an interbody fusion, as well as the tools employed therewith. An exemplary method may include inserting a leading end of a tool into the patient's back at a location on the posterior surface that is laterally offset from a patient's spinous process and disc. The tool's initial entry into the patient may be from a posterior approach. As the tool is advanced along its designated path, it begins to deviate from the posterior approach towards a lateral approach. When the leading end reaches the disc, it may access the disc from a lateral or substantially lateral location. The tool may be used to access the disc location, to remove disc material, to deliver a cutting tool for removing the disc material, and other steps associated with the spinal interbody fusion procedure.

19 Claims, 48 Drawing Sheets

Related U.S. Application Data

(60) Provisional application No. 62/956,995, filed on Jan. 3, 2020, provisional application No. 62/382,007, filed on Aug. 31, 2016, provisional application No. 62/370,928, filed on Aug. 4, 2016, provisional application No. 62/270,013, filed on Dec. 20, 2015, provisional application No. 62/214,489, filed on Sep. 4, 2015.

(51) Int. Cl.
*A61F 2/44* (2006.01)
*A61F 2/30* (2006.01)

(56) References Cited

U.S. PATENT DOCUMENTS

| | | | |
|---|---|---|---|
| 6,517,568 B1 | 2/2003 | Sharkey | |
| 6,558,386 B1 | 5/2003 | Cragg | |
| 6,575,979 B1 | 6/2003 | Cragg | |
| 6,740,090 B1 | 5/2004 | Cragg | |
| 7,959,634 B2 | 6/2011 | Sennett | |
| 8,845,728 B1 | 9/2014 | Abdou | |
| 8,979,928 B2 | 3/2015 | Donner | |
| 9,421,109 B2 | 8/2016 | Donner | |
| 9,675,303 B2 | 6/2017 | Choi | |
| 9,724,107 B2 * | 8/2017 | Pellegrino | A61B 17/3421 |
| 10,524,819 B2 | 1/2020 | Smith | |
| 2001/0049527 A1 | 12/2001 | Cragg | |
| 2002/0016583 A1 | 2/2002 | Cragg | |
| 2002/0095144 A1 | 7/2002 | Carl | |
| 2002/0165550 A1 | 11/2002 | Frey | |
| 2002/0173796 A1 | 11/2002 | Cragg | |
| 2003/0191474 A1 * | 10/2003 | Cragg | A61B 17/3203 606/79 |
| 2003/0216737 A1 | 11/2003 | Biscup | |
| 2005/0010205 A1 | 1/2005 | Hovda | |
| 2005/0261695 A1 | 11/2005 | Cragg | |
| 2007/0055260 A1 * | 3/2007 | Cragg | A61B 17/1671 606/79 |
| 2007/0198021 A1 | 8/2007 | Wales | |
| 2008/0208196 A1 * | 8/2008 | Daum | A61B 17/32002 606/80 |
| 2008/0255563 A1 | 10/2008 | Farr | |
| 2009/0131948 A1 * | 5/2009 | Liu | A61M 25/0152 606/92 |
| 2009/0216234 A1 | 8/2009 | Farr | |
| 2010/0217269 A1 | 8/2010 | Landes | |
| 2010/0331883 A1 | 12/2010 | Schmitz | |
| 2013/0006232 A1 * | 1/2013 | Pellegrino | A61B 18/082 606/33 |
| 2013/0103103 A1 | 4/2013 | Mire | |
| 2015/0025514 A1 * | 1/2015 | Carl | A61B 18/02 606/21 |
| 2016/0302936 A1 * | 10/2016 | Billon | A61F 2/442 |
| 2017/0348034 A1 * | 12/2017 | LaPierre | A61B 17/3421 |

OTHER PUBLICATIONS

U.S. Appl. No. 15/255,679, filed Mar. 25, 2019, Final Office Action.
U.S. Appl. No. 15/255,679, filed Aug. 21, 2019, Notice of Allowance.

* cited by examiner

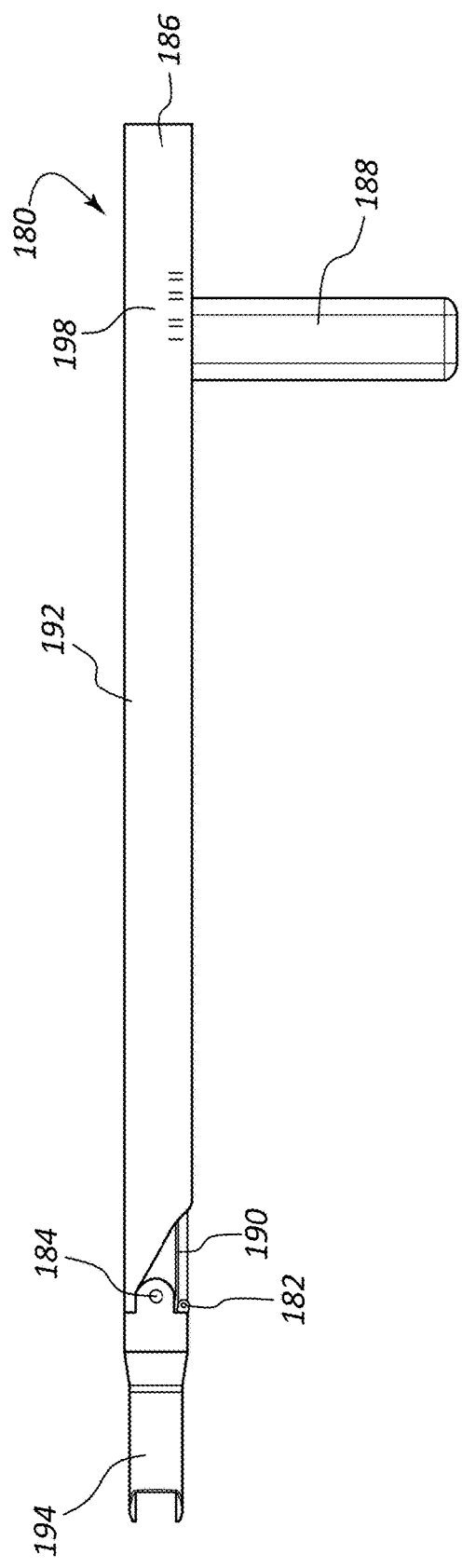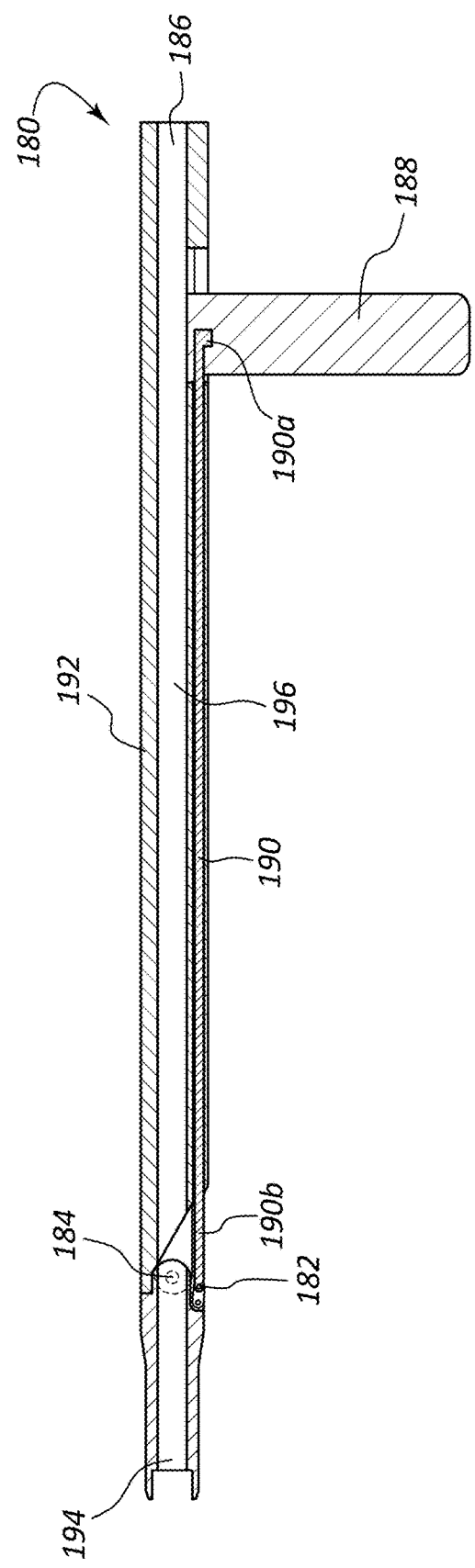
FIG. 6A
FIG. 6B

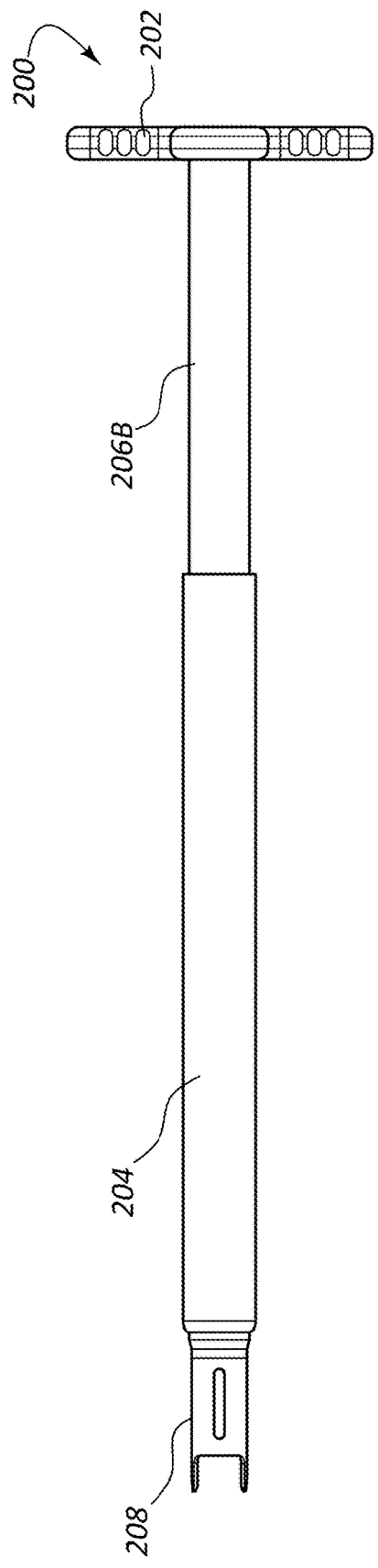
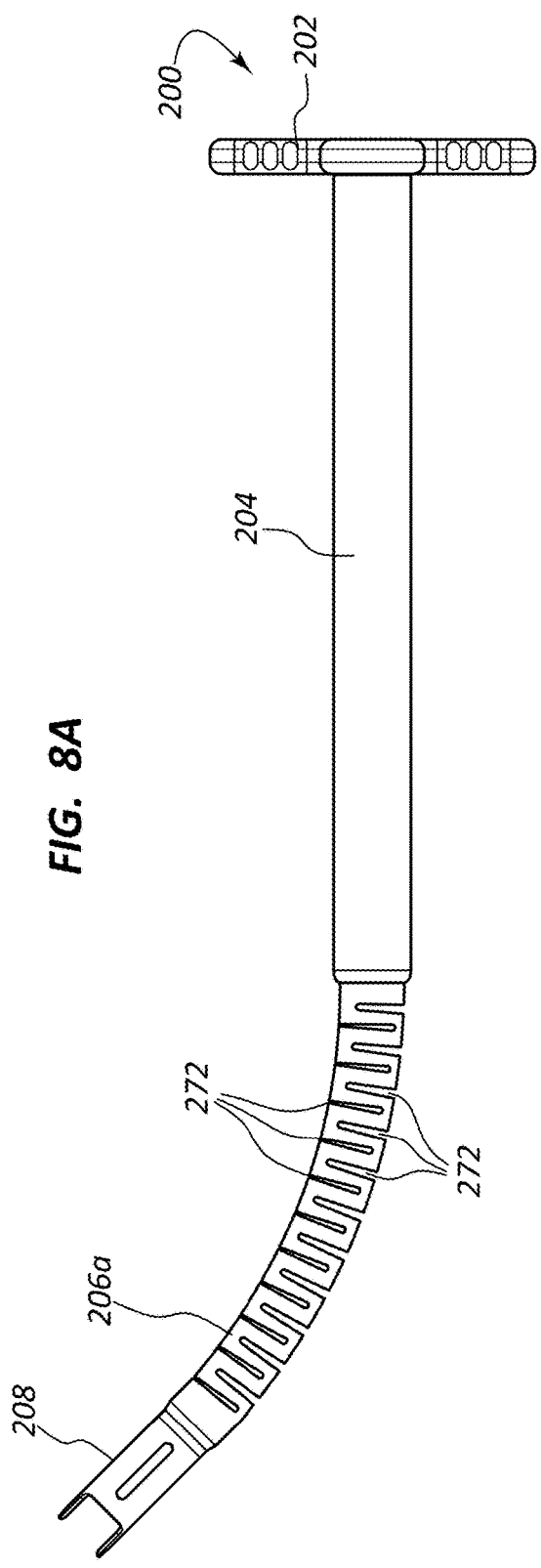
FIG. 8A
FIG. 8B

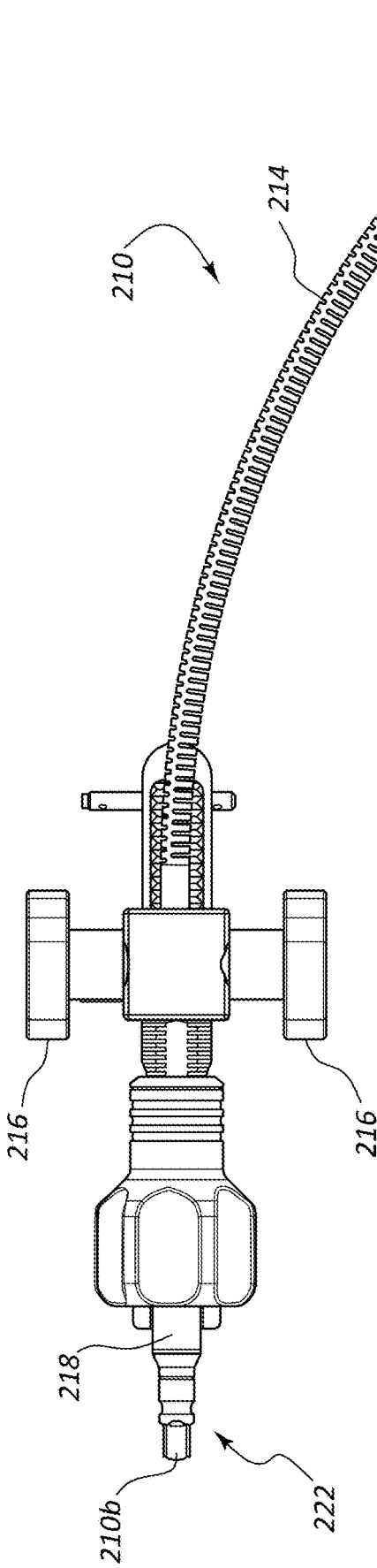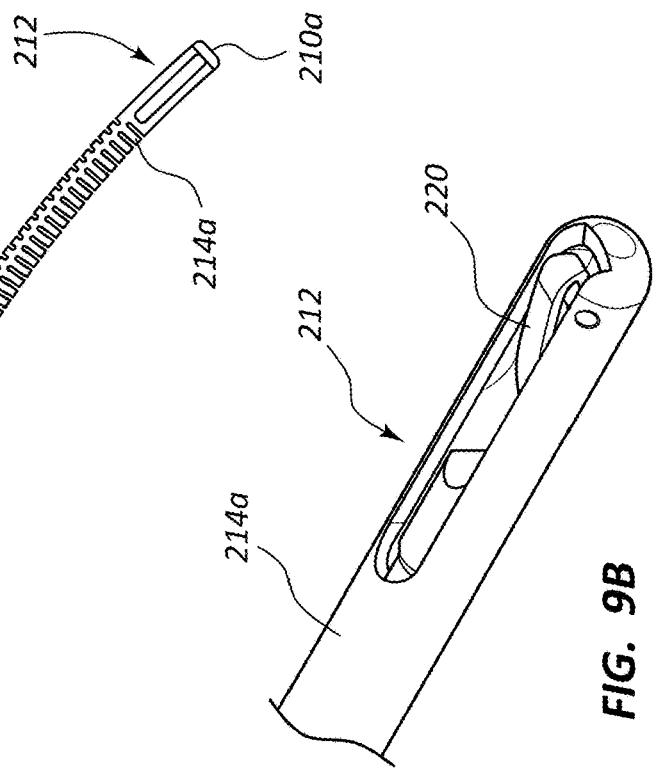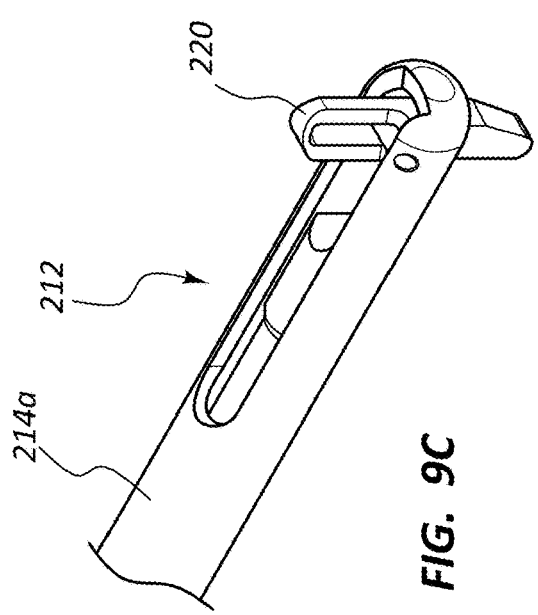
FIG. 9A
FIG. 9B
FIG. 9C

POSTERIOR TO LATERAL INTERBODY FUSION APPROACH WITH ASSOCIATED INSTRUMENTATION AND IMPLANTS

CROSS-REFERENCE TO RELATED APPLICATIONS

The present application claims the benefit under 35 USC 119(e) of U.S. Patent Application Ser. No. 62/956,995, filed Jan. 3, 2020 and entitled "POSTERIOR TO LATERAL APPROACH". The present application is also a continuation-in-part of U.S. patent application Ser. No. 15/255,679 filed Sep. 2, 2016, now U.S. Pat. No. 10,524,819, which claims the benefit under 35 USC 119(e) of U.S. patent application Ser. No. 62/370,928, filed Aug. 4, 2016 and entitled "POSTERIOR TO LATERAL APPROACH", which includes screen captures from an animation prepared by the inventor of the presently described methods. application Ser. No. 15/255,679 also claims the benefit under 35 USC 119(e) of U.S. Patent Application Ser. No. 62/382,007, filed Aug. 31, 2016 and entitled "POSTERIOR TO LATERAL APPROACH. Application Ser. No. 15/255,679 also claims the benefit under 35 USC 119(e) of U.S. Patent Application Ser. No. 62/270,013, filed Dec. 20, 2015 and entitled "POSTERIOR TO LATERAL APPROACH FOR INTERBODY SPINAL FUSION", as well as U.S. Patent Application Ser. No. 62/214,489, filed Sep. 4, 2015 and entitled "EXPANDABLE INTERBODY FUSION DEVICE" The disclosure of each of the foregoing is herein incorporated by reference in its entirety.

BACKGROUND OF THE INVENTION

1. The Field of the Invention

The present invention generally relates to methods for accessing one or more discs of the vertebrae, e.g., as part of a spinal interbody fusion, as well as devices for use therewith.

2. The Relevant Technology

Over the past several decades, spinal surgery has increasingly become an important option available to surgeons and patients in treating issues related to the spine. Because the spine generally provides support and movement for the body, a problem with the spine (e.g., a back disorder) can disrupt even the simplest life activities. In general, thousands of surgical interbody fusions of the spine are performed each year in an attempt to decrease pain and to increase function for the patient. Interbody fusion is a common procedure that attempts to create a bony bridge, or union, between two vertebral bodies to eliminate movement between the two individual vertebrae. This loss of motion can be curative for those suffering from a variety of back disorders, including degenerative conditions or instabilities.

Many different methods are currently in use by surgeons to accomplish interbody fusion Generally, an incision is made, and the disc is exposed and the disc material is removed. The end plates of the vertebral bodies may be stripped of any remaining cartilage thus exposing the bony faces of the adjacent vertebrae. The disc space may be filled with a material compatible with fusion. In most cases, the disc space may also be filled with some sort of implant, or spacer, intended to prevent narrowing, filling, or collapse of the disc space during the fusion process. Generally speaking, the greater the agitation, scraping, or other "damage" to the vertebral endplates, the greater the biologic efforts effected by the body to heal the damage, thus creating the fusion. Current approaches used by spinal surgeons to access the disc space and accomplish an interbody fusion typically include anterior, posterior, posterolateral, or a lateral approach.

Surgical techniques currently available are reliable, but they are not without risk and potential complications. Reducing risk without reducing the effectiveness of the surgery is desirable. In addition, it would be advantageous if new techniques better limited the amount of surgical trauma to the patient, reducing recuperation and healing times. As such, there exists a continuing need for improved techniques for performing interbody spinal fusion.

BRIEF SUMMARY

In one aspect, the present invention relates to methods for accessing a disc of a patient's vertebrae as part of a spinal interbody fusion Anterior approaches require mobilization of the vascular structures in the region and can cause injury to the sympathetic plexus. Posterior and posterolateral approaches can present a risk to nerve roots as well as to the bones of the spine which must be navigated around as the practitioner accesses the location of the disc to be removed and fused A lateral approach, while lessening such risk to nerve roots and bone tissues adjacent the location to be accessed, presents increased risk to the colon and to the lumbar plexus. The present disclosure proposes a new technique that would begin as a posterior approach, but becomes a lateral approach as the disc location is actually approached, herein referred to as a posterior to lateral approach Such method may provide the surgeon with a technique that can be performed reliably, with an acceptable safety profile, and predictable outcomes. The procedure is designed to be capable of being performed in a minimally invasive manner. It is anticipated that the procedure would be safe and reliable, with safety and reliability characteristics improved over current techniques, so as to be suitable for use by both spine surgeons, as well as interventional pain management doctors.

In the novel posterior to lateral approach, the disc location is accessed directly laterally, or nearly directly laterally (e.g., some angular offset from directly lateral may be acceptable) after an initial entry from the posterior surface (i.e., the back) of the patient According to one embodiment, one such method may include inserting a leading end of a tool (e.g. a cannula) into the patient's back at a location on the posterior surface that is laterally offset from a patient's midline (e.g., midline and spinous process) The tool may begin with an initial entry into the patient from a posterior (or perhaps more accurately posterolateral) approach relative to the disc. The tool may continue to be advanced along a path which may begin to deviate from the posterior (or posterolateral) approach towards a lateral approach as the tool is advanced toward a lateral aspect of the disc. When the leading end of the tool actually reaches the disc location, it may access the disc location from a location that is lateral relative to the disc location. The tool may be used to access the disc location, to remove disc material, to deliver a cutting tool for removing the disc material, and other steps associated with the spinal interbody fusion procedure performed from a lateral perspective.

In a embodiment, the leading end of a guide wire may be inserted into the patient's back at a location on the posterior surface that is laterally offset from the midline The guide wire may be advanced to the lateral aspect of the disc, or through the lateral aspect of the disc, into the central portion of the disc. The tool may then be inserted over the guide wire into the patient from the same offset posterior starting location. The tool may continue to be advanced along the path established by the guidewire which may begin to deviate from the posterior approach towards a lateral approach as the tool is advanced toward a lateral aspect of the disc. When the leading end of the tool reaches the lateral aspect of the disc, the tool, or a subsequent tool may be used to access the disc location, to remove disc material, to deliver a cutting tool for removing the disc material, and/or other steps associated with the spinal interbody fusion procedure performed from a lateral perspcective.

A posterior to lateral approach has several distinct advantages because it may mitigate some risks associated with other approaches typically used in spinal interbody fusion procedures. For example, an anterior approach requires retraction of a peritoneal sac and large bloos vessels (e.g., left common iliac vein) in order to access the disc. Access to the lumbar disc is difficult using a posterior approach because the patient's spinal canal, including the contained nerve roots, other structures, and bone of the patient (including the facet joints) block easy access to the disc. As a result, lamina must be removed and nerve roots retracted before the disc can be accessed. A lateral approach initially presents a risk to a patient's colon, which must be carefully bypassed to access the disc. The posterior to lateral approach described herein is designed to avoid damage and risk to these structures. For example, the posterior to lateral approach may be performed in a manner so that the pathway only passes through the patient's skin and muscle (e.g., psoas muscle) to access the disc, making the approach potentially much less invasive, while maintaining the advantages of accessing the disc space from a lateral perspective.

Because the posterior to lateral approach may be less invasive, only passing through muscle tissue, which can easily be parted to one side or the other, without necessarily cutting or damaging the muscle, the healing time for a patient undergoing spinal interbody fusion using the posterior to lateral approach may be far less than other available approaches. In fact, for many patients such a procedure may be performed on an outpatient basis.

In another embodiment according to the present disclosure, the method may include measuring a distance from a point between the patient's skin and the patient's spinous process to the center of the disc based on a scan (e.g., preoperative), and securing a device that may rotate over a posterior surface of the patient's back with a trailing end of a tool coupled to the device. The device may include an arm which may or may not rotate having a length that is based on the measured distance from a desired starting point located between the spinous process and the surface of the skin to the disc center (determined from the scan). In an embodiment, the starting point for the measured distance may be the tip of the spinous process. A leading end of the tool may be inserted into the posterior surface of the patient's back along a predetermined path that begins (during initial entry) as a posterior approach to the disc. Once the tool is inserted, the tool may be advanced along the predetermined path, which deviates from the posterior approach towards a lateral approach as the tool is advanced from the posterior surface until it reaches a lateral aspect of the disc. The tool may be used to access the disc and perform at least a portion of the spinal interbody fusion (e.g., deliver a cutting tool for removing the disc material, actually removing the disc material, delivering an implant into the disc space, etc.).

In another aspect, the present disclosure is directed to a cutting device (e.g., for use with a tool as described herein) for clearing a disc space of a patient's vertebrae between vertebral endplates of the vertebrae as part of a spinal interbody fusion. Such a cutting device may include a straight or flexible drive shaft, which may be cannulated to pass over a guide wire. A retractable blade may be provided at the distal end of the shaft. The retractable blade may be operably coupled to an extension mechanism at a proximal end of the shaft (e.g., so as to be easily manipulated by the practitioner) that is configured to adjust an angle that the blade extends from the distal end of the shaft relative to a longitudinal axis of the device. In other words, the extension mechanism may allow the blade to be selectively extended from the distal end of the device, at a desired angle thereto, so that upon rotation of the blade, a given radius (or diameter) cut or clearing action results. The blade may be operably coupled to an actuating mechanism that allows the practitioner to selectively rotate the blade (e.g., a quick connector or similar connection to a drill or other power source for rotating the shaft and blade).

The use of a guide wire placed across the disc space in a lateral, or side-to-side orientation, may help to maintain the cutting device in its desired location during cutting. In order to more securely control the path of the cutting device, particularly while the device is actually cutting, the guide wire may have a feature on the leading end which allows the leading end of the guide wire to be captured and secured. This feature may be as simple as a small sphere or other protrusion on the leading end of the guide wire, or a similar feature. In order to secure the leading end of the guide wire, it first traverses the disc space in a lateral orientation. The wire is advanced such that a portion of the wire, including the leading end with its capture feature may extend beyond the lateral confines of the disc and the annulus. In the lumbar spine, the tip of the end of the guide wire may of necessity, extend beyond the confines of the disc, and even into the psoas muscle for a distance sufficient to allow the wire to be captured.

The practitioner may then place a capturing tool into the psoas muscle on the same side of the leading end of the guide wire from a posterior or posterolateral approach. The capturing tool may be advanced along a straight path until the leading end of the capturing tool is near the location of the leading end of the guide wire. The leading end of the guide wire may then be captured and secured by the capture tool. In one embodiment, the capture tool may include a loop made from metal or other material that is initially withdrawn into a containment sleeve. The loop may be extended out of the end of the containment sleeve (e.g., a tube) and the loop then expands into a circular, or other shape. This loop then becomes a target through which the end of the guide wire is passed. Once the end of the guide wire has passed through the loop (e.g., including the capture feature on the end of the guide wire), the loop may be withdrawn back inside the containment sleeve or otherwise at least partially retracted until the loop has effective captured and secured the end of the guide wire. The capture tool may remain secured to stabilize the end of the guide wire, and prevent it from migrating, until the cutting process has been completed. Stabilizing the end of the guide wire in this or a similar manner may prevent the wire from migrating and keep the cutting device from deviating from a path desired by the practitioner.

These and other advantages and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 6A shows a perspective view of an exemplary hinged cannula comprising a mechanical linkage, with the hinge shown in the straight position.

FIG. 6B is a cross-sectional view through the hinged cannula of FIG. 6A.

FIG. 8A is a perspective view of an exemplary pre-stressed cannula which may be used with an outer sleeve or inner stylet which can be positioned over or within the pre-stressed cannula to hold the pre-stressed cannula in a straight configuration.

FIG. 8B is a perspective view of the pre-stressed cannula of FIG. 8A, shown with the outer sleeve retracted from over the pre-stressed portion of the cannula, so that the pre-stressed portion defaults to its curved configuration.

FIG. 9A is a perspective view of an exemplary cutting device in which at least a portion of the drive shaft is flexible to better allow its following any of the posterior to lateral approaches described herein.

FIG. 9B is a close up view of the distal end of the cutting device of FIG. 9A with the blade shown retracted into the distal end of the cutting device.

FIG. 9C is a close up view of the distal end of the cutting device of FIG. 9A with the blade shown extended laterally from the distal end of the cutting device.

DETAILED DESCRIPTION OF THE PREFERRED EMBODIMENTS

I. Introduction

Figure 1:
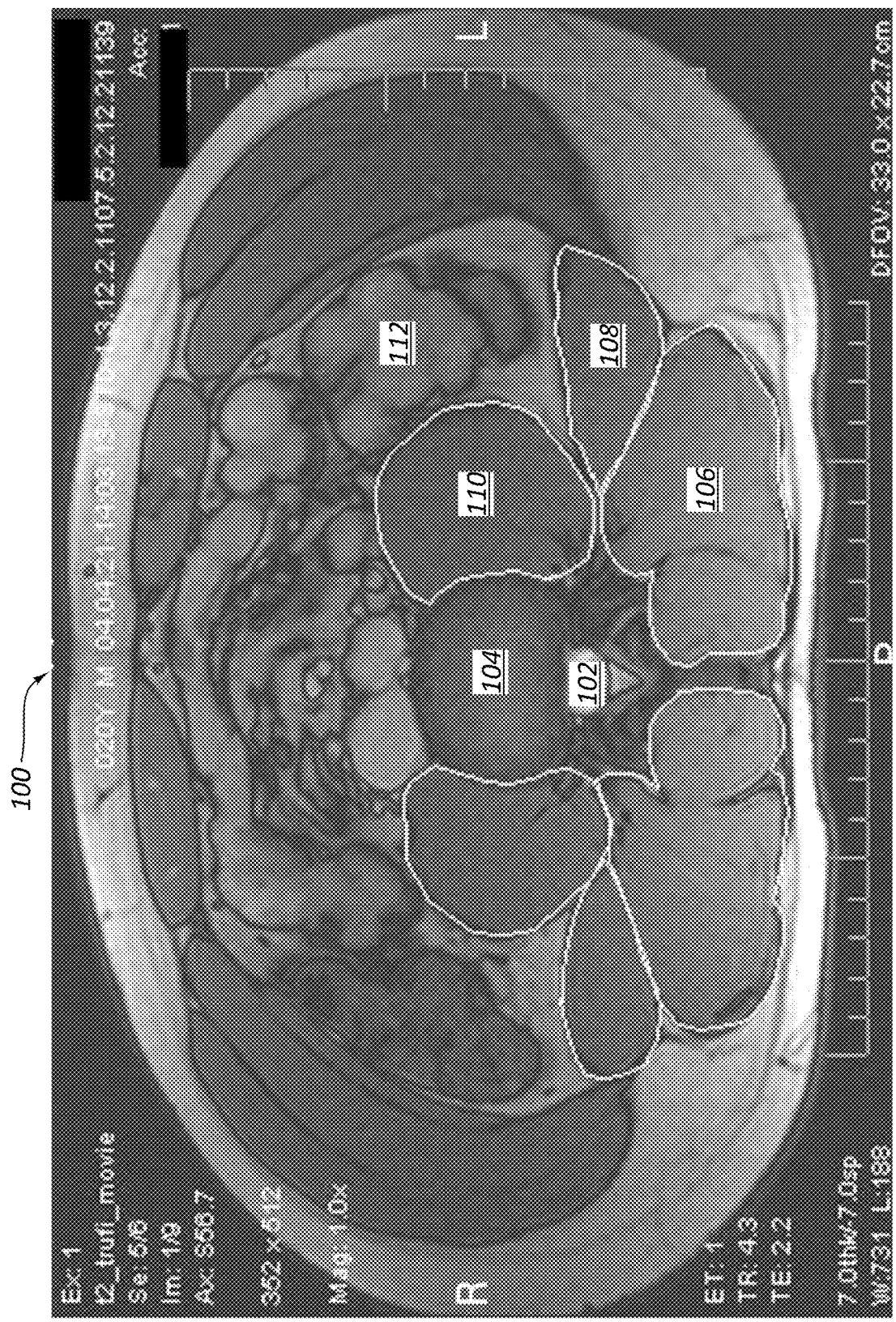
FIG. 1 is a cross-sectional scan through a patient's body, showing the various structures near the vertebrae and disc to be fused.

The present invention relates to methods used for accessing a disc space of a patient as a part of an interbody fusion procedure, as well as the tools used for clearing the disc space of the patient between vertebral endplates of the vertebrae as a part of such an interbody fusion. Such a method may include inserting a leading end of a tool into the patient's back at a location on the posterior surface that is laterally offset from a patient's midline (e.g., spinous process). The tool's initial entry into the patient may be from a posterior approach relative to the disc (although laterally offset as described, so as to perhaps most accurately be described as posterolateral), but as the tool is advanced along its designated path towards the lateral aspect of the disc, or after it has fully advanced to the lateral aspect of the disc, the path is deviated from the posterior approach towards a lateral approach to the disc. When the leading end of the tool actually reaches the disc location, it may access the disc location from a location that is lateral (or substantially lateral) relative to the disc location. The tool or a subsequently placed tool may be used to access the disc location, to remove disc material, to deliver a cutting tool for removing the disc material, and other steps associated with the spinal interbody fusion procedure.

Another aspect of the present disclosure relates to methods for accessing the disc space of a patient that may include measuring a distance from a point between the skin and the patient's spinous process to the disc center from a scan (e.g., preoperative scan), and then securing a guiding device (which may or may not rotate) over a posterior surface of the patient's back to a tool. The guiding device may include an arm having a length that is based on the measured distance from the point previously determined (e.g., between the spinous process and the disc center). In some embodiments, the arm may be rotatable. A leading end of the tool may be inserted into the posterior surface of the patient's back. Once the tool is inserted, the tool may be advanced along the predetermined path, which begins as a posterior (or posterolateral) approach but deviates from the posterior approach towards a lateral approach as the tool is advanced from the posterior surface until it reaches a lateral or substantially lateral aspect of the disc. The tool or a subsequent tool may be used to access the disc and perform at least a portion of the spinal interbody fusion from a lateral perspective (e.g., deliver a cutting tool for removing the disc material, actually removing the disc material, delivering an implant into the disc space, etc.).

In some embodiments, a guiding device may be placed on the back of the patient which performs a similar function to a rotating arm. In this embodiment the guiding device may include a curved tunnel, groove, tube or similar configuration with a radius of curvature substantially equal or at least based on the measurement from the center of the disc to the tip of the spinous process or other desired location there between. The guiding device is placed on the skin posteriorly so that the included curve guides the tool into the skin along an arc as determined by the radius previously measured. The tunnel portion of the guide can be adjusted to compensate for the individual patient. For example, if the patient is thin and without an additional fatty layer between the skin and the spinous process, the entry point may be directly lateral to the tip of the spinous process, and the radius of curvature will likely be the distance between the tip of the spinous process and the center of the disc If the patient has a substantial fatty layer then the entry point on the skin will be moved posterior from the disc space, and may also move medially as the fatty layer increases. This movement away from the disc (i.e., posteriorly and medially) requires an adjustment in the starting angle of the insertion tool such that the tool always follows the same arc determined by the central point located on the tip of the spinous process, or other desired starting reference point, as well as the radius determined by the distance to the center of the disc. The guiding device may be secured in place, such as to the operating table, after placement to reduce the risk of the guiding device changing position during the remainder of the procedure.

Another aspect of the present disclosure is directed to a cutting device (e.g., for use with a cannula as described herein) for clearing a disc space of a patient's vertebrae between vertebral endplates of the vertebrae as part of a spinal interbody fusion. Such a cutting device may include a straight or flexible drive shaft, and a retractable blade or blades at the distal end of the shaft. In some embodiments, the shaft may be cannulated. The one or more retractable blades may be operably coupled to an extension mechanism at a proximal end of the shaft (e.g., so as to be easily manipulated by the practitioner) that is configured to adjust an angle that the blade(s) extend from the distal end of the shaft relative to a longitudinal axis of the device. In other words, the extension mechanism may allow the blade to be selectively extended from the distal end of the device, at a desired angle thereto, so that upon rotation of the blade(s), a given radius (or diameter) cut or clearing action results. The blade may be operably coupled to an actuating mechanism that allows the practitioner to selectively rotate the blade (e.g., a quick connector or similar connection to a drill or other power source for rotating the shaft and/or blade(s)).

II. Exemplary Methods and Devices

FIG. 1 shows a cross-sectional scan through a torso portion of an exemplary patient's body 100, showing the various structures near the vertebrae 102 and disc 104 to be fused. Some of the illustrated structures include the muscles 106, 108, and 110 surrounding the vertebrae 102. Specifically, the muscles may include the erector spinae 106, the quadratus lumborum 108, and the psoas major 110 muscles. The scan also shows the colon 112. Although described principally in reference to the right side of the scan, it will be appreciated that an analogous posterior to lateral approach may be possible from the left side, with often symmetrical muscle and other structures present.

Figure 2A:
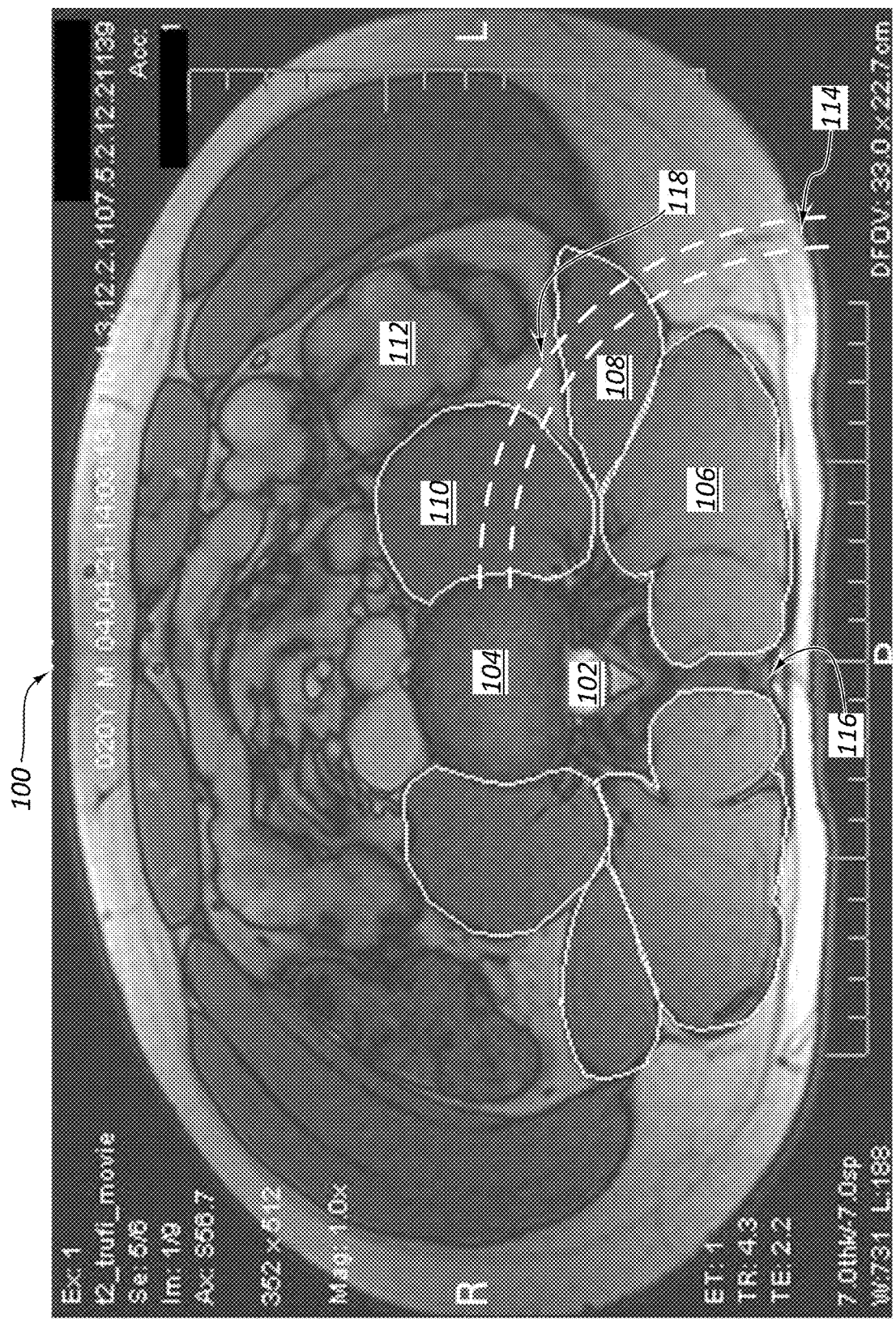
FIG. 2A shows the scan of FIG. 1, illustrating an exemplary posterior to lateral approach to the disc, reducing risks to adjacent structures as compared to a posterior approach, or a lateral approach.

FIG. 2A illustrates an exemplary posterior to lateral approach to the disc 104, overlaid on the scan of FIG. 1. As shown, the entry site 114 may be on a posterior surface of the patient's back at location that is laterally offset from a patient's spinous process 116. The path 118 to the disc 104 may begin as a posterior approach (perhaps most accurately, "posterolateral approach") relative to the disc 104, but as the path 118 advances, it may deviate from such approach towards a lateral approach. Therefore, when the path 118 reaches the disc 104, it may reach a lateral aspect of the disc 104.

While FIG. 2A shows the path 118 passing through the quadratus lumborum 108 and psoas major 110 muscles, while avoiding the colon 112, it will be appreciated that the posterior to lateral approach is not limited to passage through those specific muscles. Depending on the structure of the patient's back muscles and the type of tool used to access the disc 104, the path 118 may be through any of the three major back muscles surrounding the vertebrae 102. Those of skill in the art will also appreciate that a muscle's fibers, as living tissue, may be parted from one another, rather than cut, to allow relatively easy passage through the muscles. By avoiding cutting the muscles, the patient may recover significantly more quickly from the interbody fusion procedure. For example, it may be possible to perform such a procedure on an outpatient basis, with much faster recovery of the patient to normal activities.

Figure 2B:
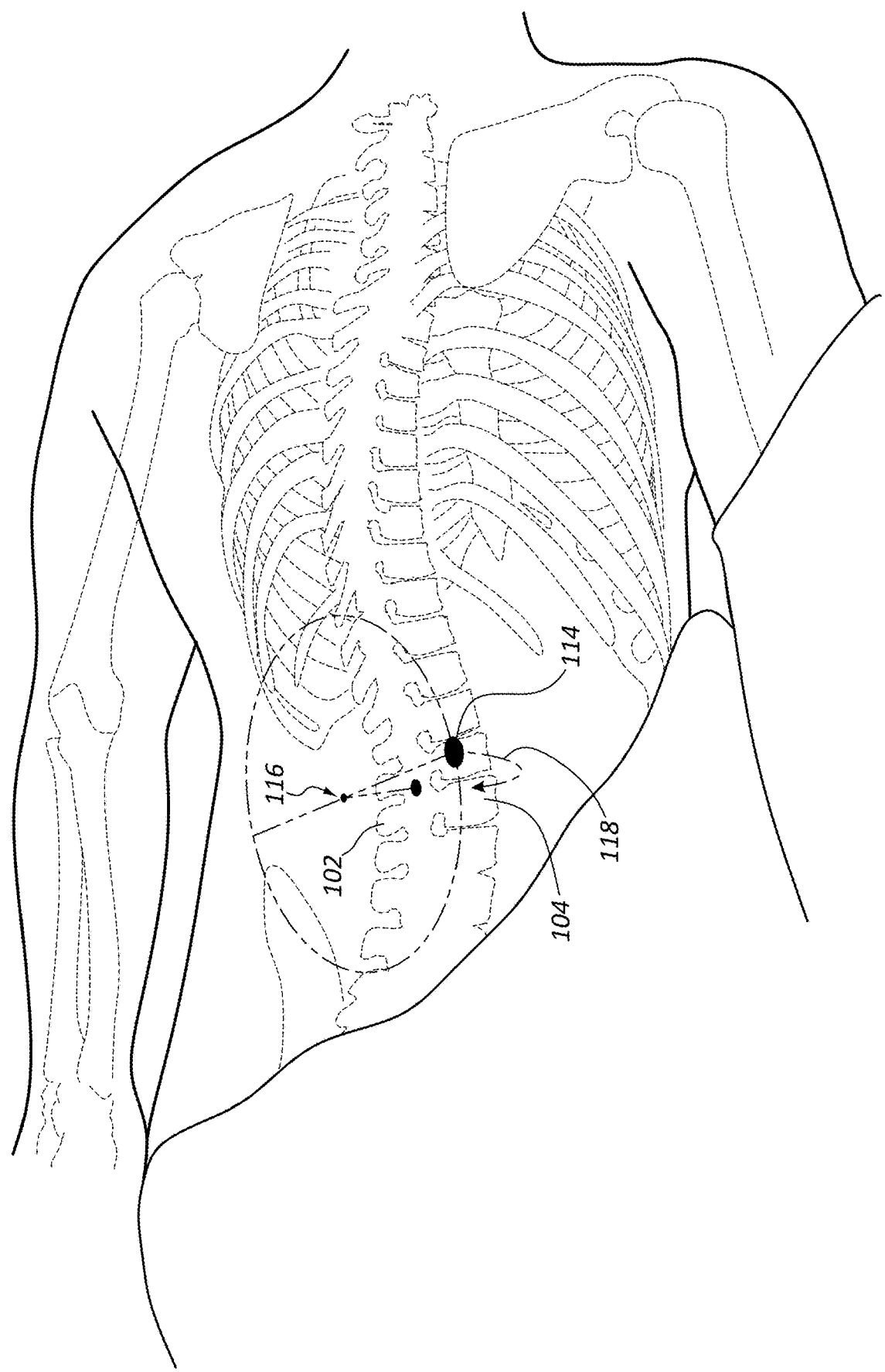
FIG. 2B is a perspective view of the torso of an exemplary patient, showing the pathway of an exemplary posterior to lateral approach to the disc.

The entry site 114 and path 118 are shown in a perspective view of the torso of an exemplary patient in FIG. 2B. As shown, the entry site 114 may be a location on the posterior surface of a patient's back that is laterally offset from a patient's spinous process 116. The path 118 to the disc 104 may initially be a posterior approach relative to the disc 104, but as the path 118 advances, it may deviate from a posterior approach towards a lateral approach. This allows the approach to avoid having to tunnel through or around the sensitive and delicate structures associated with the spinal canal, spinal cord, other nerves, and bone of the patient typically encountered in a posterior approach or traditional posterolateral approach. In addition, this approach reduces the dangers to the colon inherent in a strict lateral approach. Injuries to the lumbar plexus can be limited ty eliminating the need for additional retraction as is used in lateral approaches. The posterior to lateral approach which takes a non-linear route to the disc 104 advantageously traverses mostly, if not substantially entirely through muscle tissue. Such a route greatly minimizes risk to the sensitive organs and other structures of the patient, while also greatly minimizing damage to the patient that must be healed during recovery.

Figure 3A:
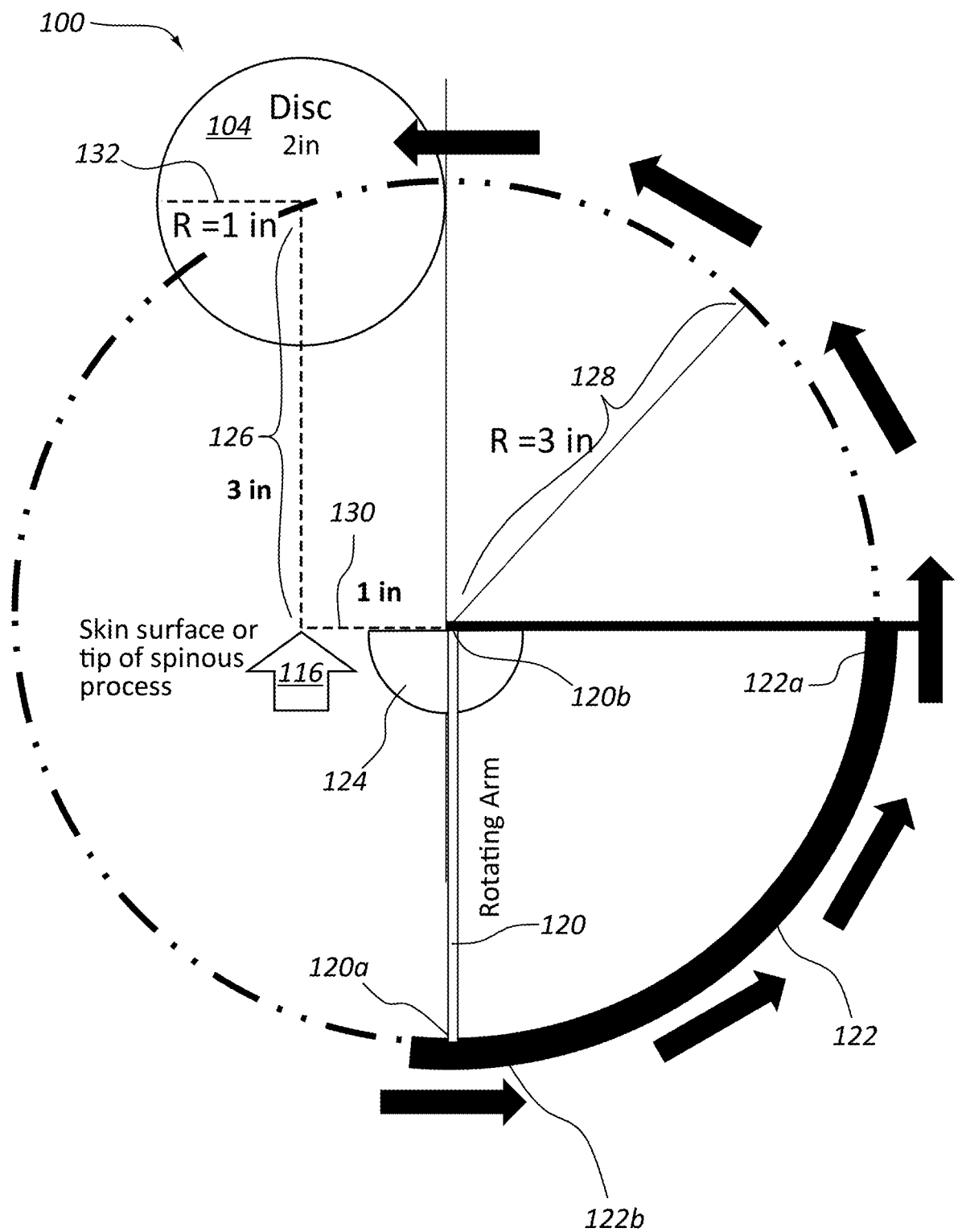
FIG. 3A schematically shows the initial stages of an exemplary posterior to lateral approach, e.g., using a rotating arm with a rigid tool having a fixed curvature attached at a distal end of the rotating arm, and another end of the rotating arm being secured at a location that is offset from the patient's spinous process, the distal end of the rotating arm being FIG. 3B schematically shows a more advanced stage of the posterior to lateral approach of FIG. 3A, with the leading end of the tool reaching the lateral aspect of the disc.
Figure 3B:
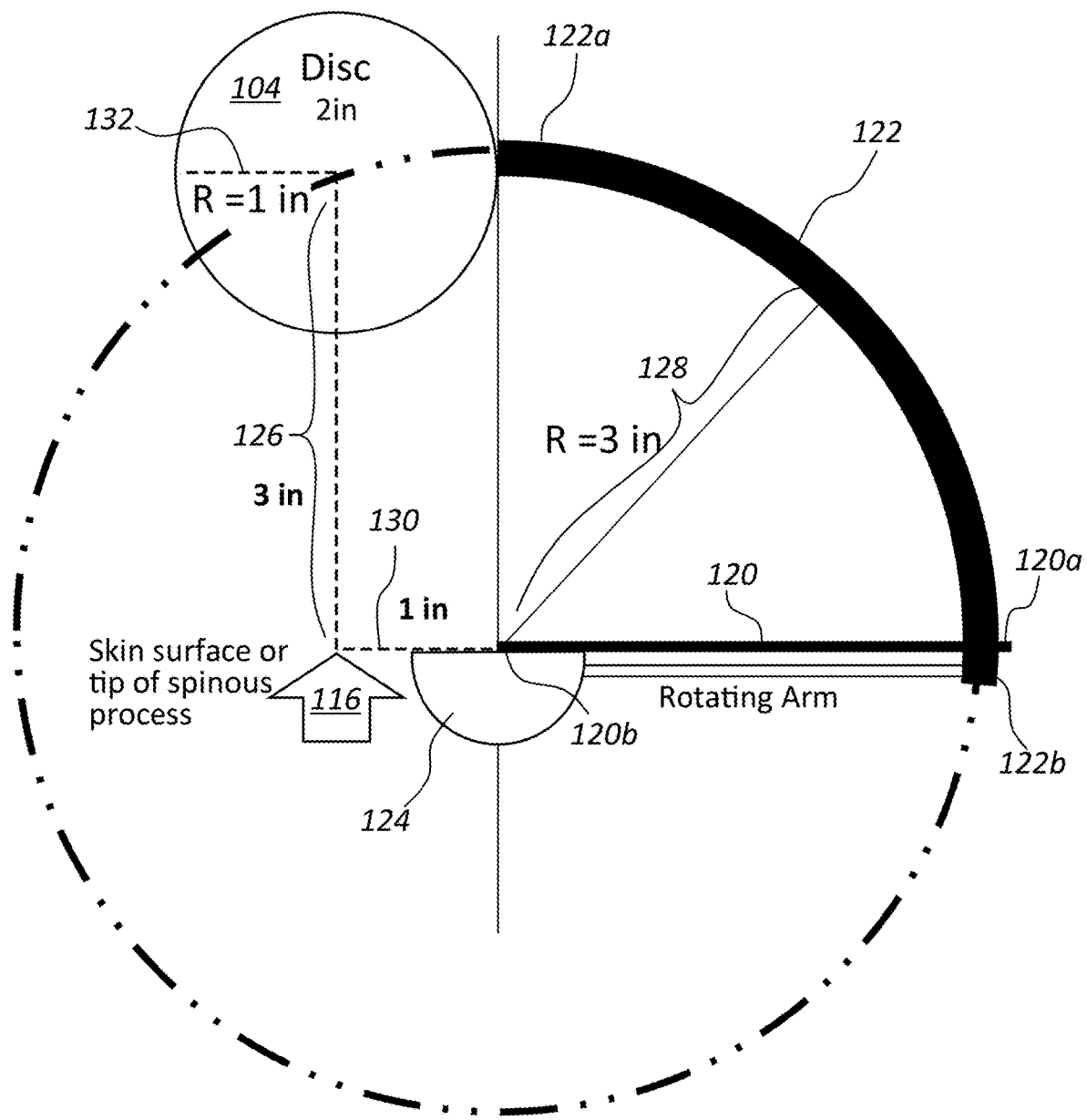
FIG. 3C schematically shows an alternative posterior to lateral approach, similar to that of FIGS. 3A-3B, but in which the end of the rotating arm is secured over the patient's spinous process, rather than being offset therefrom, so as to cause the leading end of the cannula to approach the lateral aspect of the disc somewhat differently than shown in FIG. 3B.

FIGS. 3A-3B illustrate an exemplary posterior to lateral approach using an arm 120 which may rotate and a tool 122 that may be rigid with a fixed curvature. The trailing end of the tool 122b may be attached at a distal end of the arm 120a, and the proximal end of the arm 120b may be secured to a guiding device 124 (which itself may rotate) at a location that may be laterally offset from the patient's spinous process 116. The location of the patient's spinous process may simply be observed by the practitioner on the patient's back, or determined based on a preoperative scan, or the like. As shown in FIGS. 3A-3B, the distance from the spinous process 116 to the center of disc 104 may be measured or otherwise determined from a preoperative scan (e.g., MRI or the like). That distance 126 may be used to determine the curvature of the tool 122 used in the procedure. The radius 128 of the arc made by the tool 122 may be substantially equal to the distance from the spinous process to the center of the disc 126. Deviations in the radius of curvature of the arc may be necessary, depending on the anatomical differences of individual patients.

However, rather than securing proximal end 120b of the arm 120 and guiding device 124 on the spinous process 116, in this embodiment, the proximal end 120b of the arm 120 and guiding device 124 may be offset from the spinous process 116 at a distance 130 substantially equal to or otherwise based on the radius 132 of the disc 104. The radius 132 of disc 104 may be determined from a preoperative scan. FIG. 3A shows how the leading end of the tool 122a may be set up at the entry site 114 on the surface of the patient's skin (i.e., the lateral aspect of the patient's back). FIG. 3B shows how the tool 122 may carefully be advanced through the skin to the lateral aspect of the disc 104 (e.g., passing through one or more of muscles 106, 108, 110 as seen in FIG. 2A). By offsetting the arm 120 at a location lateral to the midline or spinous process 116, when the leading end of the tool 122a reaches the disc 104, the leading end of the tool 122a may be in a truly lateral orientation relative to the lateral aspect of the disc 104. In other words, the leading end of the tool 122a is on the right (or left) side of the disc, reaching the most lateral aspect of the disc 104, in a true lateral orientation.

Figure 3C:
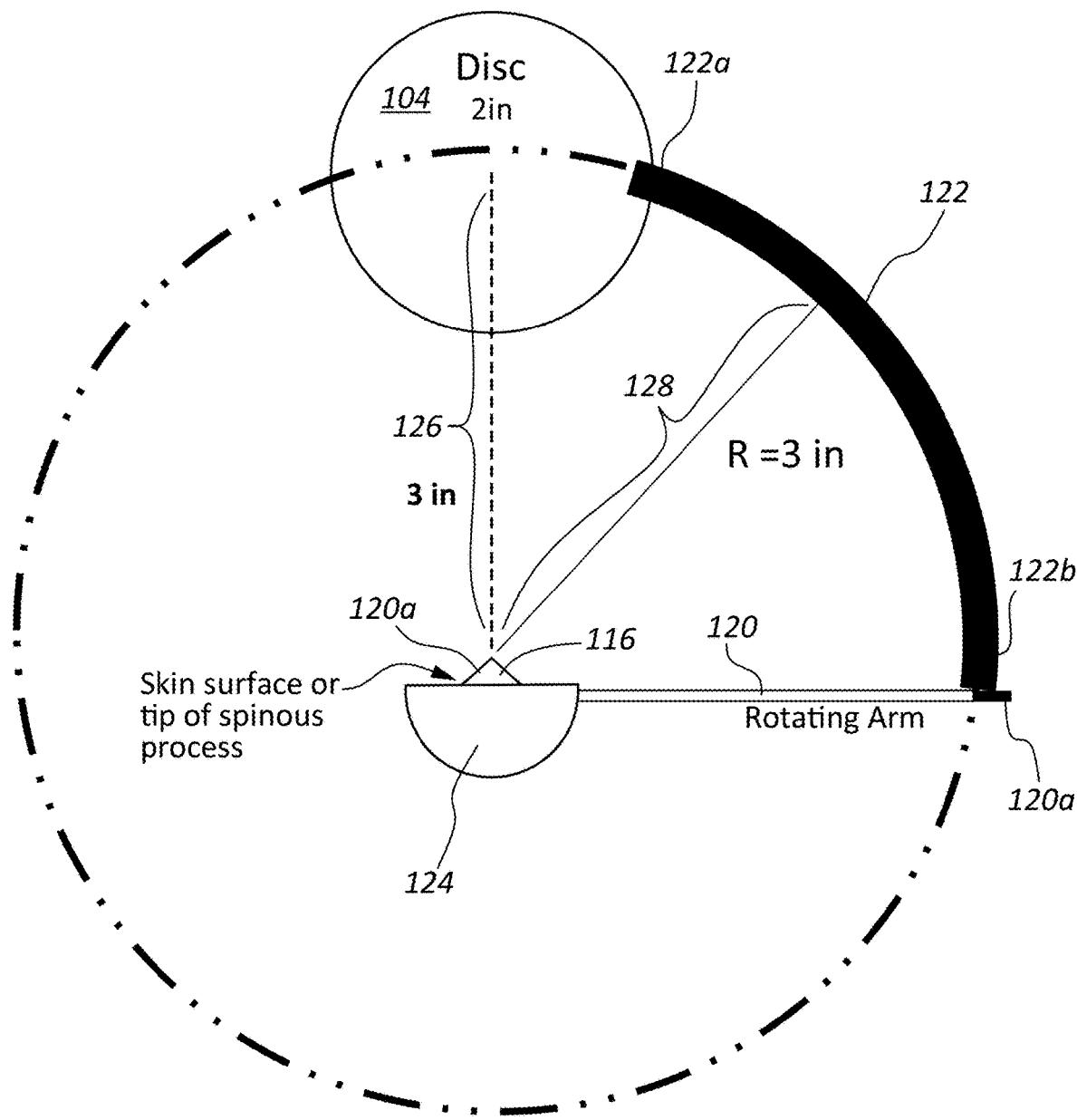

When using such an approach, care should be taken to ensure that sufficient space is always provided between the patient's colon 112 and the tool 122. An approach that may result in a substantially lateral approach to the disc 104, while providing even greater spacing relative to the colon may be preferred under certain circumstances. An example of such an approach is shown in FIG. 3C, where the proximal end 120b of arm 120 is not offset from midline 116. In addition, it will be apparent that by tightening the radius 128 of curvature associated with path 118, the risk to the colon 112 can be further minimized. Furthermore, the actual introduction and advancement of such a tool 122 may be performed while the practitioner observes the process on a real-time scan of the patient's anatomy, to decrease risk of injury to the colon. When deciding whether or not to laterally offset the proximal end of the arm 120b and guiding device 124, the amount of such offset, and the particular radius 128 to be employed, the surgeon may consult the preoperative scan to minimize any risk to the colon 112.

FIG. 3C schematically shows an alternative posterior to lateral approach, similar to that of FIGS. 3A-3B. Similar to the method shown in FIGS. 3A-3B, in FIG. 3C the distance 126 from the spinous process 116 to the center of disc 104 (or distance between any other selected point between the skin and the disc 104) may be measured from a preoperative scan. That distance 126 may be used to determine the curvature and length of the tool 122 used in the procedure. The radius 128 of the arc made by the tool 122 may be equal to or at least based the measured distance (e.g., distance from the tip of spinous process 116 to the center of the disc 104). However, unlike FIGS. 3A-3B, FIG. 3C shows a method in which the proximal end 120b of the rotating arm 120 and rotational device 124 may be secured over the patient's spinous process 116, rather than being offset therefrom. When the proximal end 120b of the arm 120 and guiding device 124 are secured over the spinous process 116, rather than being laterally offset therefrom, the tool 122 may not reach the most lateral aspect of the disc 104, although as shown, the approach still terminates in a substantially lateral approach It will also be apparent that the arc length of tool 122 in FIG. 3C may be shorter than that of 3B Devices to be placed through the tool 122, such as a cannula, and subsequently a cutting device, may advantageously be provided with a curvature similar to the curvature of the tool 122. Any implant inserted into the cleared disc space may also be advanced as needed along the curved geometry of tool 122. By not laterally offsetting the proximal end 120b of the arm 120 and guiding device 124, the risk to the patient's colon 112 may be further reduced. The practitioner may make adjustments as necessary to ensure that the entry to the disc space is as close to a true lateral approach as possible to minimize risk to surrounding structures. It may be desirable to pass a guidewire across the disc space before or after insertion of the tool. The guide wire can be placed through the insertion device, if cannulated, or through a cannula placed over the insertion tool. It would be advantageous if the guide wire is passed across the disc space in a lateral direction centered in the antero-posterior position where the guide wire travels fully across the disc space to provide a pathway for the subsequent cutting device or other tools.

If the patient's back is covered by a layer of fat thick enough to render the radius 128 of the arc made by the tool 122 too long so as to put the patient's colon 112 at risk as the tool 122 advances through the patient's back, then a small incision may be made posteriorly through the layer of fat to the depth of the spinous process 116 so that the tip of the spinous process, or other point located between the spinous process and the skin can still be used as a measuring point for the center of the rotational arc and to reduce the radius of the arc. Such may effectively recess the proximal end 120b of the arm 120 and/or guiding device 124 somewhat below the outer skin surface of the patient, so as to account for the relatively thick layer of fatty tissue over the spinous process 116. Such may reduce the radius 128 as compared to measuring from the surface of the skin, better avoiding the colon 112.

When comparing FIGS. 3A-3B with 3C, it will be noted that when the proximal end 120b of the arm 120 and device 124 are laterally offset (FIG. 3B), the tool 122 may be rotated several more degrees (and have a slightly longer length) in order to reach the lateral aspect of the disc 104. The arc length of the tool 122 used in the method shown in FIGS. 3A-3B may be at least equal to the value of $\pi r/2$, with r being the radius 128 of the arc made by the tool 122. In other words, the arc length may be equal or approximately equal to that defined by 90° of rotation along radius 128. It will also be noted that although the proximal end 120b of the rotating arm 120 and rotational device 124 are not offset in the method shown in FIG. 3C, the entry site 114 of the tool 122 remains laterally offset from the spinous process 116 (although the degree of lateral offset may be less). Although FIGS. 3A-3C show measurements, the measurements are merely exemplary of how a practitioner may perform the posterior to lateral approach using a rotating arm and a tool 122. Of course, actual measurements may differ, although the shown measurements may be relatively typical.

By way of further example, the disc diameter may be from about 1 inch to about 3 inches, or from about 1.5 inches to about 2.5 inches (e.g., about 2 inches). The distance from the center of the disc to be fused and the tip of the spinous process (as measured on a normal perpendicular plane as shown in FIG. 2B) may be from about 1.5 inches to about 5 inches, from about 2 inches to about 4 inches, or about 3 inches.

Figure 4A:
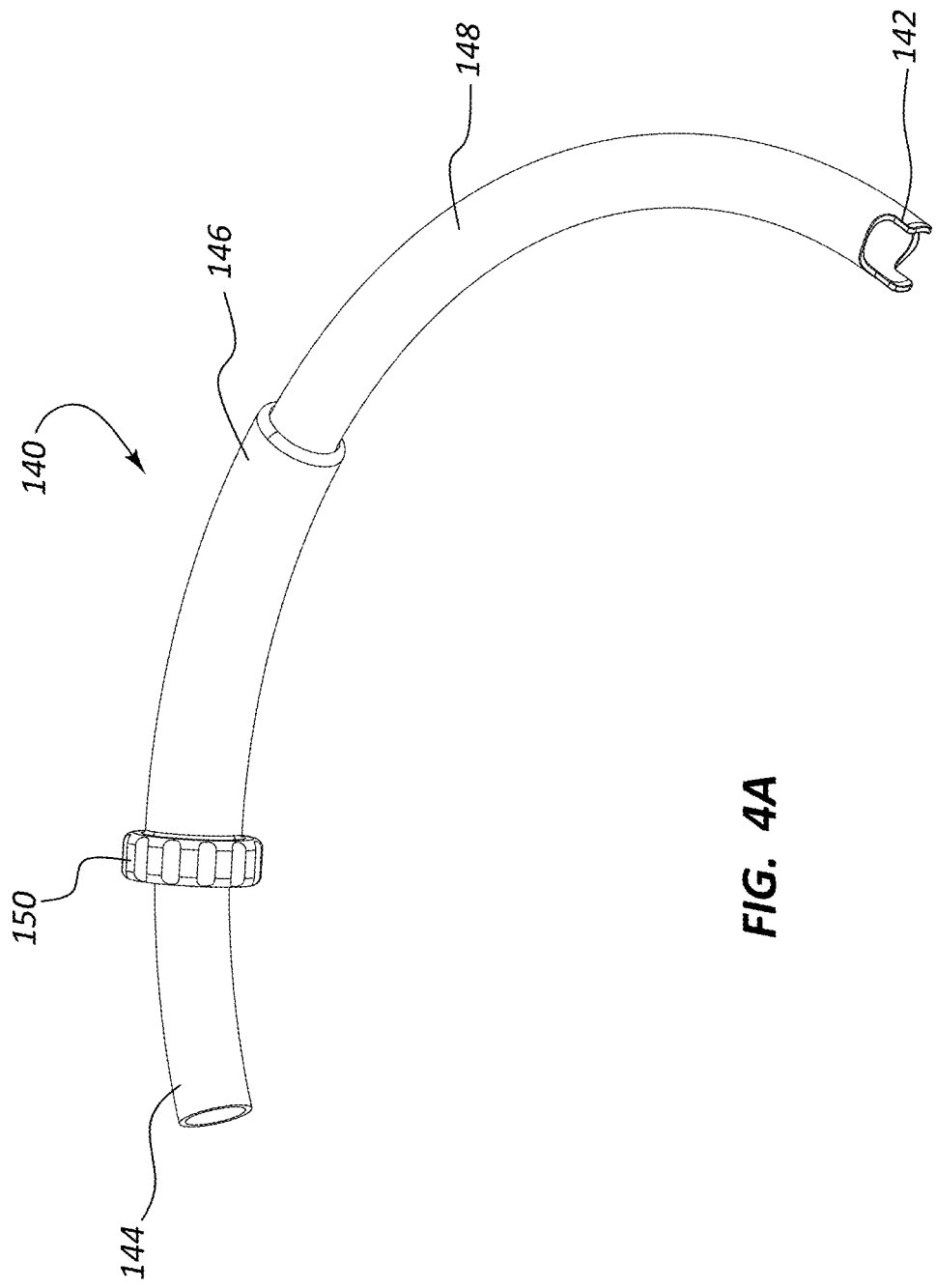
FIG. 4A is a perspective view of a rigid cannula having a fixed curvature, such as may be used to follow the pathway shown in FIGS. 2A-2B, or follow the pathway of the tool shown in FIGS. 3A-3C.

When employing the methods illustrated in FIGS. 3A-3C, once the tool 122 reaches the lateral side of the disc 104 the tool 122 may be securely docked thereto, and sequential dilators may be passed over the tool 122 until an appropriated sized cannula is docked to the lateral side of the disc 122. In some situations, the practitioner may push the tool 122 through the lateral wall of the disc into the central portion of the disc to secure the tool 122 in its position. As shown, the distal leading end of tool 122 may include spikes or other projections to aid in docking the tool to the lateral aspect of the disc. Furthermore, as described herein, a guide wire may be passed through disc 104, with the guide wire anchored at the opposite lateral end of the disc. In addition, the apparatus (e.g., tool 122, device 124, and the like) located outside the skin may be anchored to the table, after it has been properly positioned, to prevent movement during the remainder of the procedure. As shown FIG. 4A shows a rigid cannula 140 with a fixed curvature, having a distal leading end 142, a proximal end 144, an outer tubular shaft 146, an inner tubular shaft 148, and an attachment feature 150 for securing the cannula during use. As shown, the rigid cannula 140 may be used to follow the pathway 118 shown in FIGS. 2A-2B, or follow the pathway of the tool 122 shown in FIGS. 3A-3C. The rigid cannula 140 may be made from a variety of materials including metals, plastics, or other suitable biocompatible materials (e.g., titanium, a cobalt chromium alloy, or the like). The rigid cannula may include a flexible, or rotating section(s), that can be used to facilitate placement of the cannula in situations where the patient has a large fatty layer. In these situations, it may prove difficult to pass the cannula due to interference from the skin on the opposite side of the patient. The ability to bend or rotate the cannulate at some point along the cannula may help to prevent this issue.

FIGS. 12A-12E illustrate an embodiment similar to that shown in FIGS. 3A-4A, but in which the guiding device is fixed, and provides a curved tunnel, groove or similar pathway through which the tool 140 passes. For example, guiding device 124' may be placed on the back of the patient, and perform a similar function as the above described rotating arm 124. In this embodiment the guiding device 124' may include a curved tunnel, groove, tube or similar pathway 125 with a radius of curvature substantially equal or at least based on the measurement from the center of the disc 104 to the tip of the spinous process 116 or other desired location therebetween. The guiding device 124' is placed on the skin posteriorly so that the included curve guides the tool 140 into the skin along an arc as determined by the radius previously measured. The tunnel portion 125 of the guide 124' can be adjusted to compensate for the individual patient. For example, if the patient is thin and without an additional fatty layer between the skin and the spinous process, the entry point may be directly lateral to the tip of the spinous process 116, and the radius of curvature will likely be the distance between the tip of the spinous process 116 and the center of the disc 104. If the patient has a substantial fatty layer then the entry point on the skin may be moved posterior from the disc space, and may also move medially as the fatty layer increases. This movement away from the disc 104 (i.e., posteriorly and medially) requires an adjustment in the starting angle of the insertion tool 140 such that the tool always follows the same arc determined by the central point located on the tip of the spinous process 116, or other desired starting reference point, as well as the radius determined by the distance to the center of the disc 104. The guiding device 124' may be secured in place, such as to the operating table, after placement to reduce the risk of the guiding device changing position during the remainder of the procedure.

Figure 12B:
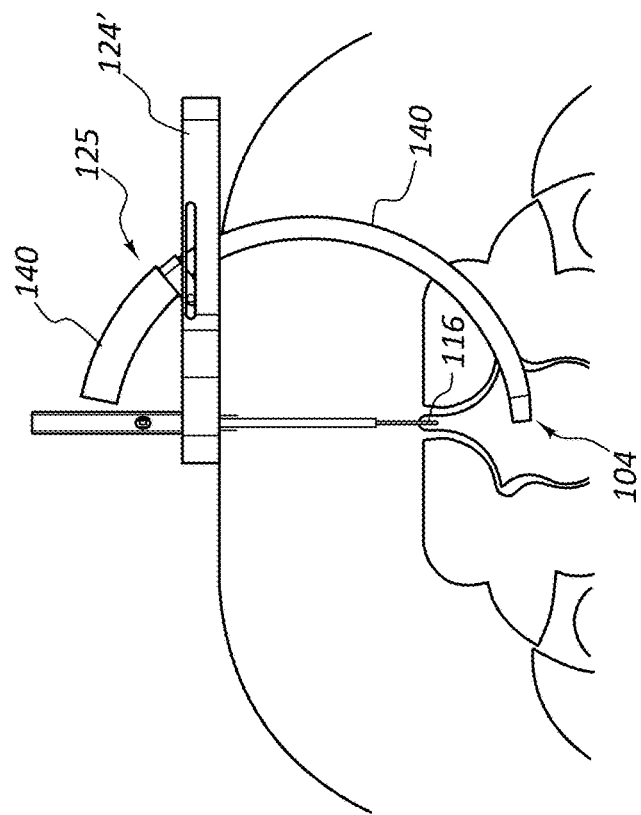
Figure 12A:
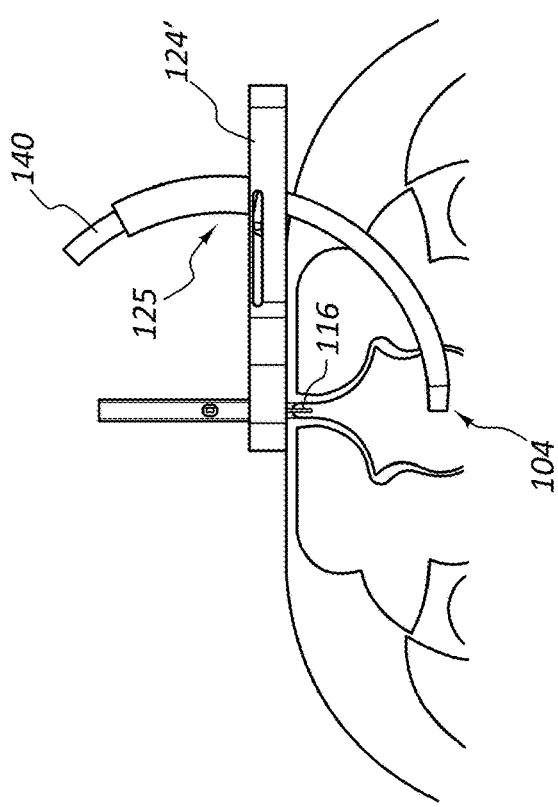
Figure 12C:
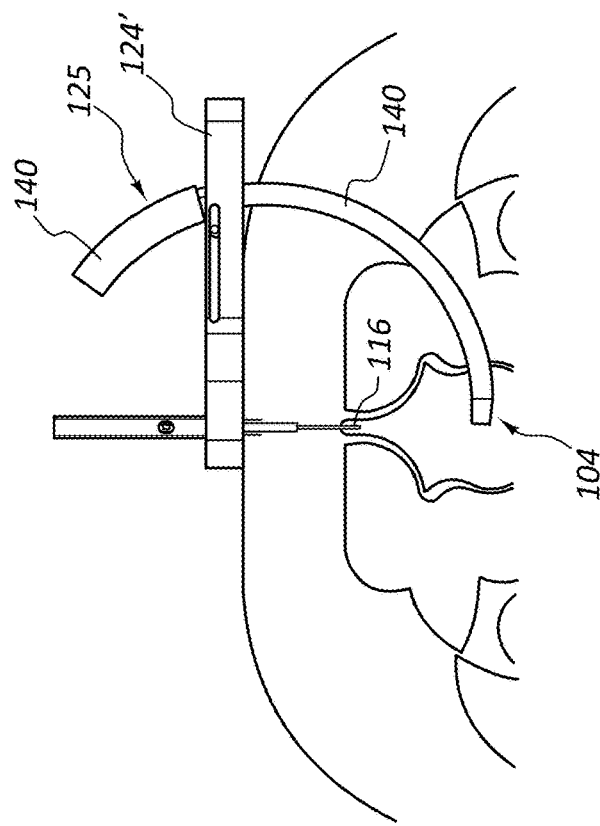
Figure 12D:
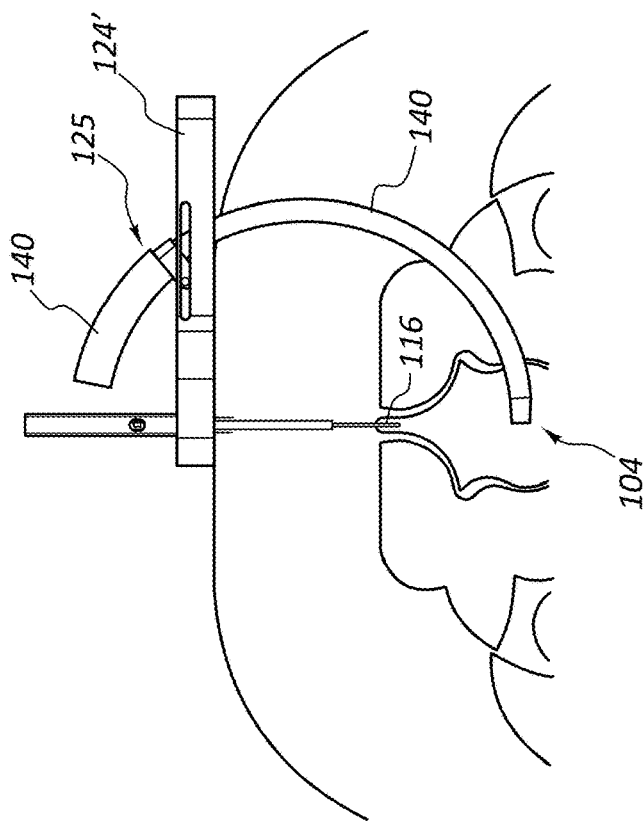
Figure 12E:
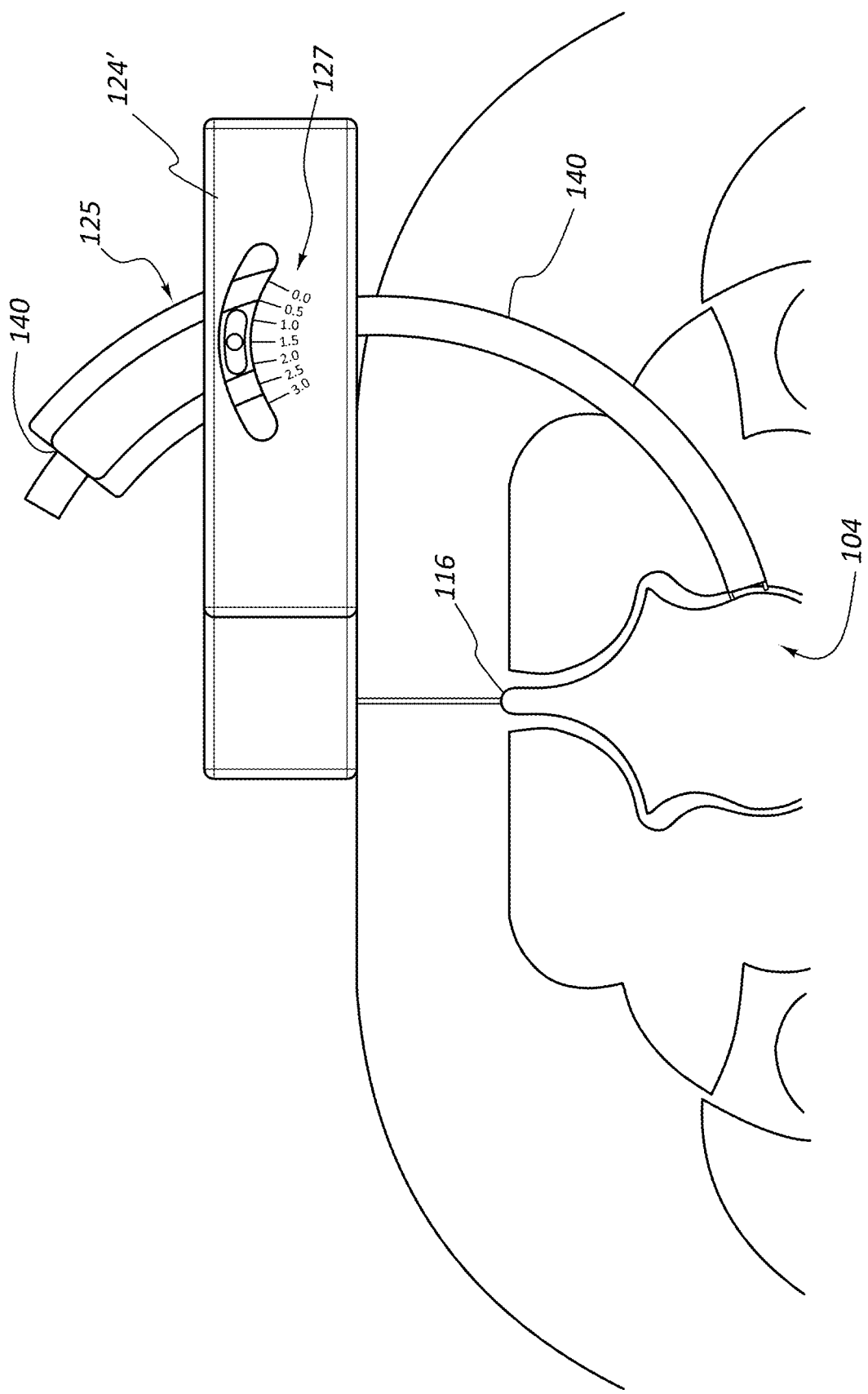

FIGS. 12A-12E show various settings for radius and angle, as may be selected by adjusting where tool 140 enters the tunnel 125 of guiding device 124'. For example, FIG. 12A illustrates a configuration that may be used where the measured distance (e.g., center of disc 104 to tip of spinous process 116) is 3 inches, with a 4 inch radius, and a selected 16° angle in tunnel 125. FIG. 12B illustrates a configuration that may be used where the measured distance (e.g., center of disc 104 to tip of spinous process 116) is 3 inches, with a 3.5 inch radius, the cannula tool 140 is centered, and a selected 32° angle in tunnel 125. In this illustrated configuration, the cannula radius may not be large enough to maintain the desired path. FIG. 12C illustrates a configuration that may be used where the measured distance (e.g., center of disc 104 to tip of spinous process 116) is 3 inches, with a 4 inch radius, the cannula is centered, and a selected 36° angle in tunnel 125. As compared to FIG. 12B, the cannula radius is now large enough to maintain the desired path. FIG. 12D illustrates another configuration that may be used where the measured distance (e.g., center of disc 104 to tip of spinous process 116) is 3 inches, with a 4 inch radius, and a selected 36° angle in tunnel 125. It will be apparent in FIG. 12D that the cannula tool 140 has been shifted laterally in tunnel 125 as compared to that of FIG. 12C (which otherwise includes similar settings). In this configuration, the cannula radius still clears the colon, but is far away from the medial axis. FIG. 12E shows a close up view of guiding device 124', illustrating how indicia 127 may be provided thereon for aiding the practitioner in selecting a desired radius, angle, or other setting. FIGS. 12B-12D show how the presence of a significant fatty layer may be dealt with, as compared to that of FIG. 12A, where no or only a minimal fatty layer may be present.

Figure 4B:
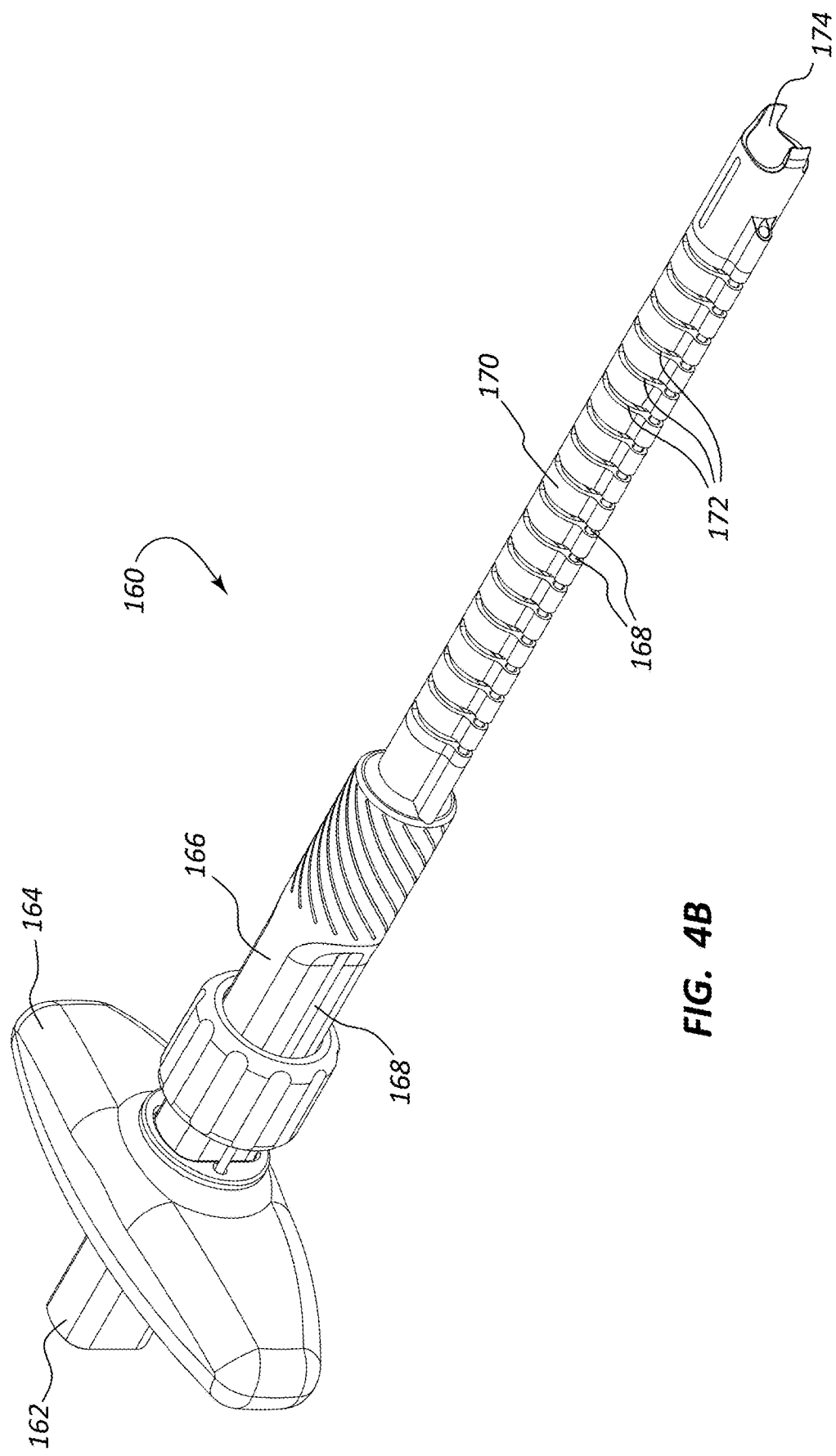
FIG. 4B is a perspective view of a flexible cannula, comprising a cable which can be selectively actuated to cause the cannula to assume a curved configuration, with the flexible cannula shown in its straight configuration.
Figure 4C:
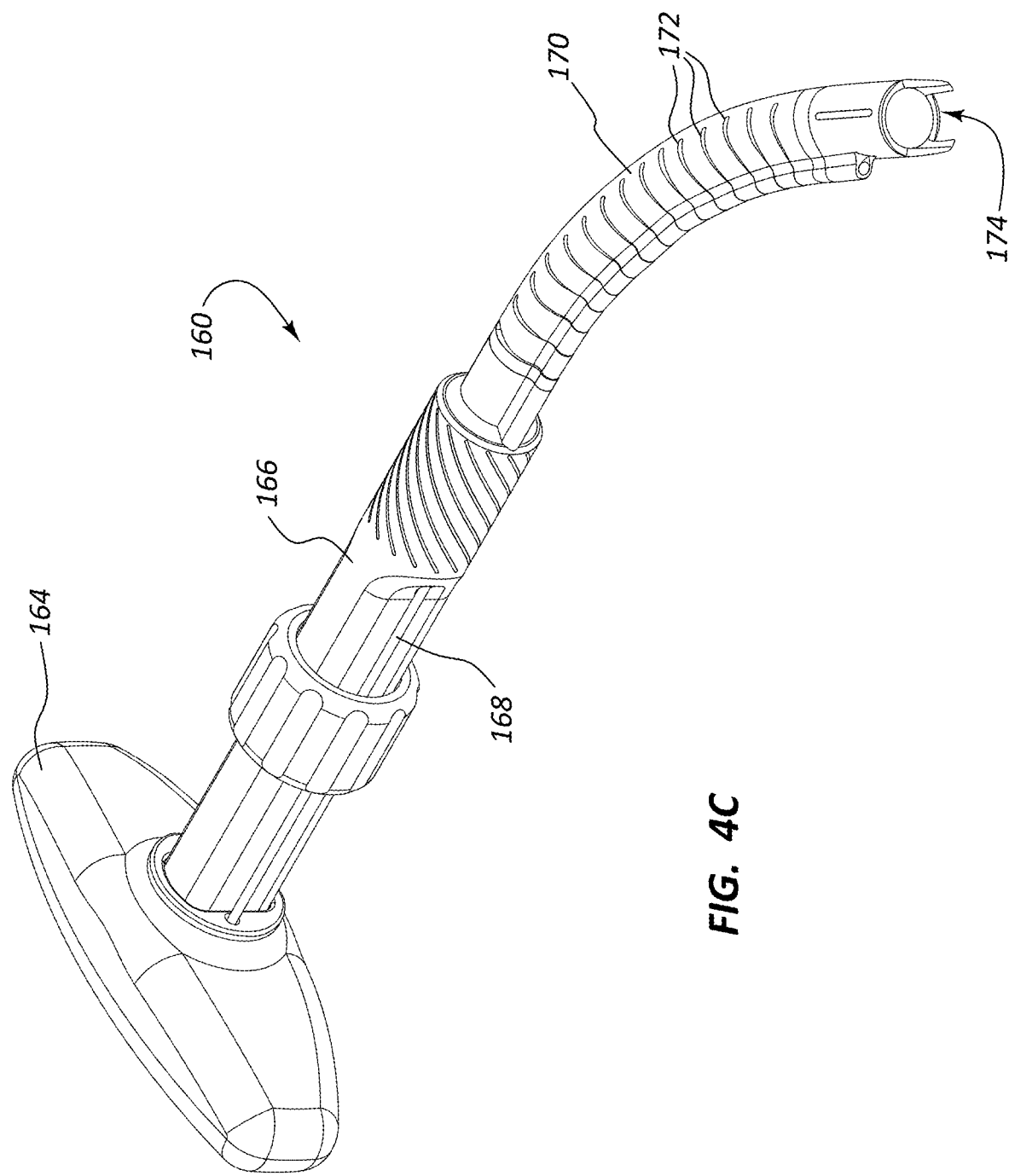
FIG. 4C is a perspective view of the flexible cannula of FIG. 4B, but with the flexible cannula shown in its curved configuration.

A flexible cannula 160 is shown in FIGS. 4B-4C, the flexible cannula 160 may include a proximal end 162, a handle 164, an outer tubular shaft 166, a cable 168, an inner tubular shaft 170 with slots 172, and a distal leading end 174. The cable 168 may be selectively actuated to cause the flexible cannula 160 to assume a curved configuration. FIG. 4B shows the flexible cannula 160 in its straight configuration, while FIG. 4C shows how the cable 168 may be actuated so the flexible cannula 160 assumes its curved configuration. The cable 168 may be actuated by the movement of the handle 164 longitudinally relative to the outer tubular shaft 166 toward the proximal end 162 of the flexible cannula 160 (i.e., pulling handle 164 back, proximally). This movement may cause the cable 168 to tension, closing slots 172 in the inner tubular shaft 170 as the cable is tensioned, and the inner tubular shaft 170 may then curve as shown.

Figure 5:
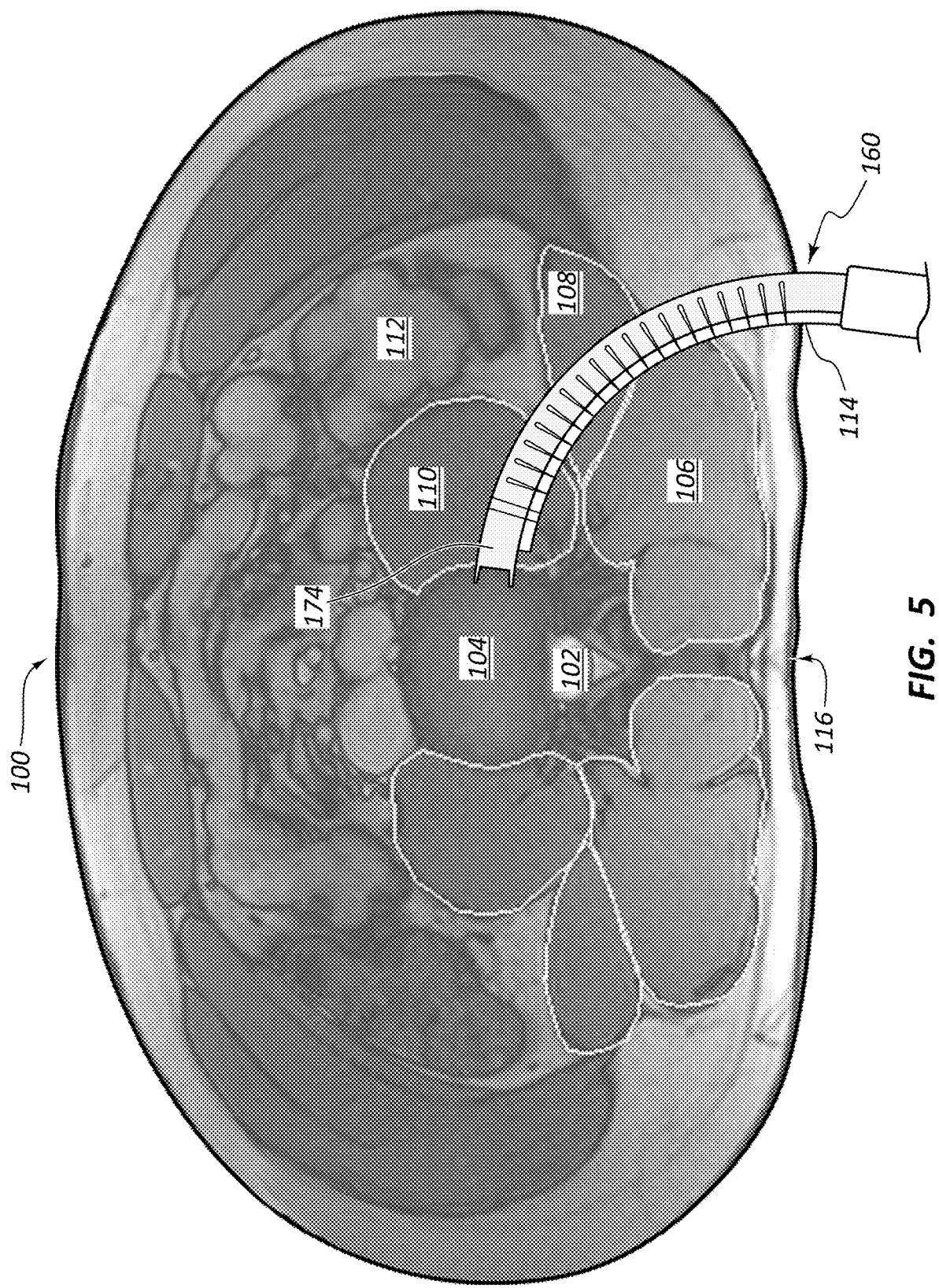
FIG. 5 shows a scan similar to that of FIG. 2A illustrating an exemplary pathway that a flexible cannula such as that of FIGS. 4B-4C may be advanced along.

FIG. 5 shows how a flexible cannula 160 such as that of FIGS. 4B-4C may be used to access the disc 104. The entry site 114 of the flexible cannula 160 may be on the posterior surface of the patient's back at a location that is laterally offset from a patient's spinous process 116. The flexible cannula 160 may be initially inserted in its straight configuration, as shown in FIG. 4B, and the initial approach of the flexible cannula 160 to the disc 104 may be a posterior or posterolateral approach relative to the disc 104. When the flexible cannula 160 is in the region of the patient's back about the psoas major 110 muscle, the cable 168 may be actuated so the flexible cannula 160 assumes its curved configuration, as shown in FIG. 4C. In its curved configuration, the approach of the flexible cannula 160 to the disc 104 may deviate from the posterior or posterolateral approach towards a lateral approach, and the distal leading end 174 of the flexible cannula 160 may attach to the lateral aspect of the disc 104 directly, or nearly directly, lateral (i.e., lateral or substantially lateral).

In some embodiments, the practitioner may place a flexible straight guide wire from a posterior position through the identified musculature, including the psoas muscle, until the guide wire reaches the lateral aspect of the disc. The guide wire may be passed through the lateral aspect of the disc into the center of the disc to secure the leading end of the guide wire. The flexible cannula 160 may then be passed over the guide wire, through the muscles, towards the lateral aspect of the disc 104. The flexible cannula 160 may be advanced until the leading end of the cannula approaches the lateral aspect of the disc, or even until the leading end touches or passes into the disc itself. At this point, or at any previous point along the path of insertion along the guidewire, the flexible cannula 160 can be made to assume a curved configuration, either in whole or in part The flexible cannula may displace the surrounding muscle tissue during this maneuver until the tip of the flexible cannula assumes its desired relationship to the disc directly laterally or substantially laterally. The guide wire may or may not be removed at this point. With the leading end of the cannula directed laterally, the guidewire can be advanced, directly laterally, or substantially laterally, across the disc space, to exit on the far lateral side. Preferentially, the guide wire should be placed equidistant from the front and back of the disc.

Figure 11A:
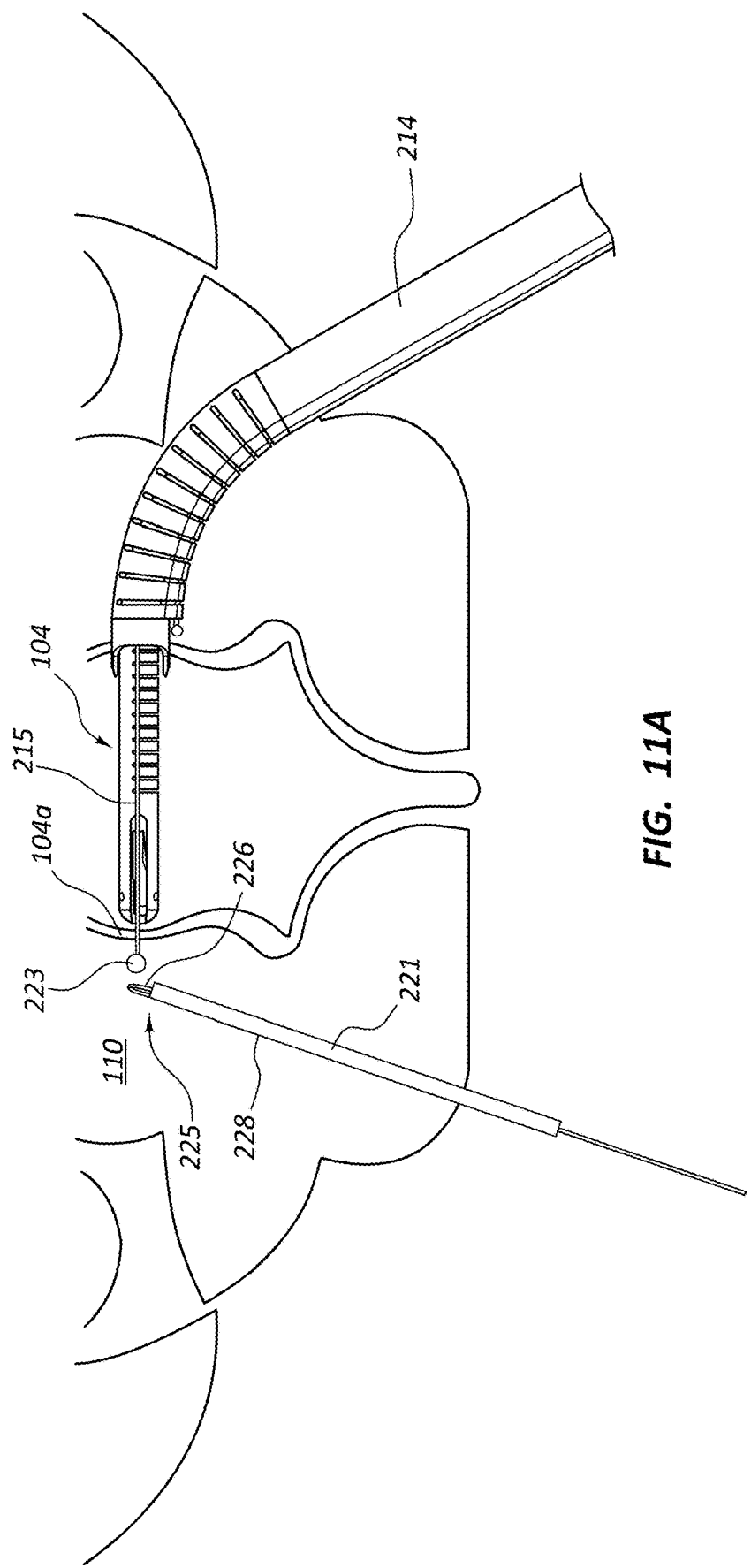
Figure 11B:
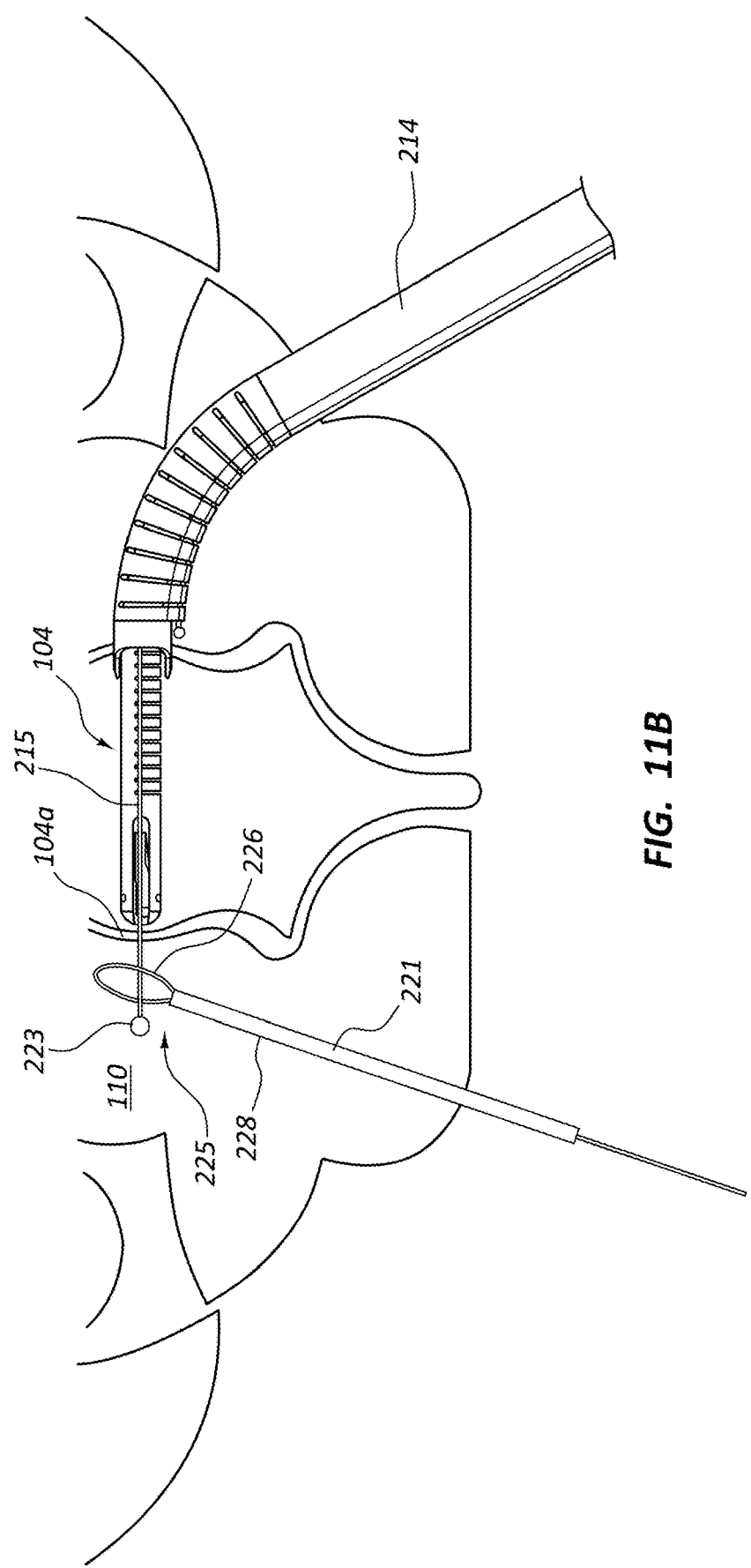
Figure 11C:
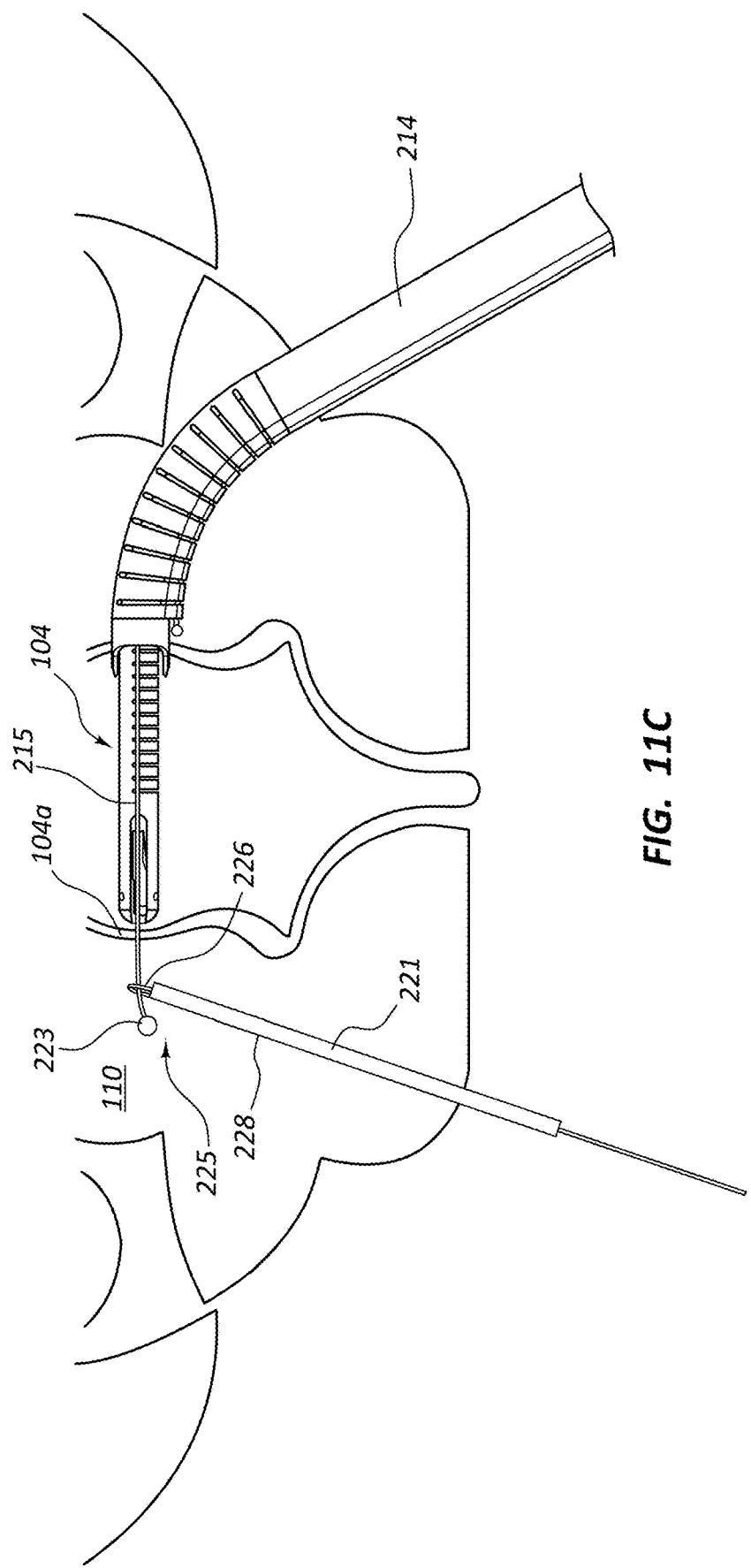

As shown in FIGS. 11A-11C, in order to more securely control the path of the cutting device, particularly while the device is actually cutting, the guide wire 215 may have a feature on the leading end which allows the leading end of the guide wire to be captured and secured. This feature may be as simple as a small sphere or other protrusion 223 on the leading end of the guide wire 215 or a similar feature. In order to secure the leading end of the guide wire it traverses the disc space 104 in a lateral orientation. The wire 215 is advanced such that a portion of the wire, including the leading end (with its capture feature 223) extends beyond the lateral confines of the disc 104 and the disc annulus 104a. In the lumbar spine, the tip of the end of the guide wire 215 may of necessity, extend into the psoas muscle for a distance sufficient to allow the wire to be captured.

The practitioner may then place a capturing tool 221 into the psoas muscle 110 on the same side of the leading end of the guide wire 215 from a posterior or posterolateral approach. The capturing tool 221 is advanced along a straight path until the leading end 225 of the capturing tool is near the location of the leading end of the guide wire 215. The leading end of the guide wire 215 is then captured and secured by the capture tool 221. In one embodiment, the capture tool 221 includes a loop 226 made from metal or other material that can be withdrawn into a containment sleeve 228. The loop 226 is extended out of the end of the containment sleeve 228 during capture, and the loop 226 expands upon extension into a circular, or other loop shape. This loop 226 then becomes a target through which the end of the guide wire 215 is passed (FIG. 11B) Once the end of the guide wire 215 has passed through the loop 226 (e.g., including the capture feature 223 on the end of the guide wire 215), the loop 226 is at least partially withdrawn back inside the containment sleeve 228 until the loop has effective captured and secured the end of the guide wire 215 (FIG. 11C). The capture tool 221 remains secured to stabilize the end of the guide wire 215, and prevent it from migrating, until the cutting process has been completed. Stabilizing the end of the guide wire in this or a similar manner may prevent the wire from migrating and keep the cutting device from deviating from a path desired by the practitioner.

The flexible cannula 160 may be made from any of a variety of materials including metals, such as stainless steel or suitable plastic materials, or other suitable biocompatible materials (e.g., stainless steel, titanium, a cobalt chromium alloy, or the like). Those of skill in the art will also appreciate that a variety of mechanisms could be used to effect the curvature other than a cable 168. For example, a shaft could also be used to push the flexible cannula 168 on the convex side of the shaft.

Figure 6C:
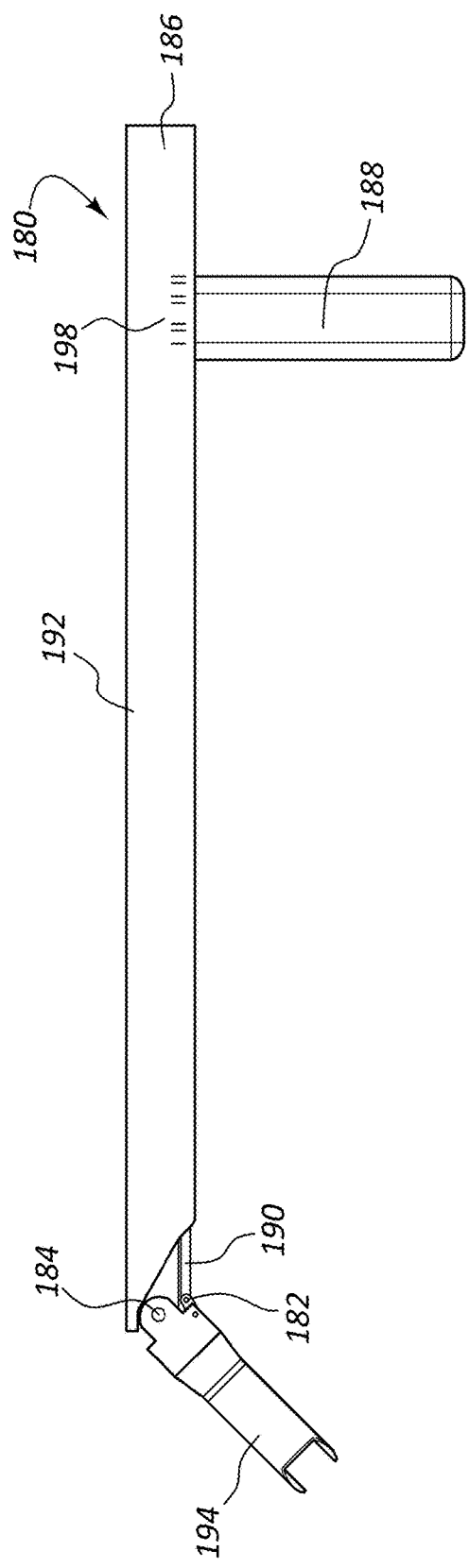
FIG. 6C is a perspective view of the hinged cannula of FIG. 6A, with the hinge shown in the angled configuration.
Figure 6D:
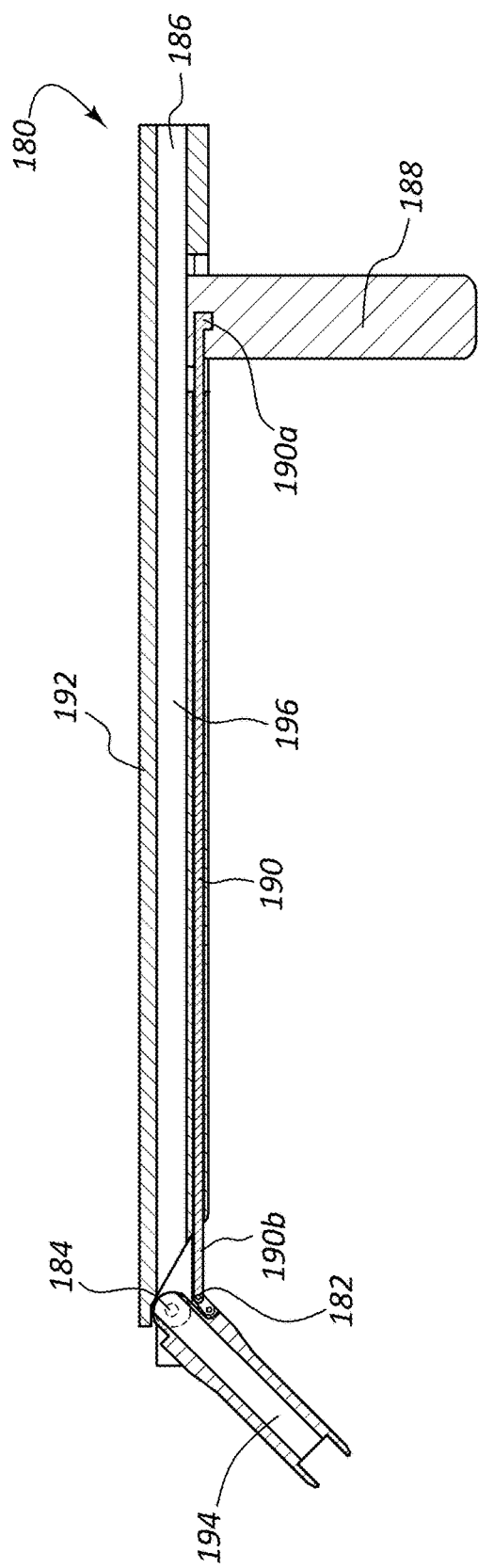
FIG. 6D is a cross-sectional view through the hinged cannula of FIG. 6C.

FIGS. 6A-6D show a hinged cannula 180 comprising mechanical linkage 182, with FIGS. 6A-6B showing the hinged cannula 180 with the joint 184 in the straight position, and FIGS. 6C-6D showing the hinged cannula 180 with the joint 184 in the angled configuration. As shown in FIGS. 6A-6D, the hinged cannula 180 may include a proximal end 186, a handle 188, an actuating rod 190, an outer tubular shaft 192, a mechanical linkage 182, a joint 184 (e.g., a pin hinge), and a distal leading end 194. Additionally, as FIGS. 6B and 6D show a cross-sectional view through the hinged cannula 190, an inner, hollow tubular shaft 196 is also shown. For the hinged cannula 180 to assume its angled configuration, as shown in FIGS. 6C-6D, the handle 188 may be slid longitudinally relative to the outer tubular shaft 192 toward the proximal end 186 of the hinged cannula 180. The handle 188 may be coupled to the proximal portion of the rod 190a, so movement of the handle 188 may also cause the rod 190 to move. The distal portion of the rod 190b may be coupled to the mechanical linkage 182, so movement of the handle 188, and thus the rod 190, would lead to the angulation of the mechanical linkage 182. The angulation of the mechanical linkage 182 may also cause the angulation of the joint 184, thereby making the hinged cannula 180 assume its angled configuration. The tubular outer shaft 192 may have guide notches 198 or other indicia near the handle 188, as shown in FIGS. 6A and 6C. Such notches or other indicia (e.g., markings) may aid the practitioner in knowing exactly what position the hinged distal leading end 194 is in, even without being able to physically see it.

Figure 7:
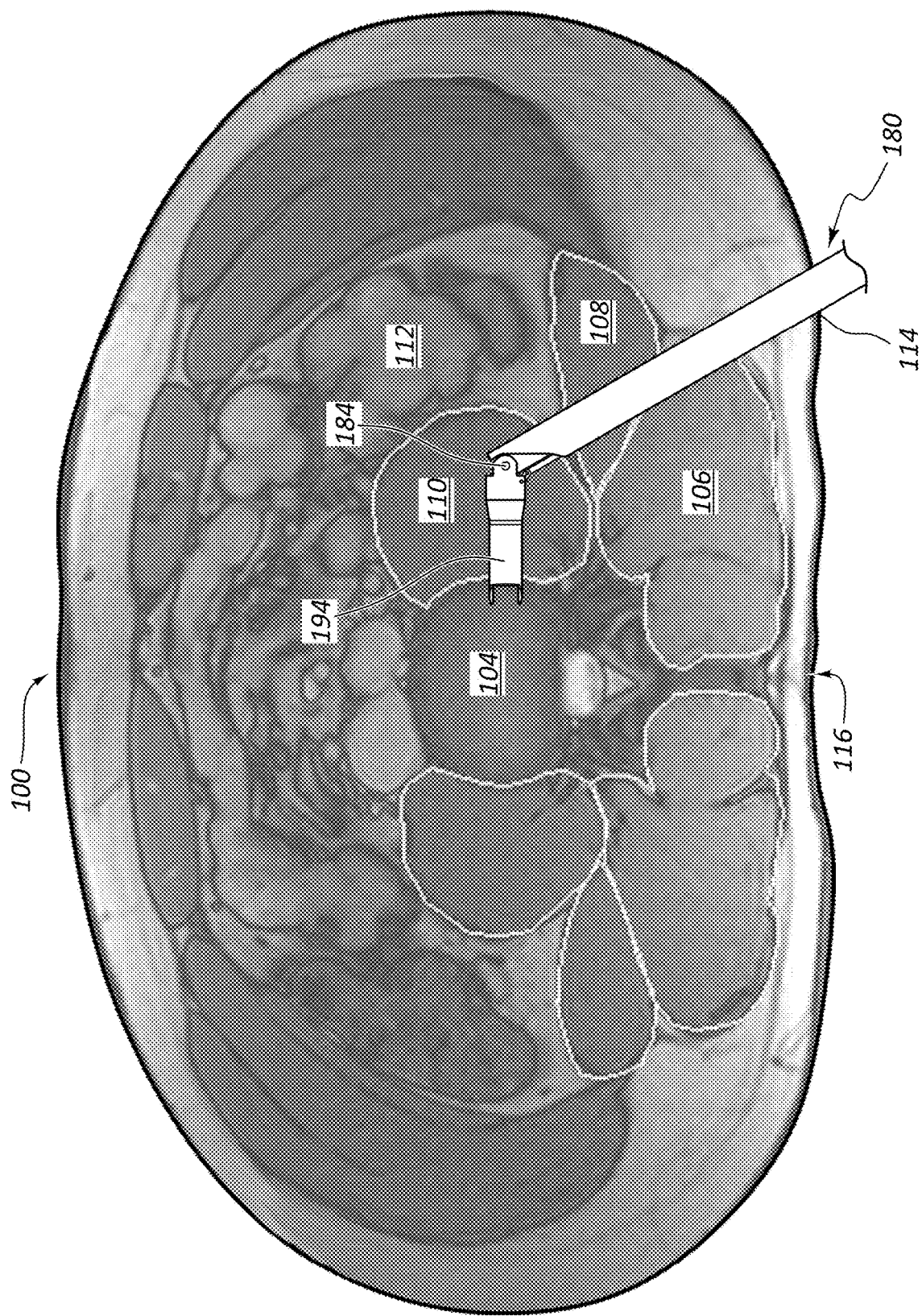
FIG. 7 shows a scan similar to that of FIG. 5, illustrating an exemplary pathway that a hinged cannula such as that of FIGS. 6A-6D may be advanced along.

FIG. 7 shows a scan similar to that of FIG. 5, illustrating an exemplary pathway that a hinged cannula 180 such as that of FIGS. 6A-6D may be advanced along. The entry site 114 of the hinged cannula 180 may be on the posterior surface of the patient's back at a location that is laterally offset from a patient's spinous process 116. The hinged cannula 180 may be initially inserted in its straight configuration, as shown in FIGS. 6A-6B, and the initial approach of the hinged cannula 180 to the disc 104 may be a posterior approach (although offset therefrom) relative to the disc 104. When the hinged cannula 180 is in the region of the patient's back about one or more of the erector spinae 106, quadratus lumborum 108, or psoas major 110 muscles, the mechanical linkage 182 and joint 184 may be angulated, so the hinged cannula 180 assumes its angled configuration, as shown in FIGS. 6C-6D. In its angled configuration, the hinged cannula's 180 approach to the disc 104 may deviate from the posterior approach towards a lateral approach, and the distal leading end 194 of the hinged cannula 180 may attach to the lateral aspect of the disc 104 directly, or nearly directly, lateral. Because the hinged cannula 180 is being advanced largely through only muscle tissue once actuation of the hinge mechanism may occur, the muscle tissue is typically easily parted, allowing passage even of the cannula 180 in its angulated configuration as seen in FIGS. 6C-6D. In other words, the muscle tissue may typically be parted, providing a pathway through which the leading distal end 194 of cannula 180, and non-linear portions of angled shaft 192 may be advanced, as needed. Such advancement may occur while observing progress of the cannula in real-time on a monitor (e.g., while watching a video feed of a scan or other image similar to that of FIGS. 1, 2A, and 7). The practitioner may find it beneficial to perform this procedure after the insertion of a flexible guide wire as previously described. The hinged cannula 180 may be advanced over the flexible guide wire if desired by the practitioner.

After successful attachment to the lateral aspect of the disc 104, it may be necessary to repeatedly change the hinged cannula 180 from the straight to angled form to allow instruments used for clearing the disc space to be inserted and used. Alternatively stated, it may be necessary to straighten out the hinged cannula 180 and pass a cutting tool past the pivot point 184 and then redirect the cutting device with the linkage so that it enters the disc 104 laterally. This same process may need to be repeated to remove the tool and insert any straight implants into the disc space. As with any of the processes described herein, this process may be performed with or without a flexible guide wire remaining in place. The hinged cannula 180 may be made from any of a variety of materials including metals, such as stainless steel, plastics or other biocompatible materials (e.g., stainless steel, titanium, a cobalt chromium alloy, or the like). Those of skill in the art will also appreciate that a variety of mechanisms could be used to effect the angulation other than illustrated rod 190.

Figure 8C:
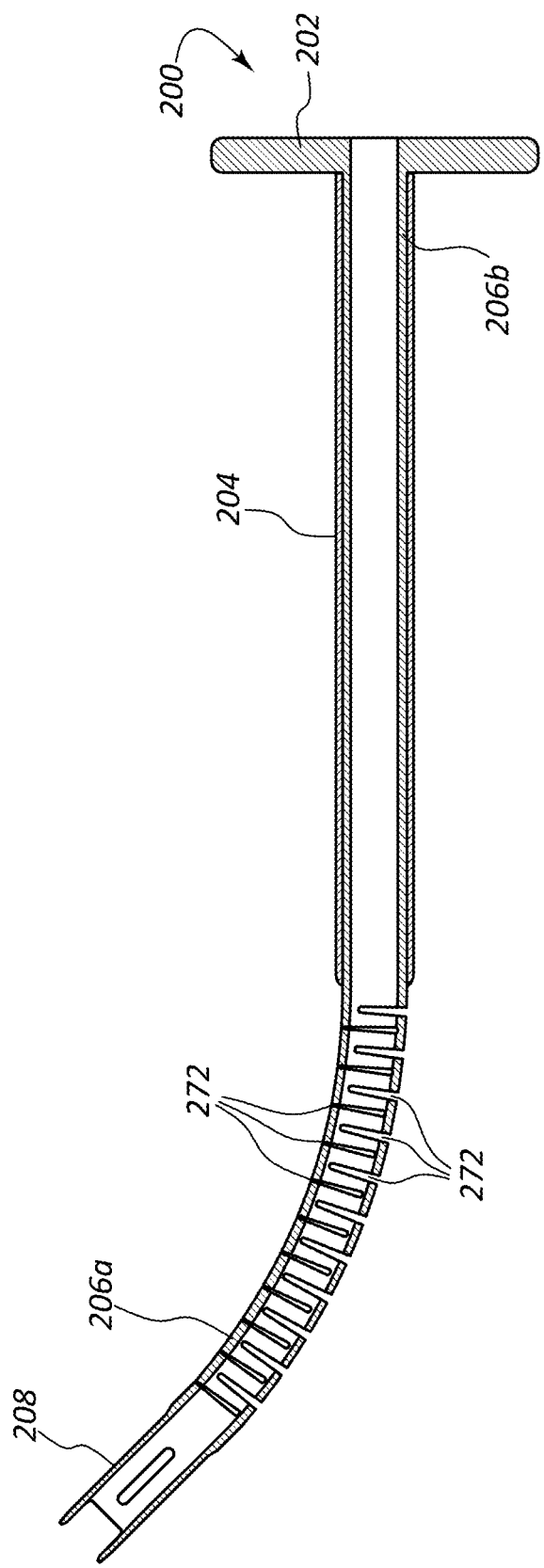
FIG. 8C is a cross-sectional view through the pre-stressed cannula of FIG. 8A.

FIGS. 8A-8C show an exemplary pre-stressed cannula 200, which may include a handle 202, an outer sleeve 204, an inner tubular shaff 206, and a leading distal end 208. As seen in FIG. 8C, the inner tubular shaft may include a portion that is pre-stressed 206a (i.e., to default to assume a curved configuration) and a portion that is not pre-stressed 206b. FIGS. 8A and 8C show how the outer sleeve 204 may initially be positioned over the pre-stressed portion 206a to hold the pre-stressed portion 206a in a straight configuration. FIG. 8B shows how the outer sleeve 204 may be retracted from over the pre-stressed portion 206a to the portion that is not pre-stressed by sliding the outer sleeve 204 longitudinally relative to the inner tubular shaft 206 toward the handle 202. When the pre-stressed portion 206a is no longer constrained by the outer sleeve 204, it can resume its default curved configuration. A plurality of slots 272 similar to slots 172 of FIGS. 4B-4C are also shown in portion 206a. Slots 272 are shown formed in both sides of portion 206a, although in some embodiments, they may only be present within one side. Their presence in both sides may allow portion 206a to be curved in the opposite direction, as will be appreciated, although the pre-stressing applied during manufacture may be such that the portion 206 defaults to curving to one side or the other, depending on selections made during manufacture. It is also anticipated that a rod, or other structure, could be placed on the inside or outside of a pre-stressed component, such that when the rod was removed, the pre-stressed component would assume its curved shape.

Although FIGS. 2A-7 show the disc being approached laterally from the right of the patient, those of skill in the art will appreciate that the posterior to lateral approach could also be performed so as to approach the disc laterally from the left of the patient.

FIG. 9A shows an exemplary cutting device 210 that may be used to clear the disc space in an interbody fusion procedure. As shown, the cutting device 210 may include a trigger mechanism 212, a drive shaft 214 in which at least a portion of the drive shaft is flexible, knobs 216, an inner shaft 218, and a blade 220. FIGS. 9B and 9C show a close up of the trigger mechanism 212 associated with blade 220 at the distal end 214a of the drive shaft, which may include a mechanism by which the angle of the blade 220 may be adjusted, by retracting, or extending the blade into a recess in distal end 214a of shaft 214. Control of the degree of such extension or retraction of blade 220 may be achieved through manipulation of structures 216, 218, and the like at proximal end 210b of device 210.

As seen in FIG. 9B, the extensions 222 of the trigger mechanism 212 are fully retracted within the distal end 210a of the cutting device, which may cause the blade 220 to be in a retracted position at the distal end 210a of the cutting device 210. The blade 220 may be in a retracted position when the surgeon initially places the cutting device 210 near or within the disc 104 (and as it is advanced thereto along the curved or other non-linear posterior to lateral pathways described above). Before the cutting device 210 is used to clear the disc material of disc 104, the surgeon may need to set longitudinal travel limits to ensure that the cutting device 210, when cutting, does not advance or retract beyond a designated safe area within the disc 104. Once this area of travel has been determined (e.g., by consulting a pre-operative scan or other real-time image) and locked for safety, the cutting device 210 can be rotated.

The inner shaft 218 may need to rotate with the blade 220 as the cutting device 210 is used. In its retracted position, the blade 220 may be parallel, or nearly parallel, to the longitudinal axis of the shaft 214 as shown in FIG. 9B. As the blade 220 is deployed, the angle between the blade 220 and the longitudinal axis of the distal end 210a of the cutting device 210 can be rotated.

The inner shaft 218 may need to rotate with the blade 220 as the cutting device 210 is used. In its retracted position, the blade 220 may be parallel, or nearly parallel, to the longitudinal axis of the shaft 214 as shown in FIG. 9B. As the blade 220 is deployed, the angle between the blade 220 and the longitudinal axis of the distal end 210a of the cutting device 210 may increase from the retracted position seen in FIG. 9B towards an extended position seen in FIG. 9C. In FIG. 9C, the blade 220 is shown extending approximately 90° in a sideways lateral direction from the distal ends 214a and 210a.

At some point, the blade 220 may make contact with the bony endplate of the vertebral body and encounter resistance, e.g., as the blade 220 is advanced longitudinally within disc space 104 from the lateral aspect seen in the various Figures towards the opposite lateral end of disc 104. The hardness of the endplate may subject the blade 220 to stresses which must be overcome by the cutting blade. For this reason, it may be advantageous to only deploy blade 220 while the device is rotating at a speed sufficient to provide momentum allowing the blade 220 to cut through the endplate without binding or breaking. As seen in FIG. 9C, the blade 220 is shown essentially perpendicular to the longitudinal axis of the cutting device 210 and/or distal end 214*a*. With the blade 220 angled as desired and rotating at an appropriate speed, the surgeon then advances at least blade 220 of the cutting device 210 forward or draws it backwards until the cutting device 210 has created removed a desired amount or volume of material within the disc 104 that is acceptable to the surgeon. Increasing the deployment of the blade 220 may increase the depth of the cut into the vertebral endplates. While shown with at or near 90° extension of blade 220, it will be appreciated that any angle between 1° and 90° (or even more than 90°) may be possible, through manipulation of one or more of structures 216, 218 of device 210. A full 90° extension of blade 220 results in a cylindrically shaped cut in disc 104 having the maximum diameter. Partial retraction to an intermediate angle (e.g., 10°, 20°, 30°, 40°, 45°, 50°, 60°, 70° or 80°, or over extension past 90° by such forgoing amounts will reduce the diameter of the resulting cylindrical cut The surgeon may elect to retract or partially close the blade 220 as he or she reaches the predetermined endpoints of travel for an increased margin of safety The cutting device 210 itself may contain some mechanism (e.g., a mechanical stop) that sets limits to the travel of the cutting device 210, such as safety pins, or an adjustable slot. While the term "blade 220" is principally used herein, it will be appreciated that the cutting device may include one or more blades The conscientious practitioner will wish to avoid the one or morecutting blades from cutting outside the safe confines of the disc space where they could create injury to the surrounding structures. For this reason, stops may be set to avoid traveling too far forward, and thus exiting the opposite side of the disc, as well as to avoid pulling the cutting device back into the cannula. These stops can be achieved in a variety of ways such as by adding pins which limit the travel of the cutting device. In FIG. 9A, stops could be placed onto a geared rail to accomplish this purpose, as shown in further detail in provisional application 62/382,007 filed Aug. 31, 2016. Other methods are easily considered, such as slots of a specified length that limit the travel of the cutting device. It would be most prudent for the practitioner to set the stops as desired prior to rotation of the cutting device 210.

Figure 10A:
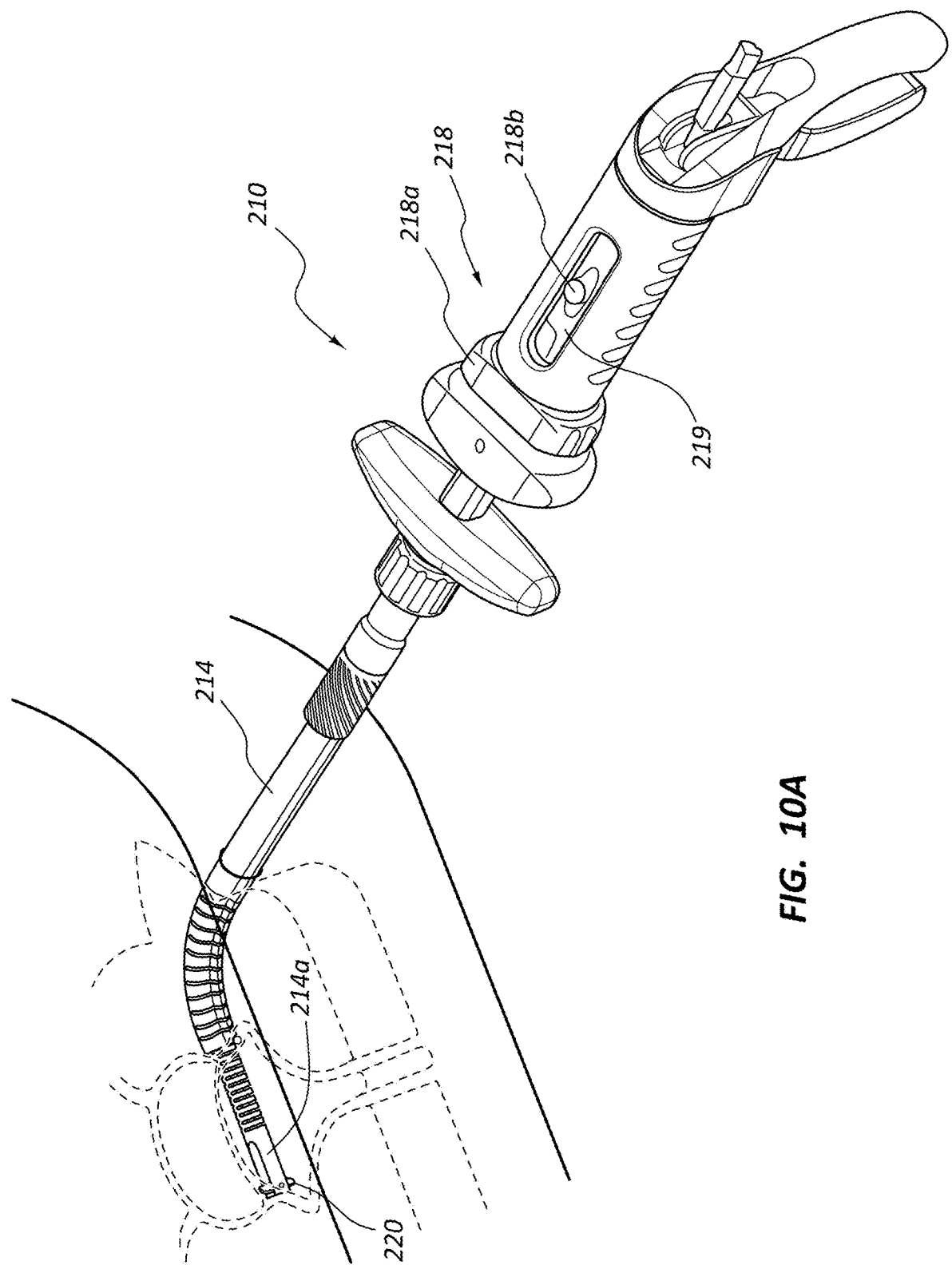
FIGS. 10A-10C show a cutting device with one or more blades and a cannulation which allows the cutting device to pass over a guide wire, further showing exemplary stop mechanisms to limit the travel of the blade(s) within the disc space. show various views of how a capture device may be used to stabilize the leading end of the guide wire in preparation for the cutting process. show various views of a method and device where a guiding device is placed over the patient's back, and the tool is guided through insertion and advancement from a posterior or posterolateral approach to a lateral approach.
Figure 10B:
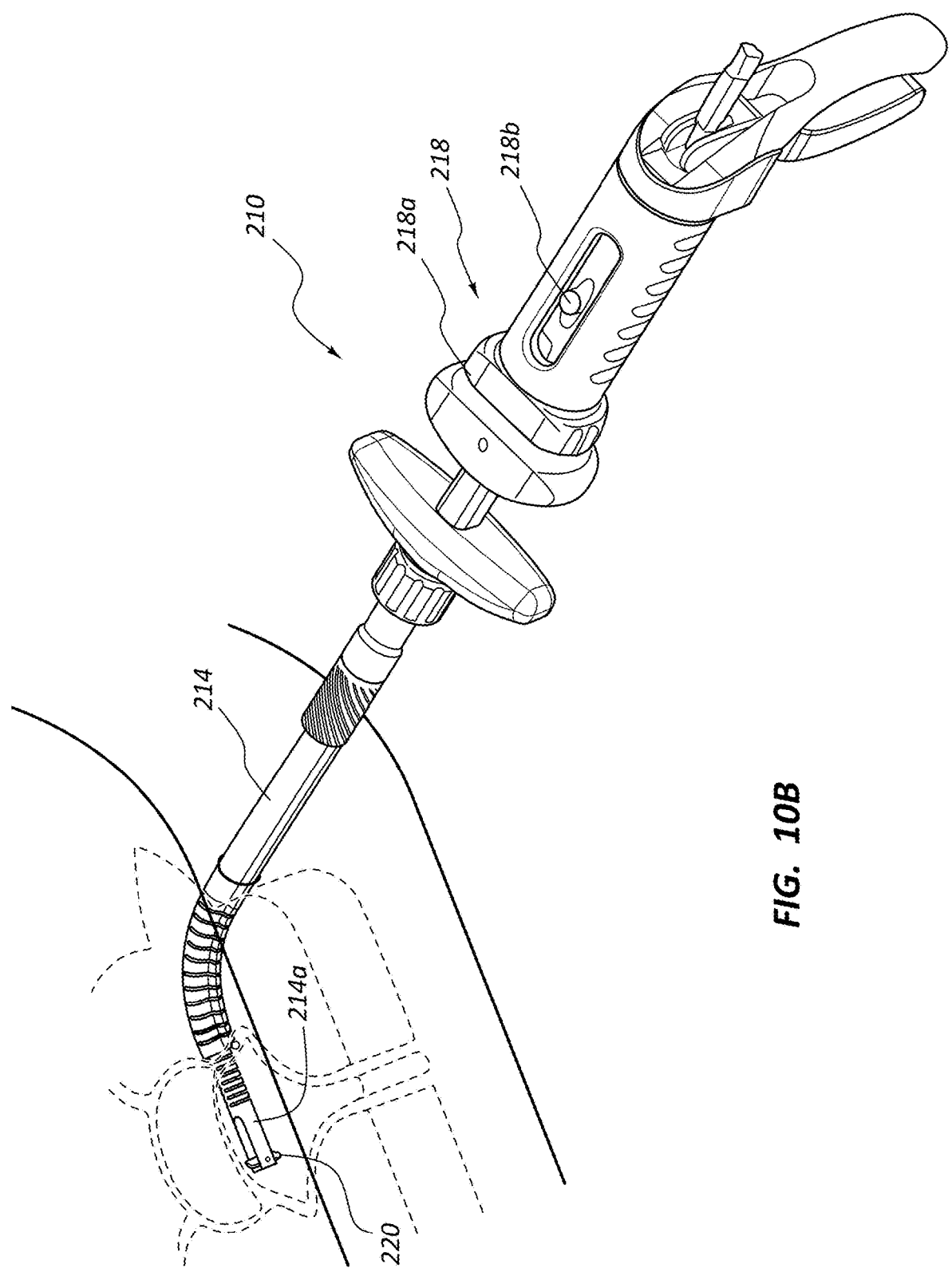
Figure 10C:
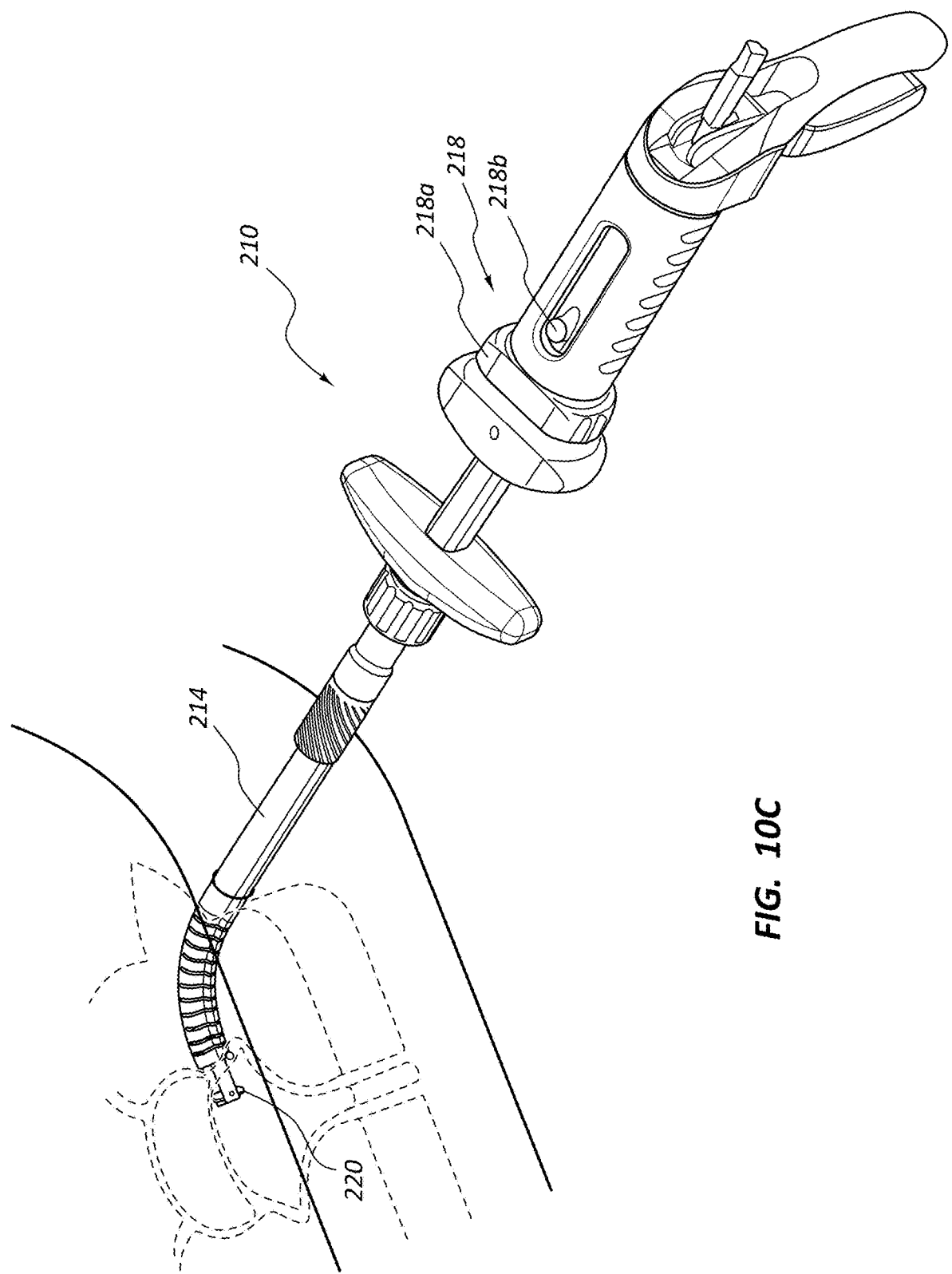

In FIGS. 10A-10C, another cutting device 210 is illustrated. Cutting device 210 may include one or more blades 220 for cutting, and one or more slots 219 for limiting the travel of the cutting device during its operation. The practitioner selects the appropriate length of the slot for cutting and then centers the slot within the disc space prior to cutting by manipulating a threaded depth adjustment or similar adjustment. For example, ring 218*a* may be rotated to shorten or lengthen the resulting cutting distance. Graduated length measurements may be provided on the shaft on which ring 218*a* threadably rotates up and down the underlying shaft. A pin 218*b* may be inserted to serve as a stop in conjunction with the illustrated slot to also aid in limiting the travel distance. FIGS. 10A-10C shows progression as the practitioner pulls the cutting device back from the far side of the disc space, towards the near side of the disc space (e.g., FIG. 10A shows where blade 220 is at the far side, FIG. 10C shows the entire cutting space having been traversed, and FIG. 10B is intermediate the two). As shown, in FIG. 10C, pin 218*b* is against the forward end of the slot, preventing further pull back without removal of the pin Further details of exemplary stop mechanisms are disclosed in provisional application 62/382,007 Filed Aug. 31, 2016, to which the present application claims priority.

The illustrated cutting device may be cannulated to work over a flexible guide wire. In this case, the guide wire may be first passed fully across the disc space unit the leading end of the guide wire exits the opposite lateral side of the disc space substantially equidistant from the front and back walls of the disc. The guide wire may remain in this position while the cutting process proceeds. The guide wire helps to maintain the cutting device centered in the disc space while the cutting is accomplished. FIGS. 11A-11C illustrate use of such a guide wire. The slots help to prevent the practitioner from advancing the cutting device past the confines of the disc and from pulling the cutting device into the cannula while cutting. To further reduce the risk of the cutting device deviating from the desired cutting zone, it is suggested that cutting be accomplished only while the practitioner is pulling the cutting device back through the disc, rather than pushing the device forward.

Those of skill in the art will appreciate that a variety of methods may be used to deploy the blade 220 other than the illustrated mechanism, including a rotating knob on a threaded sleeve, such as a trigger mechanism shown in FIGS. 10A-10C. Other mechanisms will be apparent to those of skill in the art in light of the present disclosure. The rotation of the cutting device 210 may be done by hand, or more typically with the assistance of a power source. The rotation of the cutting device 210 will typically occur at higher speeds than cannot normally be accomplished by hand A standard drill head, commonly found in the operating room would be sufficient for the procedure. The cutting device 210 may attach to the drill head or other rotational source via a Vi inch quick connector 222 (FIG. 9A), or similar connection. Increasing the RPM of the cutting device 210 may improve the effectiveness of the blade 220 by using the momentum of the system to cut through the disc material, cartilage and bone.

Once the blade 220 has cut through the disc material and endplates to the satisfaction of the surgeon, the cutting device 210 may be removed. The blade 220 may be restored to its retracted position on the distal end 210*a* of the cutting device 210. Once the blade 220 has been retracted, the cutting device 210 may be withdrawn.

The cutting device 220 may contain one or more blades. The blades may be designed to function with cutting or grinding action, or both. The blades may be manufactured from a high strength material such as stainless steel, or other materials such as carbon fiber, other metals, suitable plastics, or other biocompatible materials (e.g., titanium, a cobalt chromium alloy or the like). The cutting blades may be changed or replaced easily, as needed.

Although cutting device 210 is described in the context of the posterior to lateral approach for an interbody fusion, those of skill in the art will appreciate that the cutting device 210 could be used to clear the disc space after another method was employed to access the disc 104 (e.g., a lateral approach technique).

Figure 13:
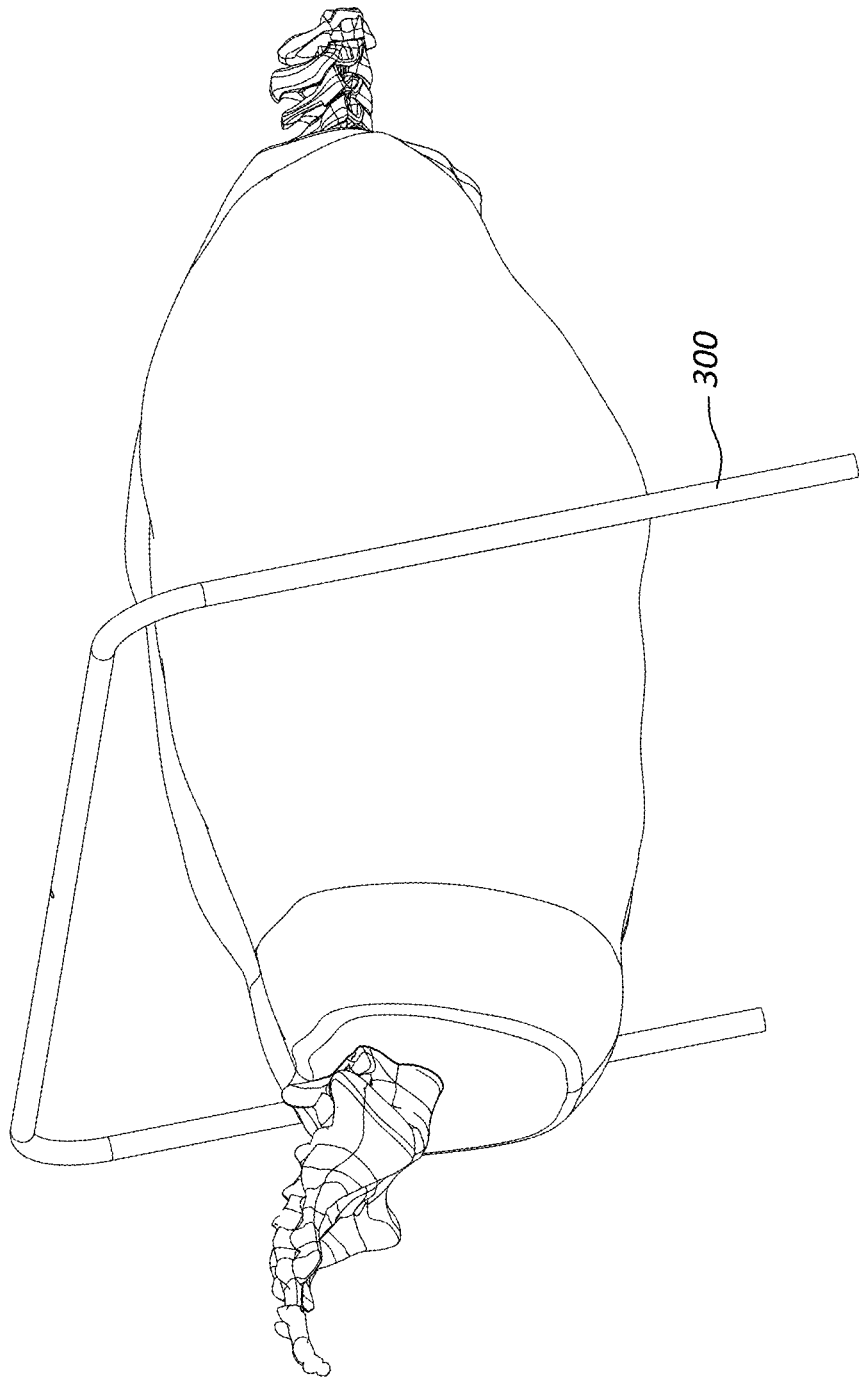
FIGS. 13-35 illustrate progressive steps of an exemplary procedure.
Figure 14:
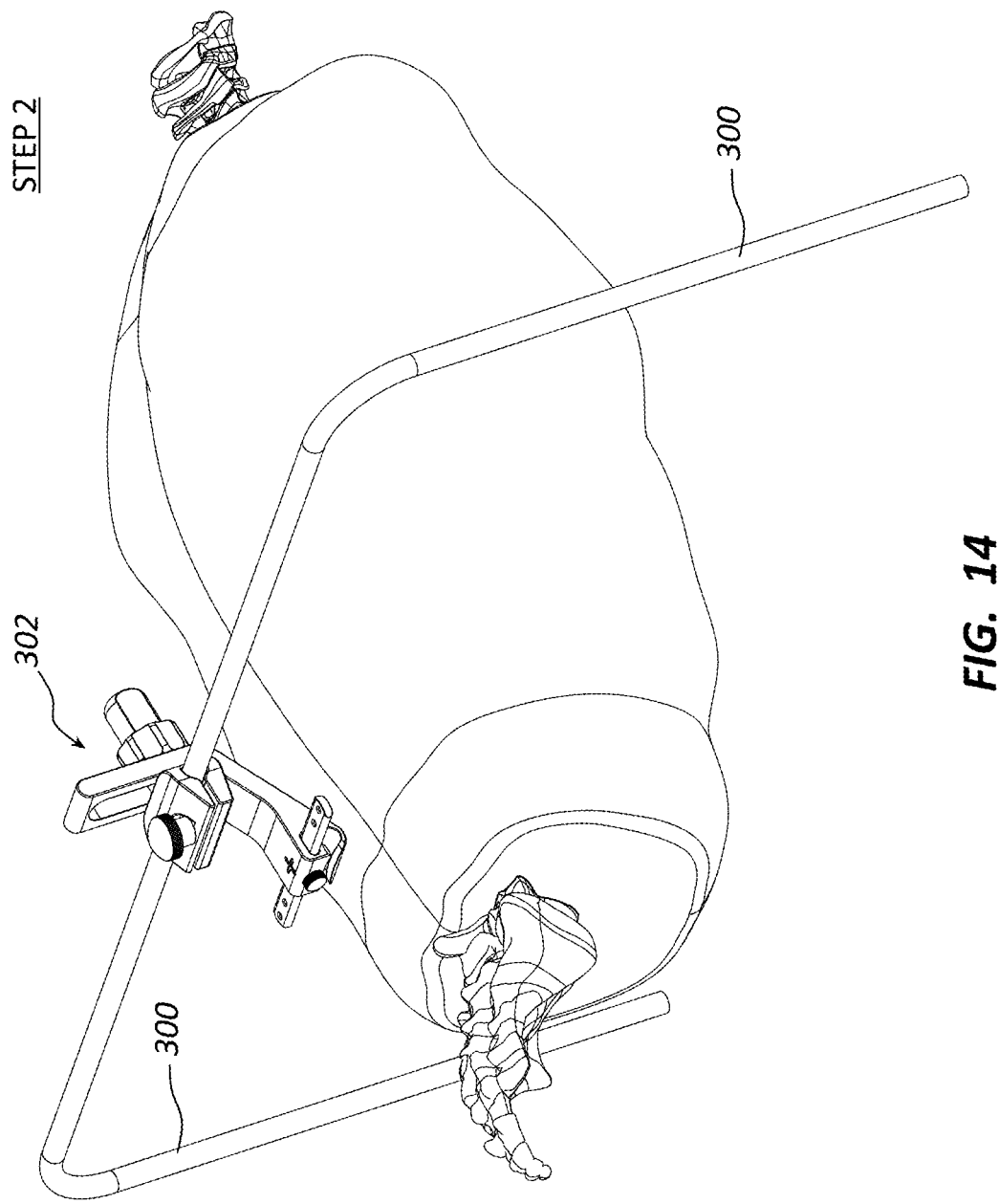
Figure 15:
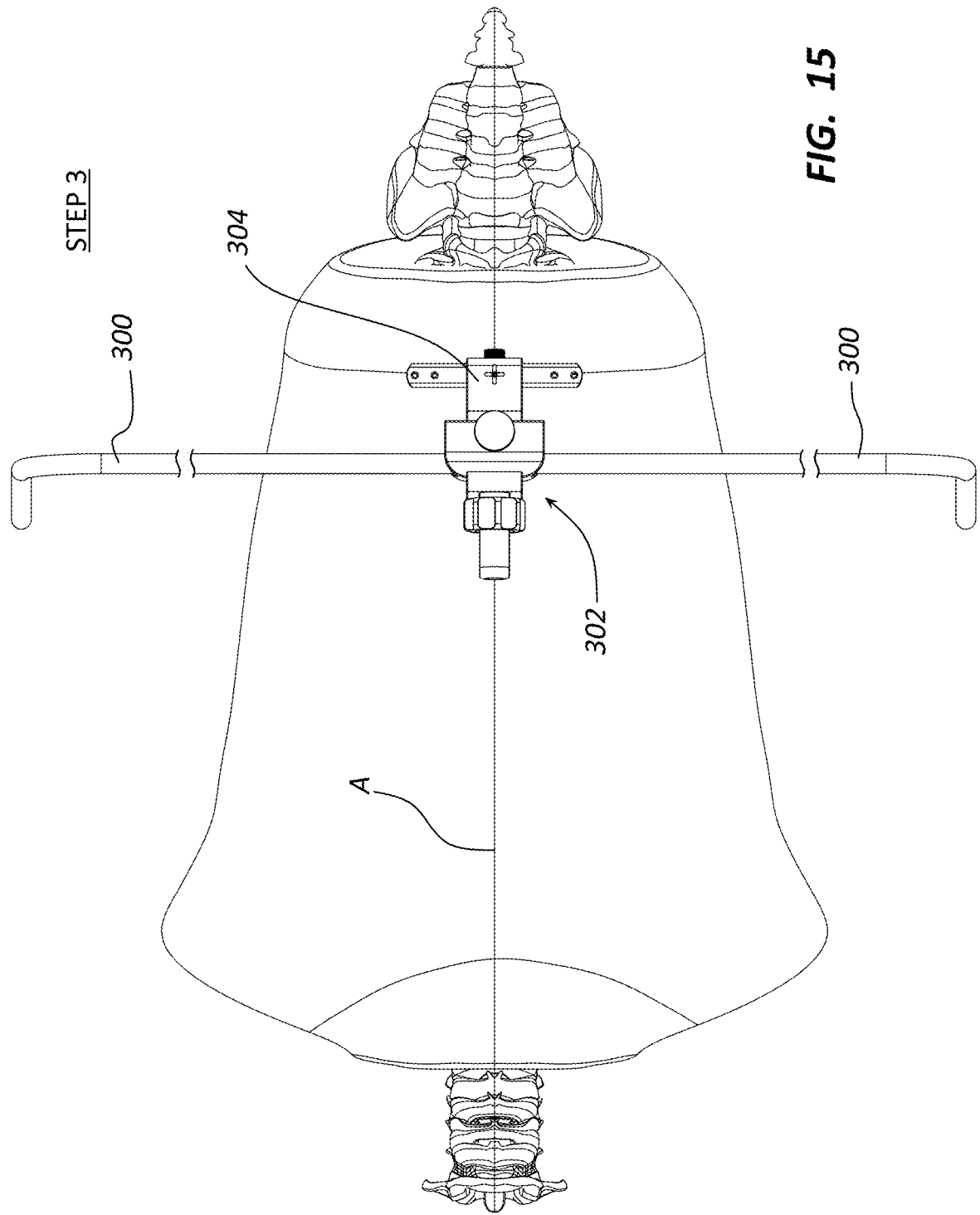
Figure 16:
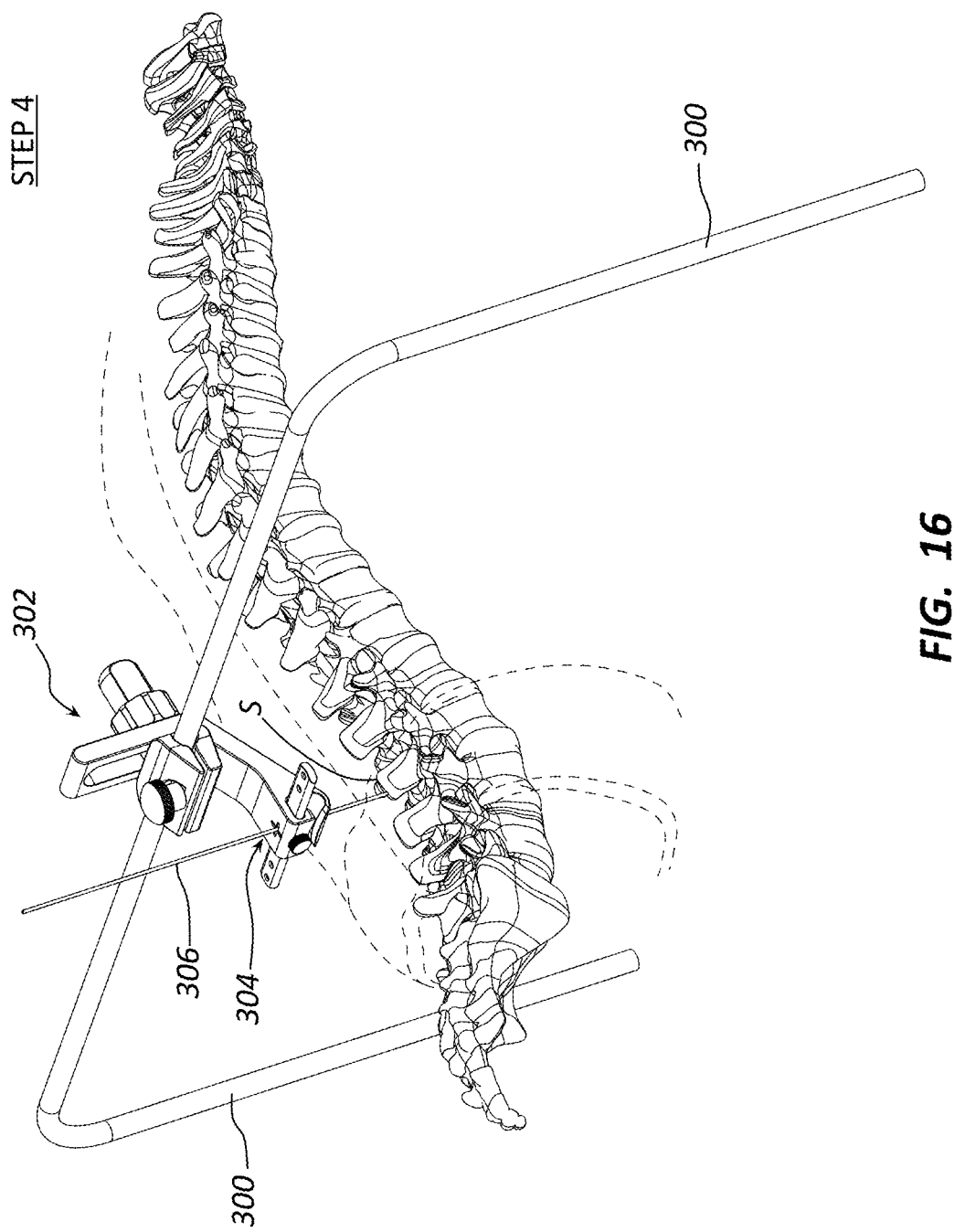
Figure 17:
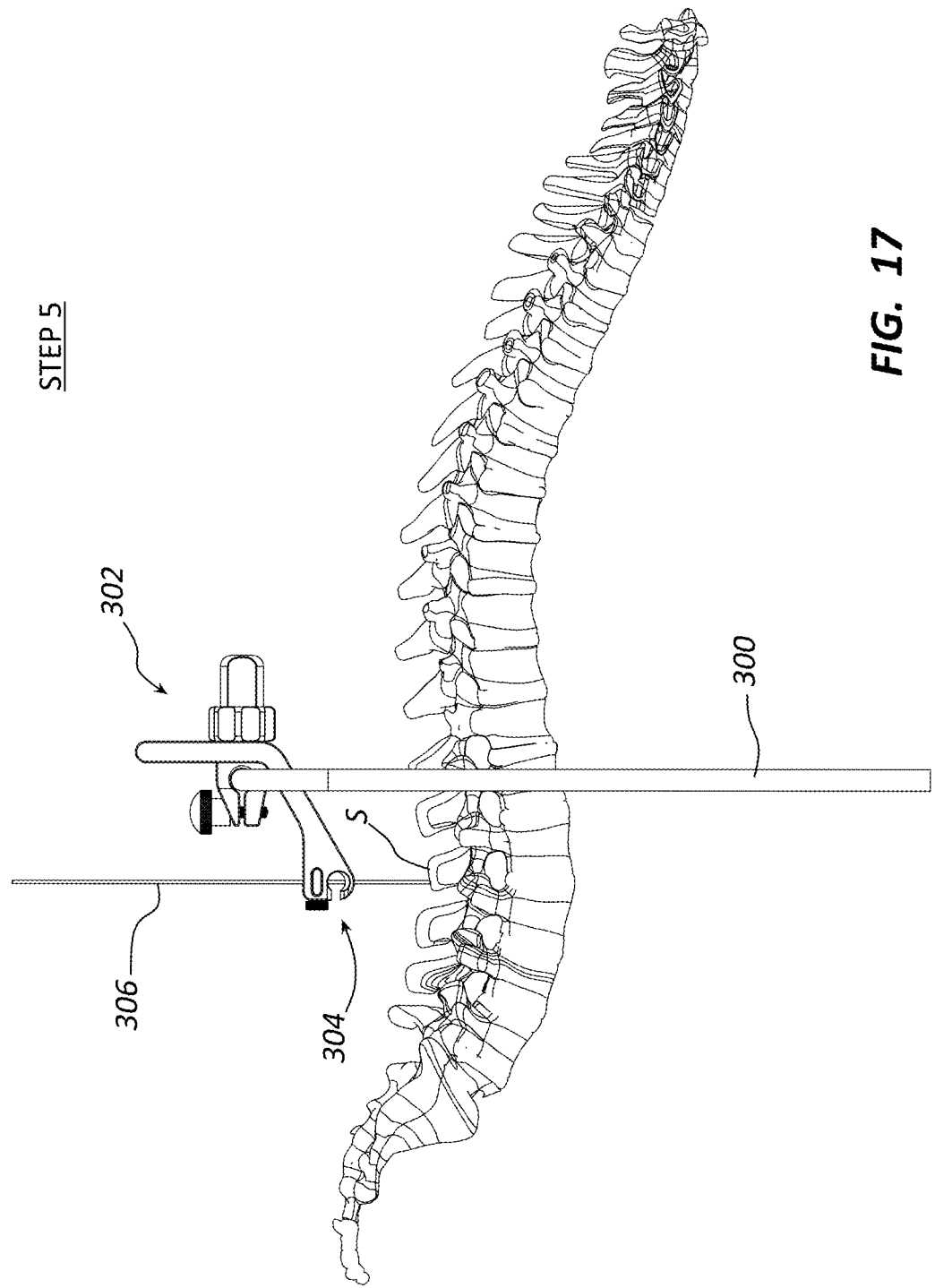

FIGS. 13-35 illustrate a particular method according to the present invention, which is achieved through a posterior to lateral approach. FIG. 13 shows how crossbar 300 may be attached to the bed or operating table (not shown), securing the system in place relative to the patient on which the procedure is being performed. As shown in FIG. 14, rod insertion guide 302 is attached to the crossbar 300. FIG. 15 shows how the midline marker 304 on rod insertion guide 302 is adjusted to be aligned with the patient's midline (i.e., longitudinal axis "A"). As shown in FIG. 16, a dropwire 306 can be inserted through the midline marker 304, and passed through the skin of the patient, to the level of the spinous process "S" of the disc where the spinal fusion or other process is to be performed As shown in FIG. 17, the angle of dropwire 306 can be compared to the angle of the disc space "D" being addressed The rod insertion guide 302 can be adjusted so that the angle of dropwire 306 matches that of the disc being addressed (i.e., operated on). The distance between the spinous process "S" and the skin can also be noted, as described elsewhere herein. Using a relatively simple calculation, the height "H" to place rod insertion guide 302 above the patient's skin can be determined by subtracting the measured distance from the center of the disc to the spinous process "S" (taken from the CT scan), and the additional distance between the spinous process and the skin surface from twice the radius of the curved tool (e.g., rod) 314 to be used, as in the calculation below.

$$H=2R=\text{CTDSP}-\text{SSP}$$

Where H is the height at which the rod insertion guide 302 is to be placed above the patient's skin, R is the radius of the curved rod 314, CTDSP is the CT scan measured distance from the center of the disc to the spinous process "S", and SSP is the distance between the spinous process "S" and the skin.

Figure 18:
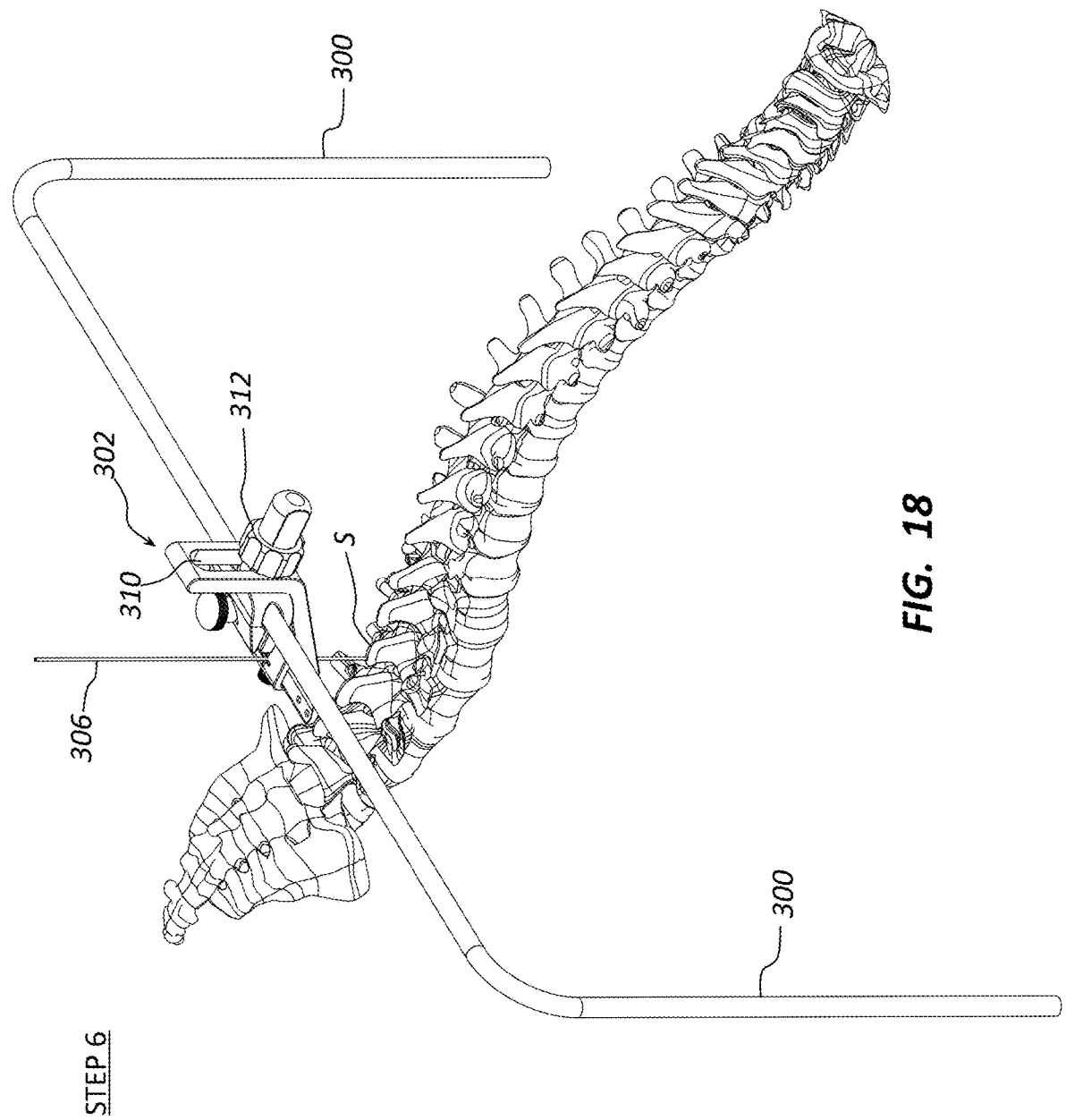
Figure 19:
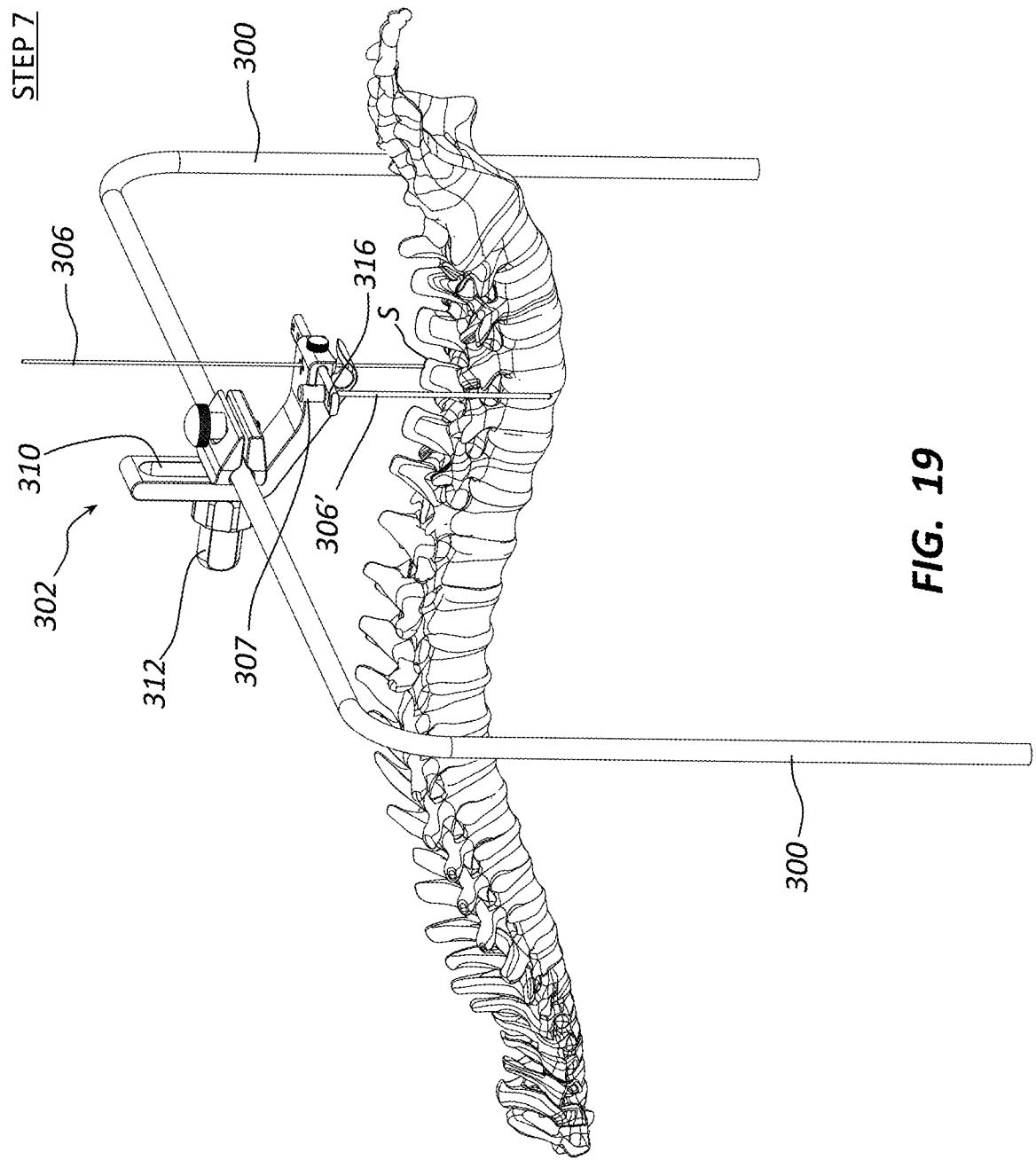

As shown in FIG. 18, rod insertion guide 302 can be adjusted up or down as needed, to ensure that the midline distance from the center of the disc space to the center of the curved rod path is approximately equal to twice the radius of the curved rod 314 to be used. Such up and down adjustment can be achieved using the slot and knob arrangement 310 and 312 respectively, as shown. It will be apparent that numerous other arrangements can also be suitable for making such an adjustment, and such are within the scope of the present disclosure. As shown in FIG. 19, a second rod (e.g., a confirmation rod) 306' can be inserted through one or more provided confirmation rod holes 316 in rod insertion guide 302 (e.g., laterally offset from the midline marker hole 304). As shown, more than one such hole 316 may be provided, at different lateral distances from the centerline hole 304 to accommodate different skeletal or other patient geometries. Rod 306' can be advanced through the skin and soft tissues, until the top portion of confirmation rod 306' is seated in the base of the confirmation rod hole 316. For example, where rod 306' includes an enlarged head 307 as shown, this can act as a stop, confirming to the practitioner that such seating of rod 306' relative to hole 316 has in fact occurred. The length of the confirmation rod 306' will be approximately equal to 2R, positioning the distal end of rod 306' at or near the center of the disc space to be operated on (only laterally offset therefrom).

Figure 20:
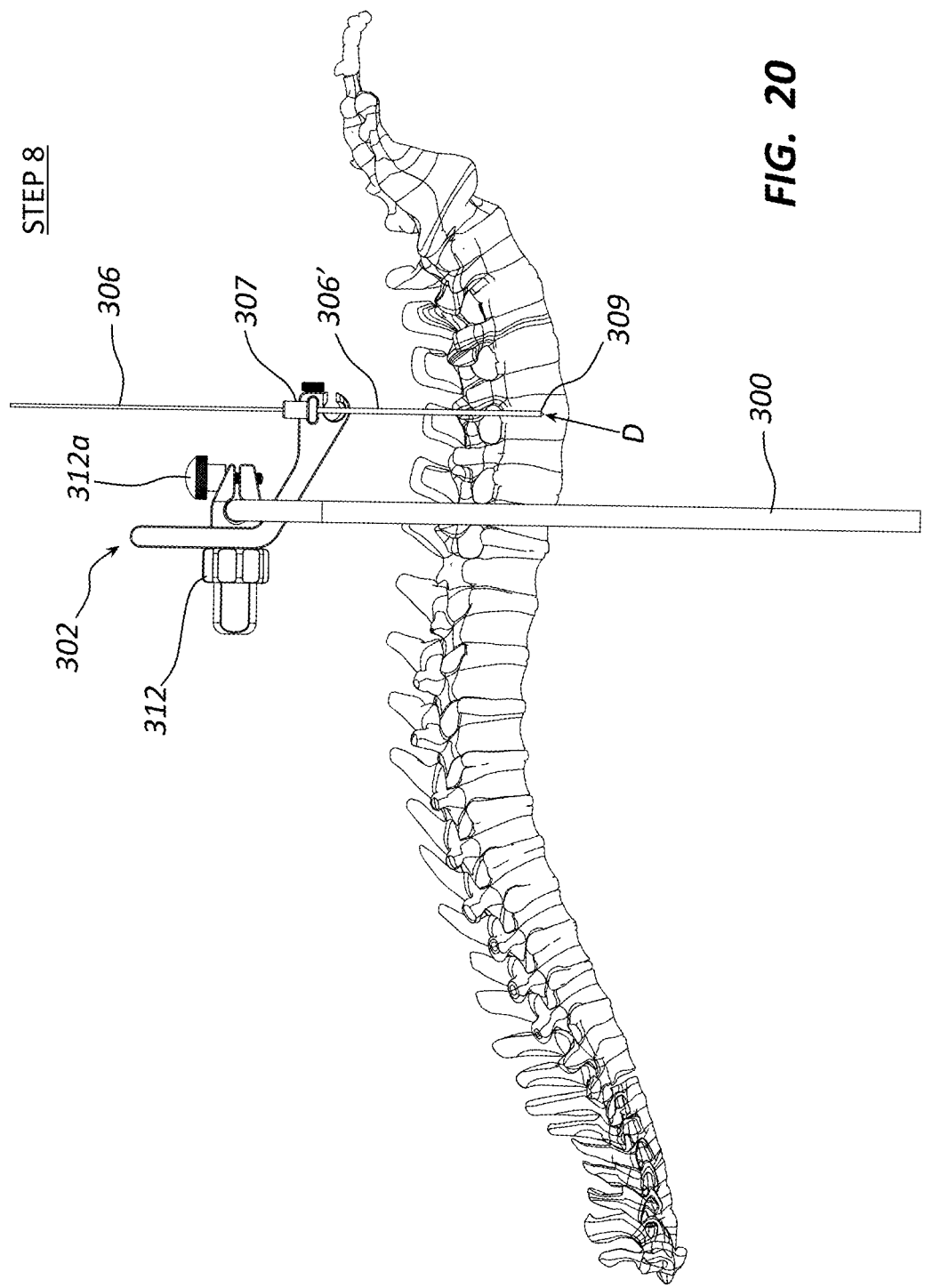
Figure 21:
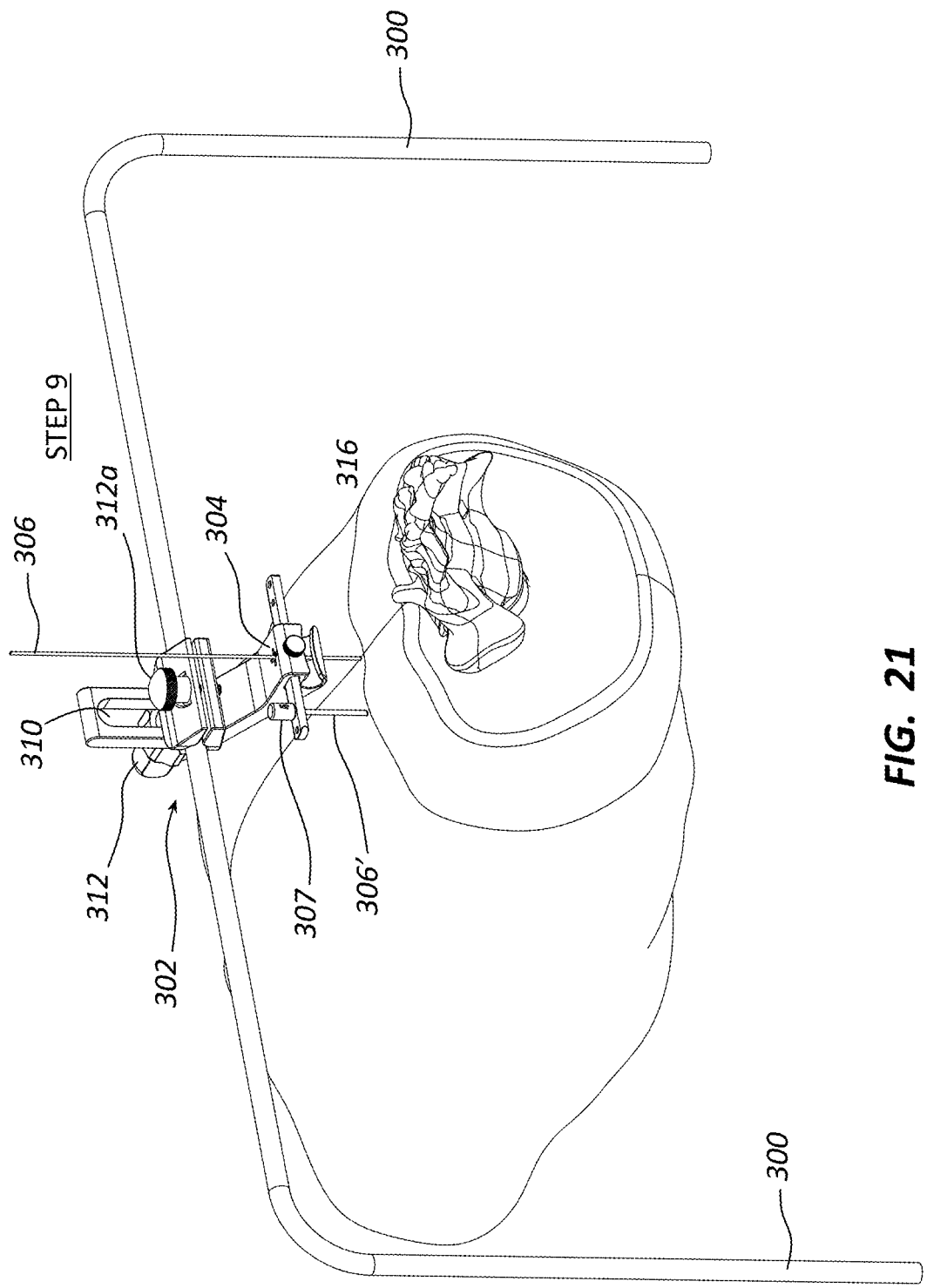
Figure 22:
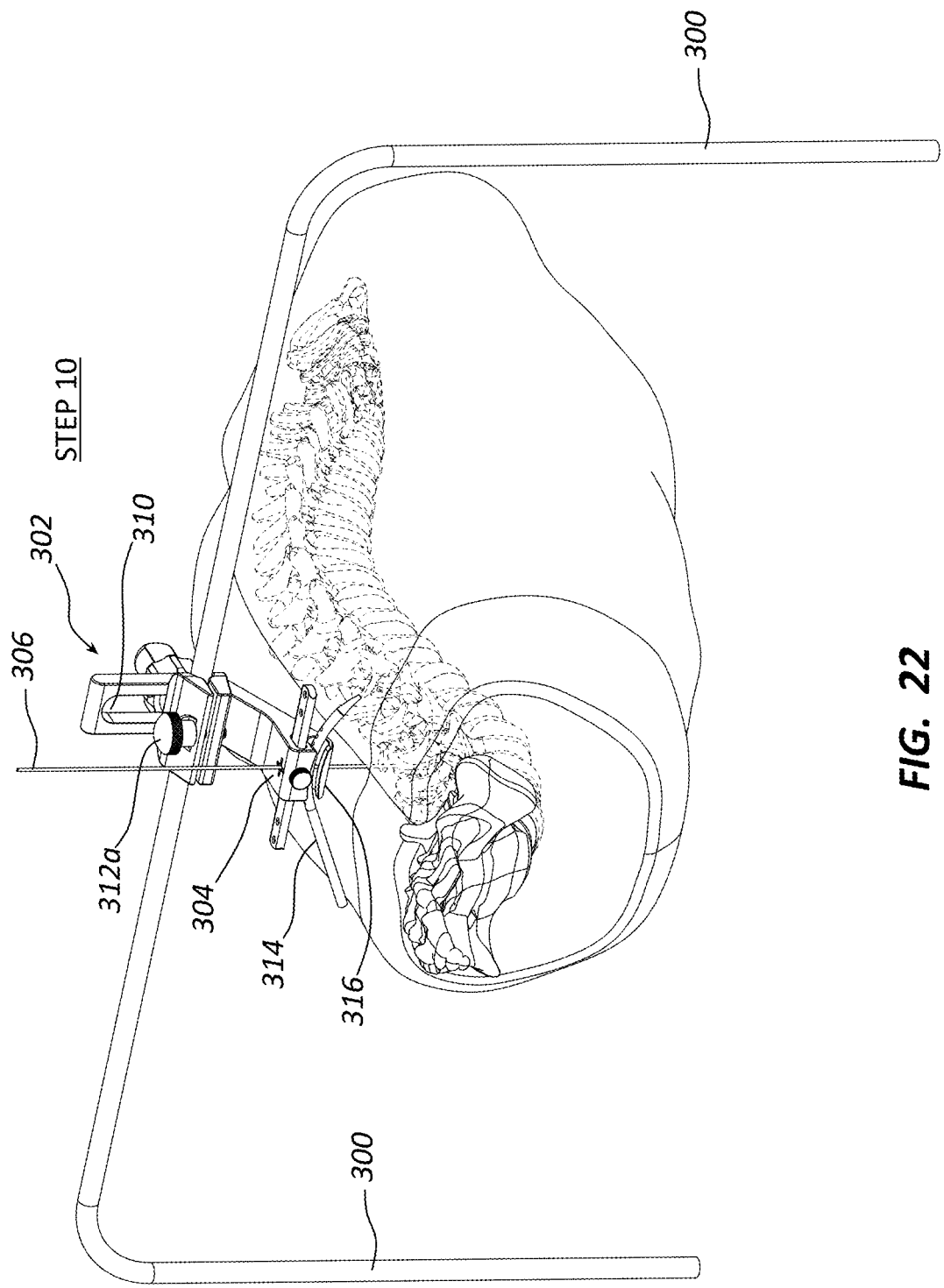

Referring to FIG. 20, additional adjustments can be made so that the tip 309 of confirmation rod 306' is at the same level as the center of the disc space "D" and at the desired angle, e.g., as seen on a lateral fluoroscopic view. Turning now to FIG. 21, after making any needed adjustments, rod insertion guide 302 is securely clamped in place by tightening the provided knobs or other structure (not shown) for securing the crossbar 300 (e.g., to the bed or operating table) and the rod insertion guide 302 to the crossbar 300 (e.g., with knob 312a). As shown in FIG. 22, curved rod 314 can be placed into rod insertion guide 302 and advanced towards the exterior skin surface of the patient. As shown, curved rod 314 may be held or guided within a correspondingly curved guide structure 316 of rod insertion guide 302. For this step, the confirmation rod 306' may have first been removed, as shown.

Figure 23:
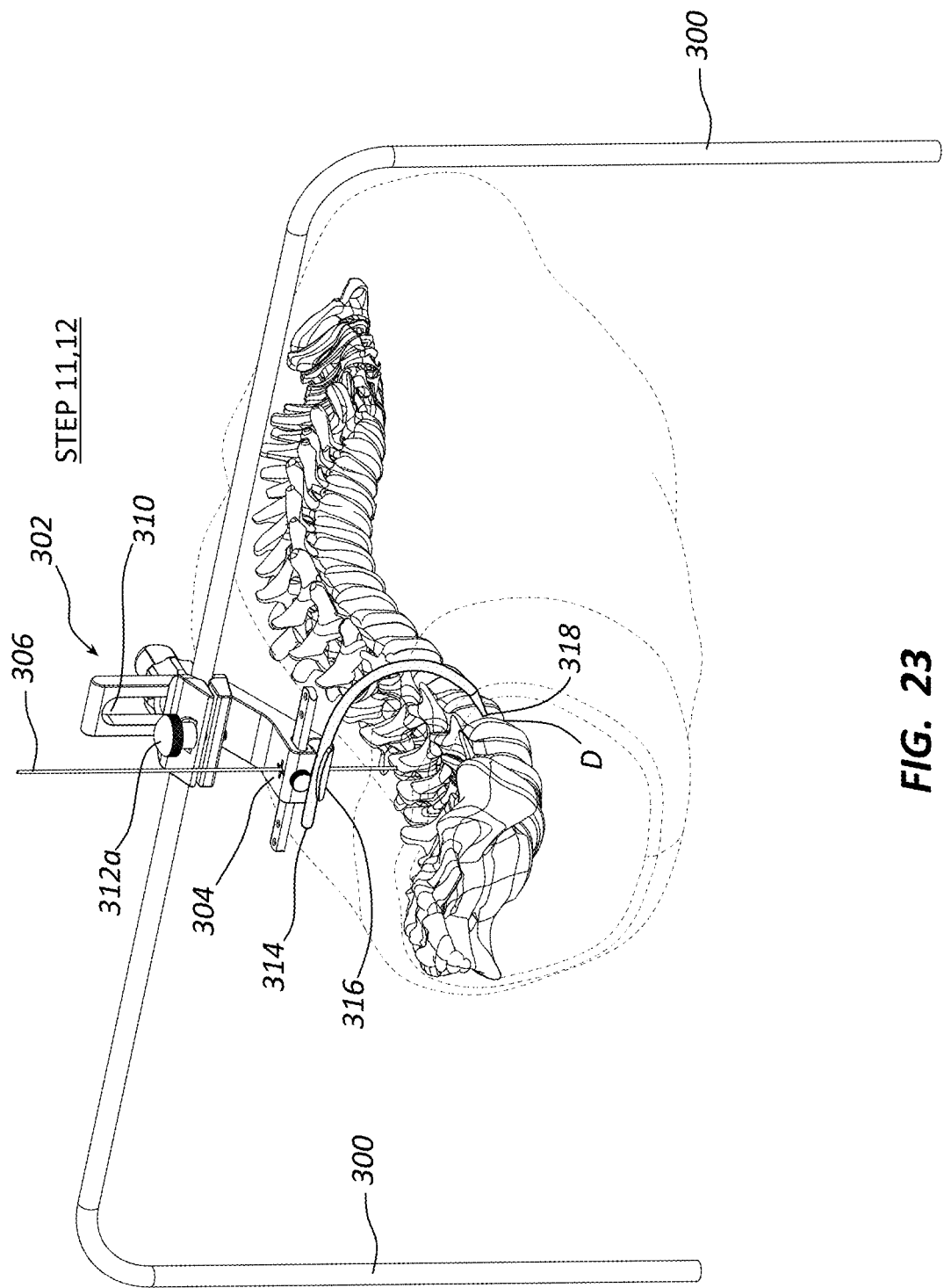
Figure 24:
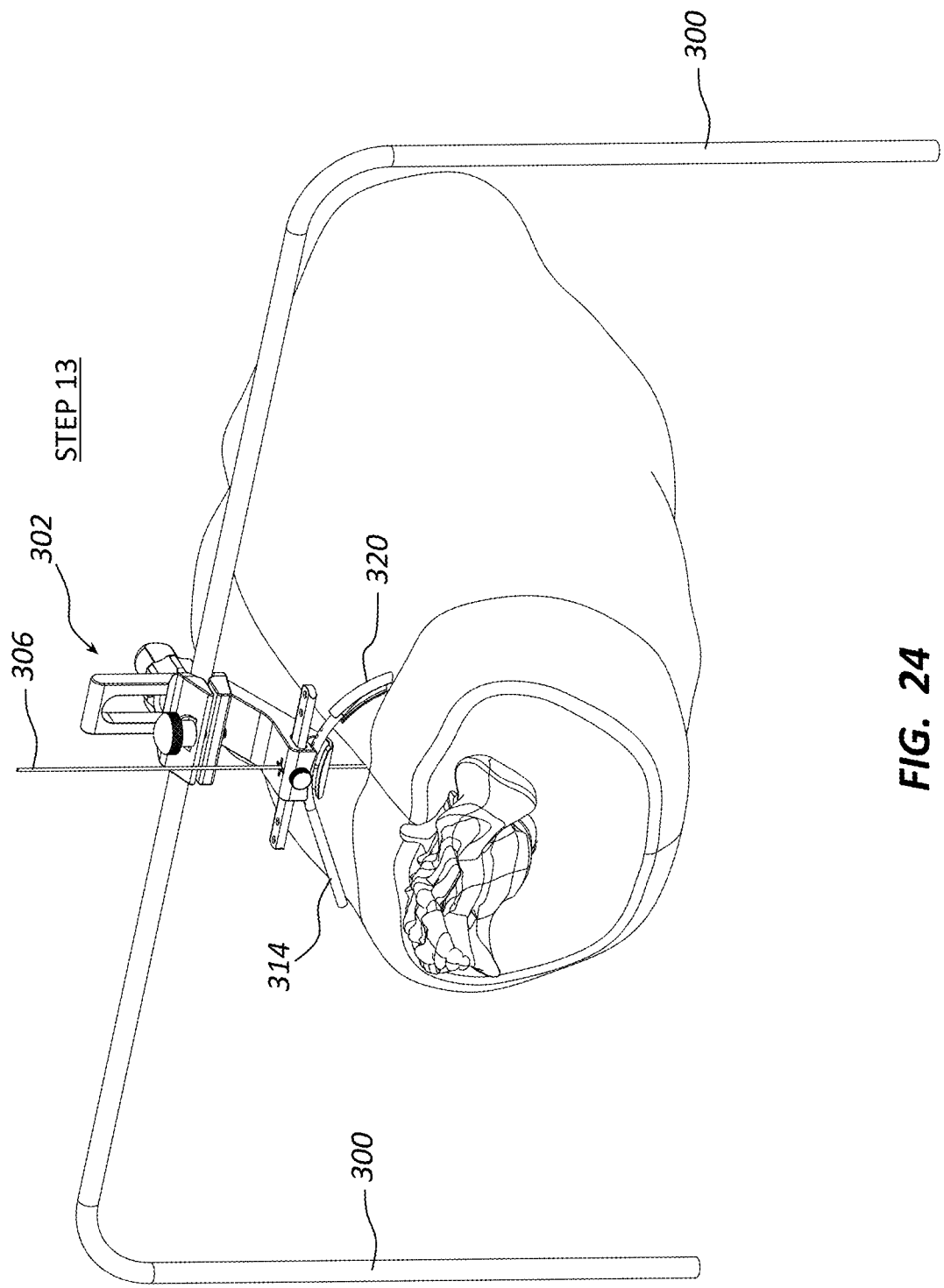
Figure 25:
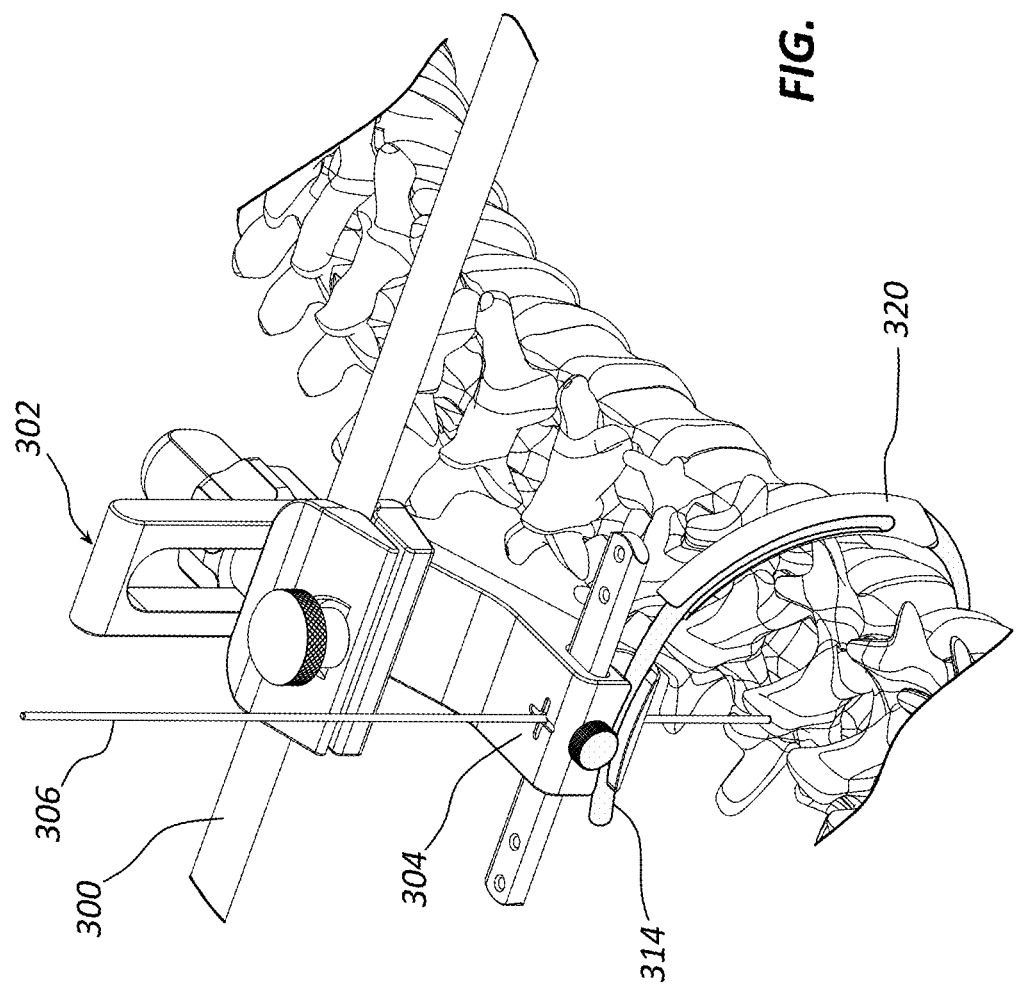

Use of confirmation rod 306' (and/or rod 306) is advantageous as it provides the practitioner with valuable confirmatory measurement information specific to the patient's skeletal and other geometry, so that once the curved tool 314 is advanced along the posterior to lateral pathway, it arrives at or very near the desired center of the disc targeted for fusion or other procedure being performed As shown in FIG. 23, the curved insertion rod 314 enters from a posterior approach, and is advanced through the skin and soft tissues (passing through the psoas muscle) until the rod reaches the lateral aspect of the disc space "D". The tip 318 of curv ed insertion rod 314 should contact the lateral aspect of the disc at the center of the disc, or slightly posterior to the center, relative to the disc space "D". The practitioner may electrically stimulate the curved insertion rod 314 to check for any interaction with any nearby neurological structures, e.g., as described in Applicant's other patents and applications (e.g. U.S. Pat. Nos. 8,740,956; 8,845,693; 9,668,775; 8,986,318; 9,084,633; 10,070,926; 9,486,257; 9,883,898; 10,278,737; and 10,058,361), each of which is herein incorporated by reference in its entirety. Referring to FIG. 24, if the path of the curved insertion rod 314 is correct, then rod 314 is removed and reinserted through curved cannula 320 with an outer sleeve to provide congruency.

Figure 26:
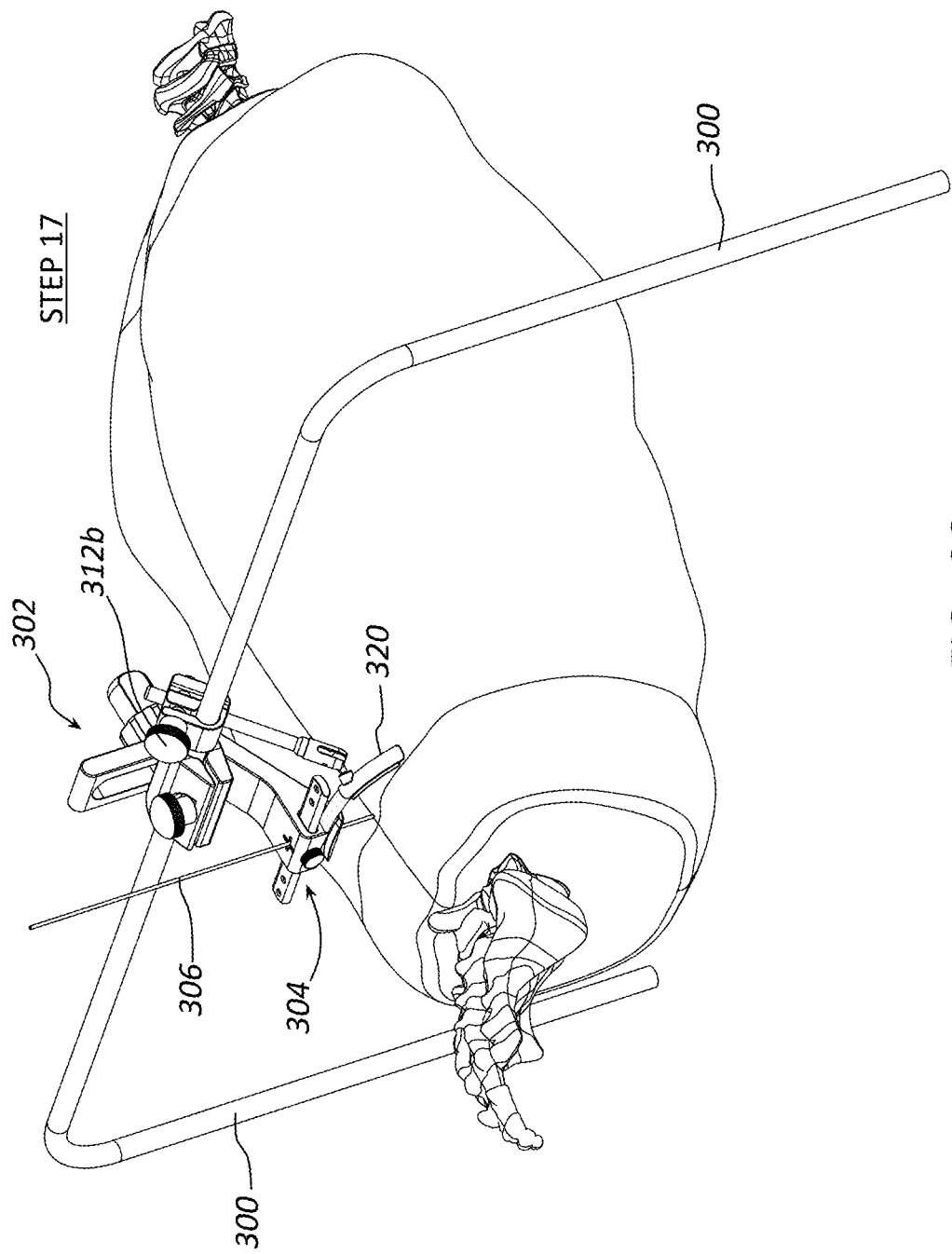
Figure 27:
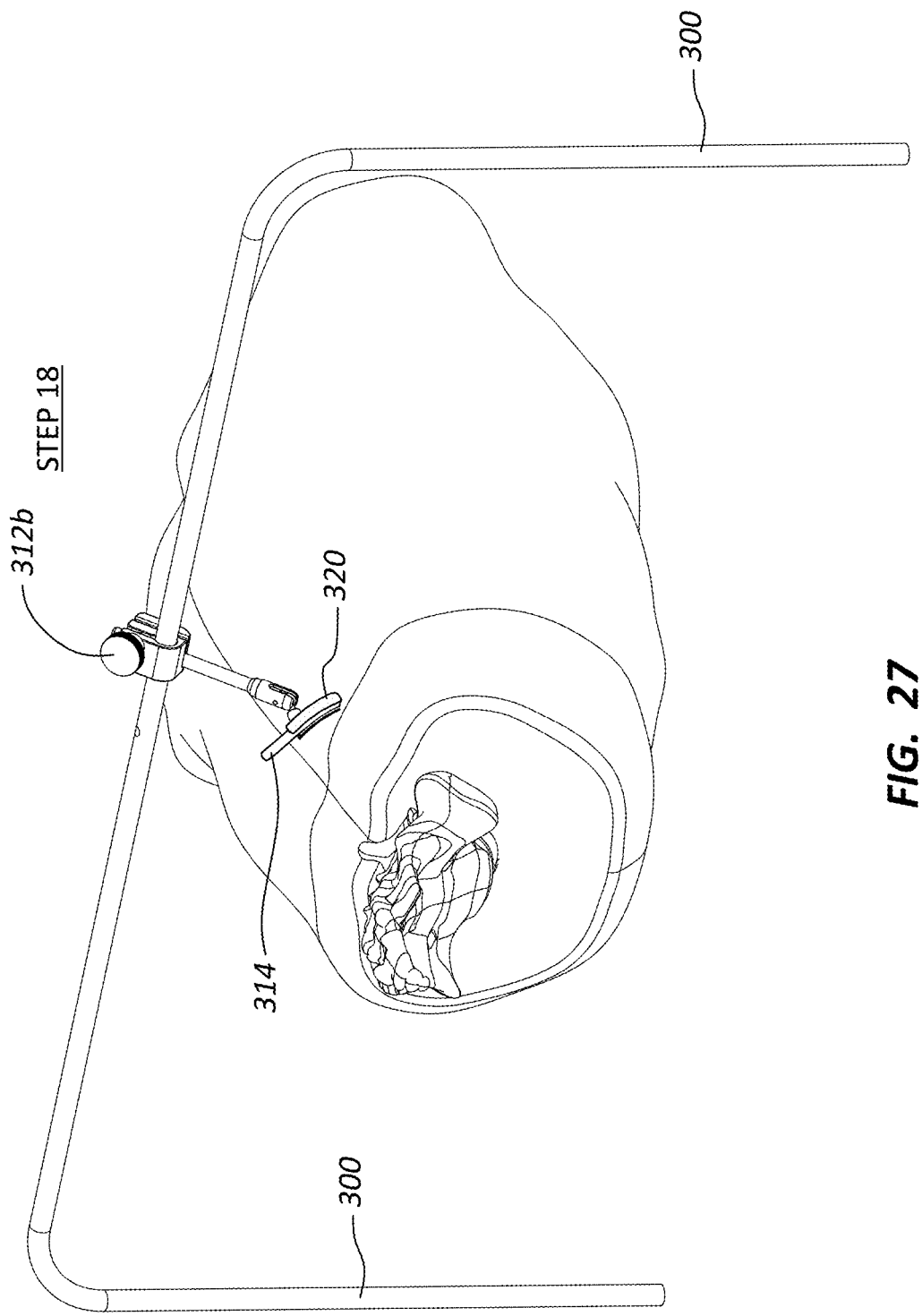
Figure 28:
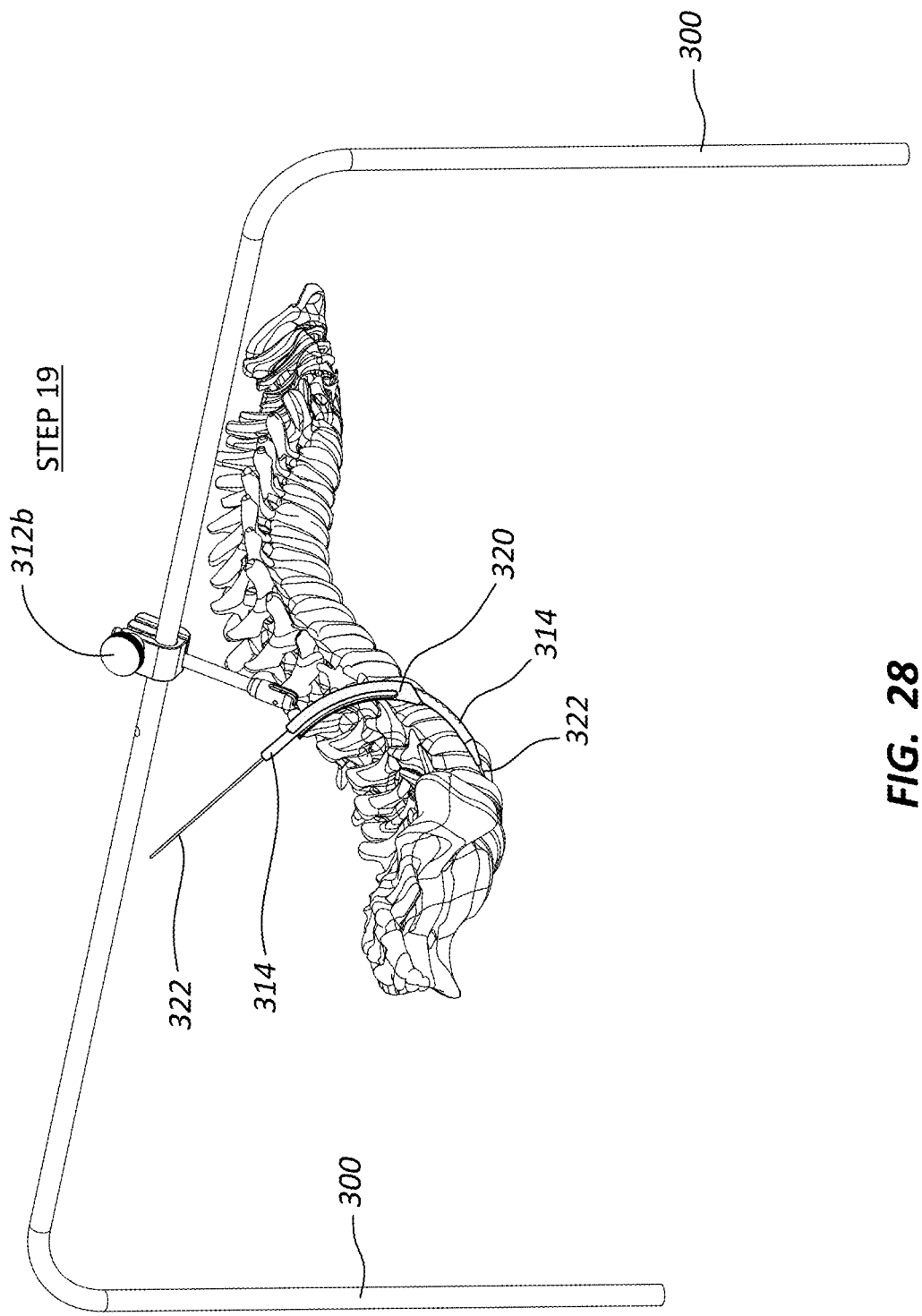
Figure 29:
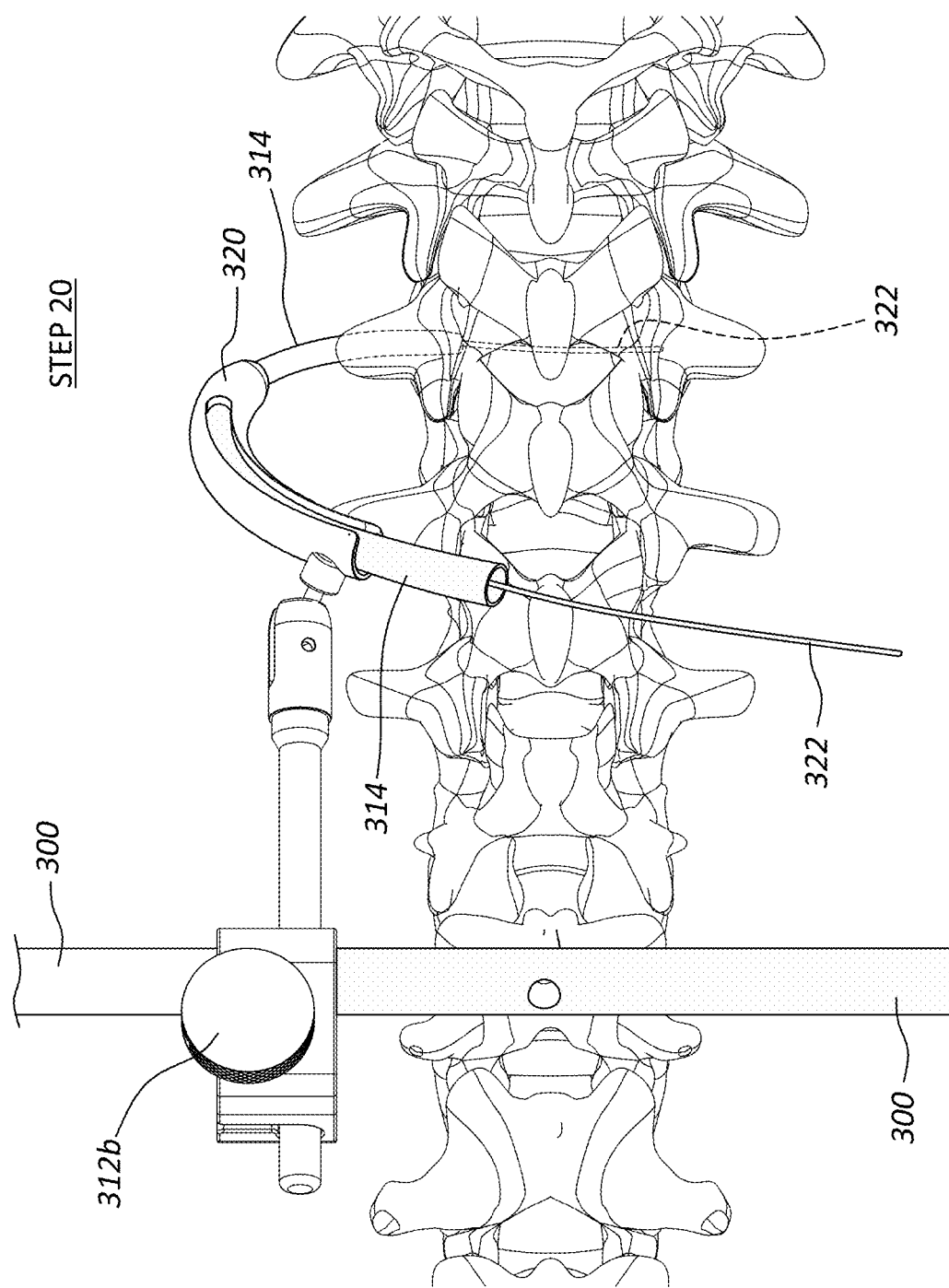

As shown in FIG. 25, the curved rod is again advanced to the lateral aspect of the disc (e.g., through cannula 320). A small incision can be made through the skin to allow for the cannula 320 to be advanced over the curved insertion rod 314. The cannula 320 with its sleeve are advanced through the soft tissue (including through the psoas muscle in the posterior to lateral approach pathway), over the curved insertion rod to the skin level. As shown in FIG. 26, the cannula 320 can be securely clamped to the crossbar 300 or other anchor point by tightening an appropriate knob (e.g., 312b) or other securing mechanism, securing the cannula 320 in place, which provides a curved posterior to lateral pathway directly to the desired disc space It will be apparent that various mechanisms can be used for securing the cannula 320 relative to any anchoring structure (e.g., crossbar 300 or otherwise), any of which are within the scope of the present disclosure. As shown in FIG. 27, at this point, the rod insertion guide 302 may then be removed. Referring to FIG. 28, a guidewire 322 can be placed through the cannula 320 and/or curved insertion rod 314 (e.g., where rod 314 is hollow), passing along and through the disc space through to the opposite side of the disc annulus, as shown in FIG. 29. Fluoroscopy can be used to confirm correct placement of the guidewire.

Figure 30:
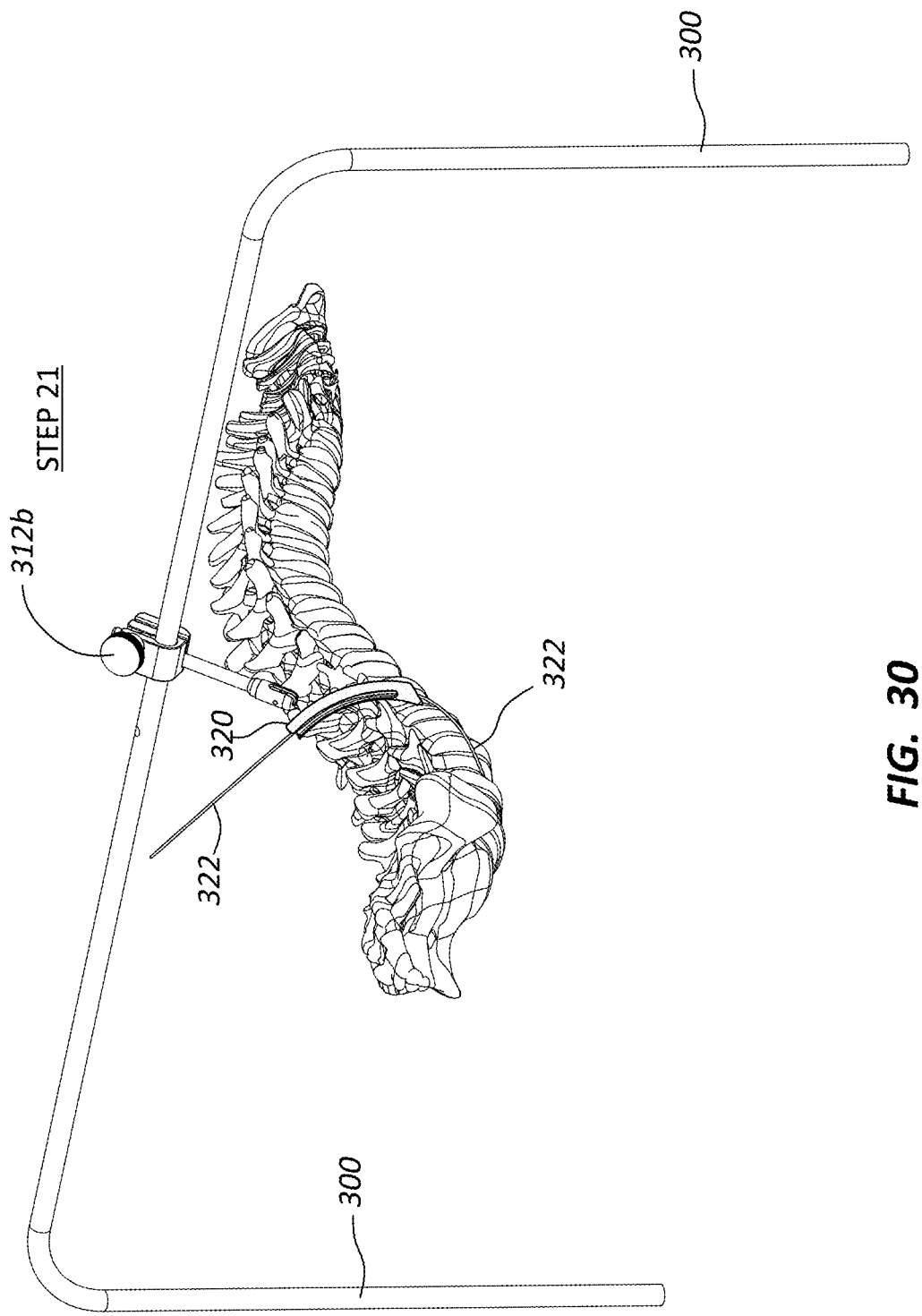

As will also be apparent from FIG. 29, in an embodiment, the guidewire 322 may be secured relative to both endplates of the target disc space, providing greater stability to any operations subsequently performed in the disc space (e.g., clearing). For example, by securing both ends relative to the end plates, clearing may be achieved with a subsequently placed cutting device, with anchoring provided at 2 points, at both ends of the disc space. As shown in FIG. 30, taking care not to retract the guidewire 322, the curved insertion rod 314 can be removed, leaving the guide wire 322 within the cannula 320, in position.

Figure 31:
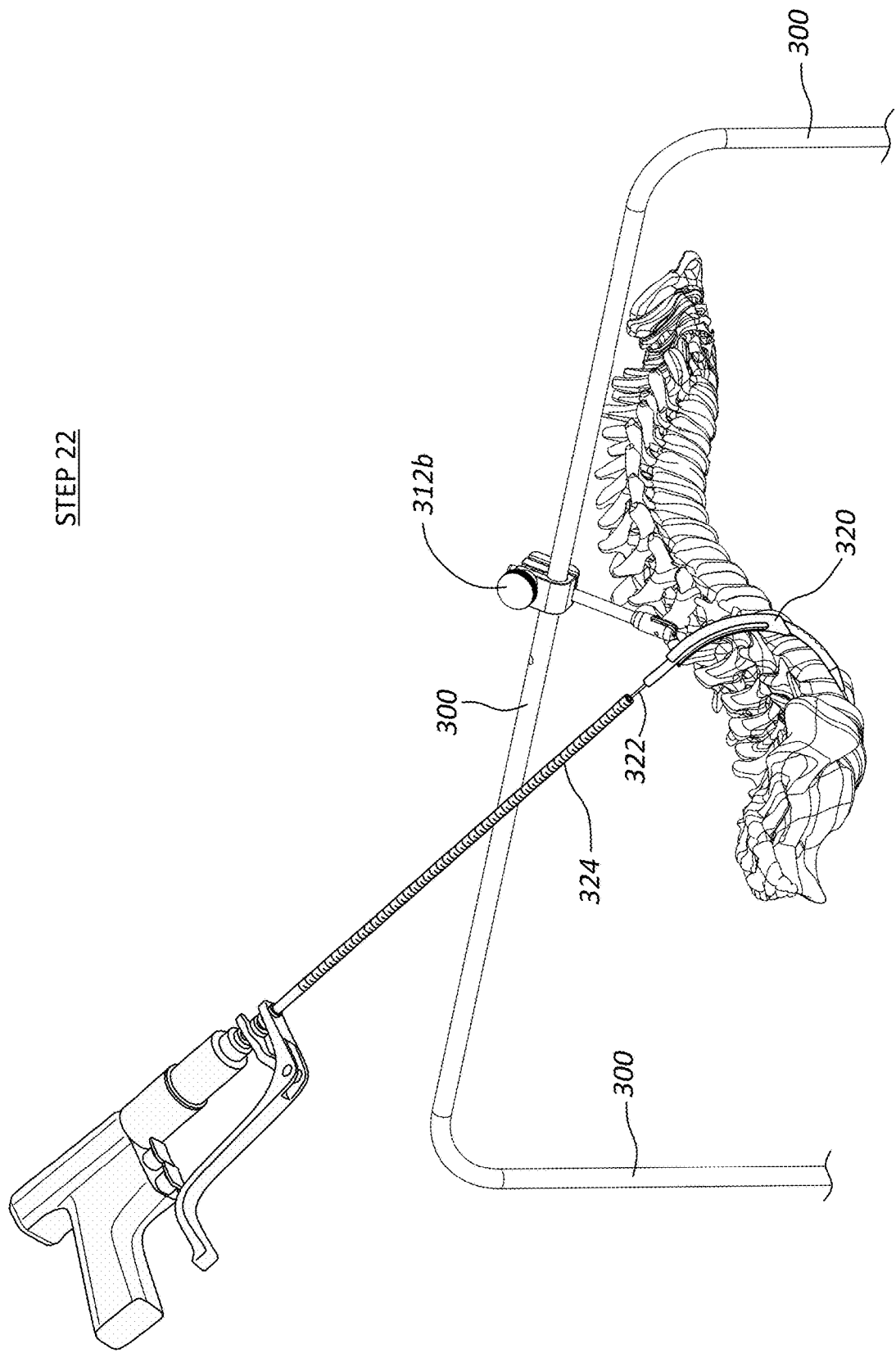
Figure 32:
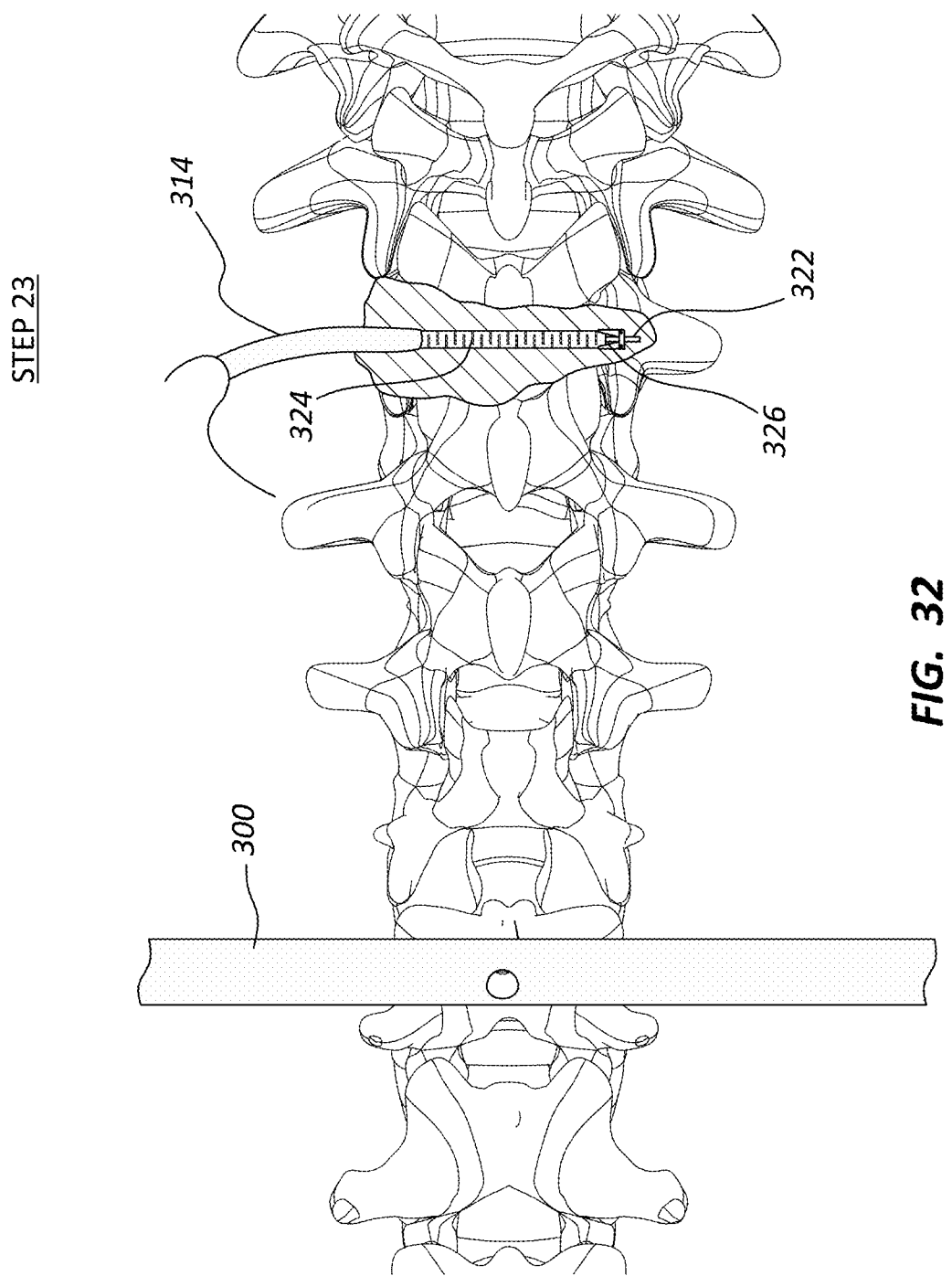
Figure 33:
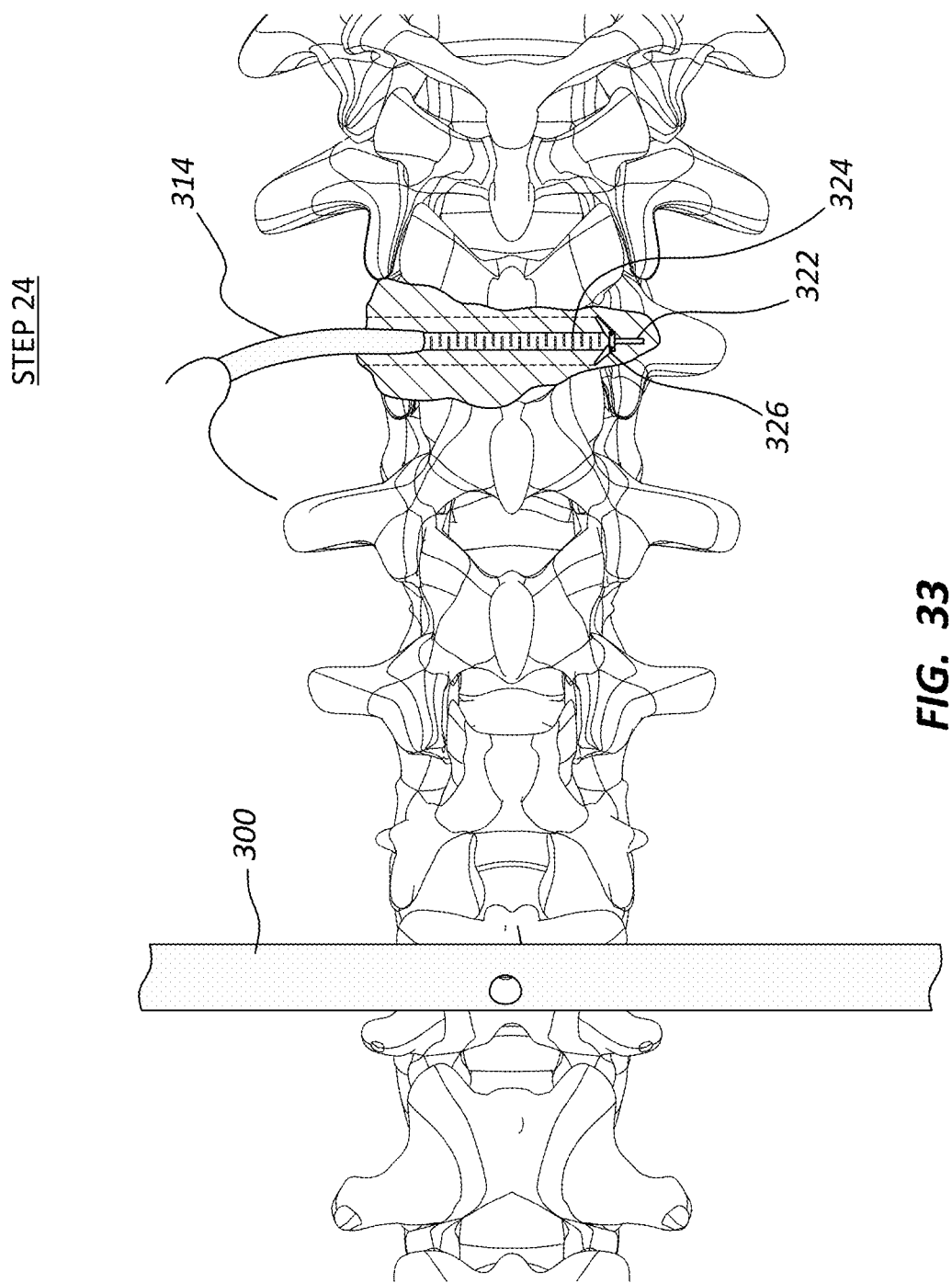

Referring to FIG. 31, a flexible cutting tool 324 (e.g., such as any described herein, or others in the art) can be inserted over the guidewire 322 and through cannula 320. The flexible cutter 324 is advanced over the guidewire through the annulus and into the disc space "D", as shown in FIG. 32. Such advancement of the cutting tool 324 can be along the same posterior to lateral pathway already established. As shown in FIG. 33, under fluoroscopic visualization, the flexible cutter 324 can be used to cut a generally cylindrical opening through the endplates within the disc space "D". Such should be done carefully, and with a pulling rather than a pushing motion. For example, cutting may be initiated with the blades 326 of the cutter 324 retracted, with the distal end of the cutting device already fully advanced (e.g., through the annulus). The blades 326 may be expanded or deployed, as the cutter 324 is rotating, and the cutting device may then be slowly retracted. Once the blades 326 of cutter 324 are deployed and are cutting through the endplates, the cutter 324 is pulled back through the disc space until the desired space or opening has been cleared.

In an embodiment, disc preparation may be performed under direct visual observation, e.g., use of a fiber optic or similar tool with camera deployed along the posterior to lateral path, to aid in clearing of the disc space. The ability of a cutting tool to expand (e.g., retractable blades 326) is particularly beneficial, minimizing the invasiveness of the approach to the disc space.

Figure 34:
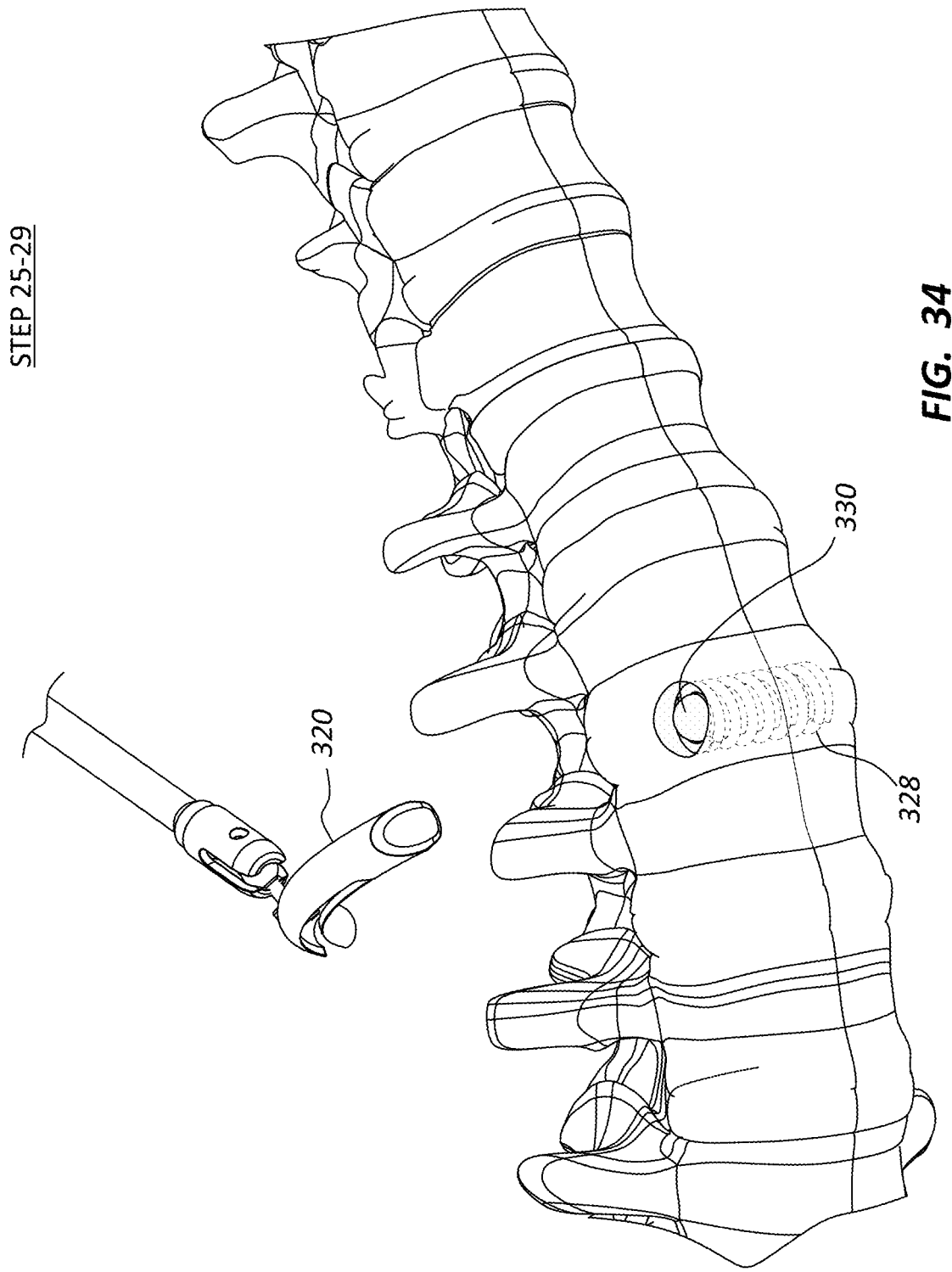

At this point in the procedure, the practitioner may choose to use a "biologic" to assist in achieving fusion, such as an autograft, allograft, or other material delivered through a curved tube. In an embodiment, the practitioner may place an implant within the emptied disc space to provide additional stability to the prepared disc space. For example, using the guidewire 322, a mechanism (e.g., tool) for inserting the implant is passed into the disc space along the same curved pathway already employed to access the disc space. Such an implant may be formed from a nitinol or other shape memory material that is inserted in a relatively straight configuration, and which assumes a coiled shape once inside the prepared disc cavity, as shown in FIG. 34. The wire is initially advanced slowly allowing the coil to secure its position and then more rapidly as the coil takes shape. The ability of the nitinol or other shape memory wire to assume its coiled shape may require shape setting of the material, and appropriate transition temperatures, as will be appreciated by those of skill within the art. For example, a suitable transition temperature may be just below (e.g., within 5° C., within 3° C., or within 2° C.) body temperature (37° C.), e.g., such as 35° C. More generally, implant 328 may comprise an expandable cage structure (e.g., coil or otherwise).

Figure 35:
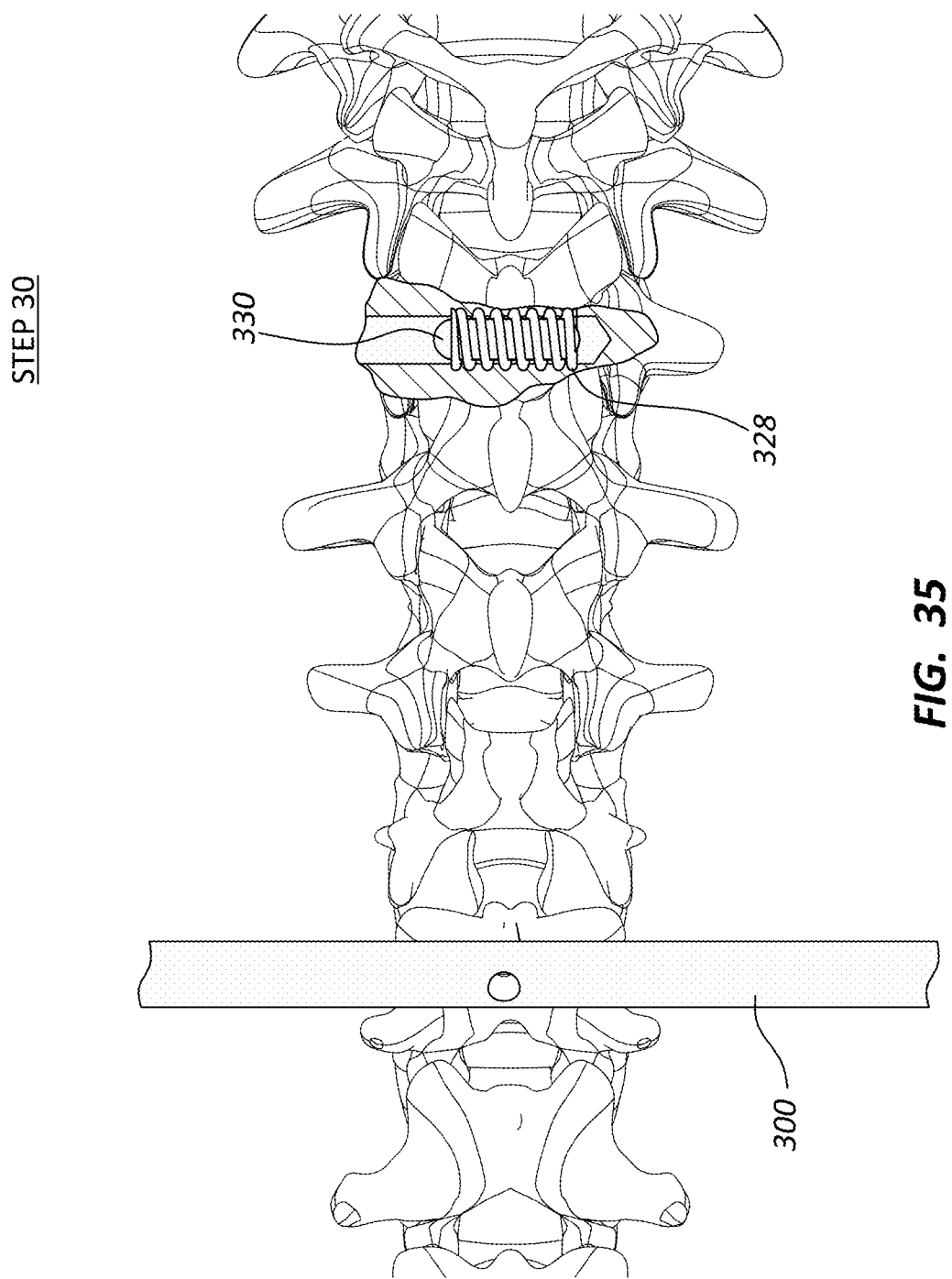

Such a procedure allows a relatively rigid and supportive implant structure to be inserted through the curved posterior to lateral pathway provided, advantageously providing supportive structure within the disc space. Such may be used in combination with, or alternative to introduction of any biologic grafting material introduced into the cleared disc space. For example, once such an implant has been deployed, an appropriate biologic graft material may be employed, to facilitate the long-term success of the fusion. Finally, the guidewire 322 and cannula 320 can be removed, and the incision closed. FIG. 35 shows the expandable cage implant 328 (e.g., a shape memory coil) in place, with the grafting material 330 also positioned in the prepared disc space, e.g., inside the cage provided by implant 328.

The posterior to lateral approaches may allow an approach to the right, or to the left, around the "side" of the patient, with the tools for entry mounted along a posterior surface of the patient (e.g., with the patient lying on their stomach). For example, while the approach illustrated in the Figures (e.g., see FIG. 29) is shown as to the left of the spinal column, it will be appreciated that a similar approach could be made as a mirror image, e.g., to the right of the spinal column, also using a posterior to lateral approach.

Embodiments herein are principally described in which the tool is advanced along the desired path towards the lateral aspect of the disc, and during such advancement, or even after such advancement, deviating from the typically straight posterior or posterolateral path to a lateral, or substantially lateral path. Such deviation may occur during advancement, after advancement, or anywhere therebetween. For example, deviation may occur as the leading end of the tool approaches, reaches, or nearly reaches the lateral aspect of the disc. Approaching or nearly reaching the lateral aspect of the disc may be, e.g., within about 1 cm of the lateral aspect of the disc, within about 5 mm, within about 3 mm, or within about 1 mm of the disc.

The procedures described herein may be performed with the assistance of fluoroscopy or similar real-time imaging to avoid damage to the adjacent vital structures including: the vena cava, iliac veins, nerve roots and thecal sac within the spinal canal Neuromonitoring may also be employed (e.g., throughout the procedure, including during placement of the cannula, as well as while the disc space is cleared) to detect any inappropriate interaction with the neurological structures.

It will be apparent that the present methods allow advancement of a tool along a posterior to lateral approach path to the disc, without such tool (or any tool) having to approach the disc from a posterior approach (particularly where such posterior approach would require navigation through tissues other than soft or relatively insensitive tissues (e.g., bone, nerves, etc.). Probing rods 306, 306' do not require any of such, and are of course optional, anyway.

Numbers, percentages, ratios, or other values stated herein may include that value, and also other values that are about or approximately the stated value, as would be appreciated by one of ordinary skill in the art. As such, all values herein are understood to be modified by the term "about". A stated value should therefore be interpreted broadly enough to encompass values that are at least close enough to the stated value to perform a desired function or achieve a desired result, and/or values that round to the stated value. The stated values include at least the variation to be expected in a typical manufacturing process, and may include values that are within 25%, within 10%, within 5%, within 1%, etc. of a stated value. Furthermore, where used, the terms "substantially", "similarly", "about" or "approximately" represent an amount or state close to the stated amount or state that still performs a desired function or achieves a desired result. For example, the term "substantially" "about" or "approximately" may refer to an amount that is within 25% of, within 10% of, within 5% of, or within 1% of, a stated amount or value.

Ranges between any values disclosed herein are contemplated and within the scope of the present disclosure (e.g., a range defined between any two values (including end points of a disclosed range) given as exemplary for any given parameter).

As used in this specification and the appended claims, the singular forms "a," "an" and "the" include plural referents unless the context clearly dictates otherwise.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A method for accessing a disc of a patient's vertebrae of the patient's spine as part of
a discectomy or spinal interbody fusion, the method comprising:
securing a device over a posterior surface of the patient's back with a tool coupled to the device, the device being adjusted to a given height above the posterior surface of the patient's back based on a measured distance taken from the patient;
inserting a leading end of the tool into the posterior or posterolateral surface of the patient's back and advancing the tool along a predetermined path that begins as a posterior or posterolateral approach to the disc, said path being curved;
advancing the tool along the pre-determined path which deviates from a posterior or posterolateral orientation towards a lateral orientation relative to the disc as the tool advances from the posterior or posterolateral surface through the psoas muscle of the patient until it has reached or nearly reached a lateral aspect of the disc; and
using the tool or a subsequent tool to access the disc and perform at least a portion of the discectomy or spinal interbody fusion.

2. A method as in claim 1, wherein the tool comprises or is used with a curved cannula.

3. A method as in claim 1, wherein a guiding device includes an insertion guide that is secured over the posterior surface of the patient's back, the insertion guide providing an insertion point for the leading end of the tool that is offset some distance laterally from a midline of the patient, and the tool is advanced through a predetermined path, the predetermined path being substantially an arc length of a circle having a radius based at least in part on a measured distance from the spinous process to the center of the disc and/or a measured distance from the patient's posterior skin surface to the spinous process.

4. A method as in claim 1, wherein the measured distance includes a distance from the tip of the spinous process to the center of the disc.

5. A method as in claim 4, wherein both the distance from the tip of the spinous process to the center of the disc and the distance from the spinous process to the skin are measured.

6. A method as in claim 1, the method further comprising clearing a disc space of the disc with a rotating cutting device.

7. A method as in claim 6, wherein the rotating cutting device is advanced along the same path along which the tool was advanced towards the disc.

8. A method as in claim 6, wherein the rotating cutting device is anchored on both ends of the disc space prior to clearing, providing greater stability during clearing of the disc space.

9. A method as in claim 6, the method further comprising placing an expandable cage implant into the disc space after it has been cleared.

10. A method as in claim 9, wherein the expandable cage implant is a coil formed from a shape memory material.

11. A method as in claim 9, wherein the expandable cage implant is inserted through a curved cannula, along the same path along which the tool was advanced towards the disc, in a substantially collapsed configuration, the expandable cage expanding to assume its expanded configuration after entering the cleared disc space.

12. A method as in claim 9, further comprising filling the disc space and/or a space within the expandable cage with a grafting material.

13. A method for accessing a disc of a patient's vertebrae of the patient's back as part of a discectomy or spinal interbody fusion, the method comprising:
measuring a distance from a desired reference point to the disc, where the reference point is between-the spinous process and the surface of the skin;
securing a guiding device over a posterior surface of the patient's back, the guiding device including a guide, a position of which is adjusted based at least in part on said measured distance, the guide accommodating an approach radius for a tool that is configured to direct the tool towards the lateral aspect of the disc;
inserting a leading end of the tool into the posterior or posterolateral surface of the patient's back at the start of a predetermined path, the path being at least partially determined by the guiding device, the path beginning as a posterior or posterolateral approach to the disc;
advancing the tool along the predetermined path which deviates from the posterior approach towards a lateral approach as the tool is advanced from the posterior surface towards a lateral aspect of the disc; and
using the tool, or a subsequent tool, to access the disc through the psoas muscle and perform at least a portion of a discectomy or a spinal interbody fusion.

14. A method as in claim 13, wherein the guiding device includes an insertion guide that is secured over the posterior surface of the patient's back, the insertion guide providing an insertion point for the leading end of the tool that is offset some distance laterally from a midline of the patient, and the tool is advanced through the predetermined path, the predetermined path being substantially an arc length of a circle having a radius based at least in part on a measured distance from the spinous process to the center of the disc and/or a measured distance from the patient's posterior skin surface to the spinous process.

15. A method as in claim 13, wherein the reference point is a tip of the-spinous process of the patient.

16. A method as in claim 13, wherein the measured distance is a distance from the tip of the spinous process to the center of the disc.

17. A method as in claim 13, wherein both the distance from the tip of the spinous process to the center of the disc and the distance from the spinous process to the skin are measured.

18. A method as in claim 13, the method further comprising clearing a disc space of the disc with a rotating cutting device.

19. A method as in claim 18, wherein the rotating cutting device is advanced along the same path along which the tool was advanced towards the disc.

* * * * *